(12) United States Patent
Hofstetter et al.

(10) Patent No.: US 11,869,378 B2
(45) Date of Patent: Jan. 9, 2024

(54) SURGICAL TRAINING MODEL FOR LAPAROSCOPIC PROCEDURES

(71) Applicant: Applied Medical Resources Corporation, Rancho Santa Margarita, CA (US)

(72) Inventors: Gregory K. Hofstetter, Rancho Santa Margarita, CA (US); Tracy Breslin, Trabuco Canyon, CA (US); Khodr Saleh, Whittier, CA (US); Natasha Felsinger, Trabuco Canyon, CA (US); Katie Black, Rancho Santa Margarita, CA (US); Milan Draganov, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 17/840,392

(22) Filed: Jun. 14, 2022

(65) Prior Publication Data

US 2022/0309955 A1 Sep. 29, 2022

Related U.S. Application Data

(60) Division of application No. 16/897,142, filed on Jun. 9, 2020, now Pat. No. 11,361,679, which is a continuation of application No. 15/166,661, filed on May 27, 2016, now Pat. No. 10,679,520.

(60) Provisional application No. 62/318,902, filed on Apr. 6, 2016, provisional application No. 62/167,129, filed on May 27, 2015.

(51) Int. Cl.
*G09B 23/30* (2006.01)
*G09B 23/28* (2006.01)
(Continued)

(52) U.S. Cl.
CPC .............. *G09B 23/30* (2013.01); *A61B 17/04* (2013.01); *G09B 23/285* (2013.01);
(Continued)

(58) Field of Classification Search
CPC ...... G09B 23/30; G09B 23/285; G09B 23/28; A61B 17/04
(Continued)

(56) References Cited

U.S. PATENT DOCUMENTS

| 184,573 A | 11/1876 | Becker |
| 2,127,774 A | 8/1938 | Jacobs |

(Continued)

FOREIGN PATENT DOCUMENTS

| CA | 2 293 585 A1 | 12/1998 |
| CN | 2421706 Y | 2/2001 |

(Continued)

OTHER PUBLICATIONS

European Patent Office, Extended European Search Report for European Patent Application No. EP 22151452.4, titled "Portable Laparoscopic Trainer," dated Apr. 13, 2022, 8 pgs.

(Continued)

*Primary Examiner* — Kurt Fernstrom
(74) *Attorney, Agent, or Firm* — Shirin Bozorgui; Patrick Ikehara

(57) ABSTRACT

A surgical training device is provided. The training device includes a model for practicing the passage of needle and suture. The model includes a base with a plurality of openings configured to receive a plurality of suture tabs. The suture tabs are made of elastomeric material. Some suture tabs includes pre-formed tab apertures for the passage of a suture. Other suture tabs include a penetrable area through which a suture needle may penetrate for passing a suture. The suture tabs are movable with respect to the base to orientate them at different angles with respect to the base. The base itself may include portions that are angled with respect to each other. The suture tabs are movable with respect to the base to pull, expose or open the tab apertures (Continued)

and surfaces. Some of the tab apertures are slits that open upon being pulled relative to the base requiring the user to practice holding the tab while passing the needle through the tab.

20 Claims, 26 Drawing Sheets

(51) Int. Cl.
    *A61B 17/04*     (2006.01)
    *G09B 23/32*     (2006.01)
    *G09B 23/36*     (2006.01)
    *G09B 23/34*     (2006.01)
    *A61B 17/00*     (2006.01)

(52) U.S. Cl.
    CPC .... *A61B 2017/00707* (2013.01); *G09B 23/28* (2013.01); *G09B 23/32* (2013.01); *G09B 23/34* (2013.01); *G09B 23/36* (2013.01)

(58) Field of Classification Search
    USPC ........................................................ 606/144
    See application file for complete search history.

(56) References Cited

U.S. PATENT DOCUMENTS

| | | |
|---|---|---|
| 2,284,888 A | 6/1942 | Arneil, Jr. |
| 2,324,702 A | 7/1943 | Hoffman et al. |
| 2,345,489 A | 3/1944 | Lord |
| 2,495,568 A | 1/1950 | Coel |
| 3,766,666 A | 10/1973 | Stroop |
| 3,775,865 A | 12/1973 | Rowan |
| 3,789,518 A | 2/1974 | Chase |
| 3,921,311 A | 11/1975 | Beasley et al. |
| 3,991,490 A | 11/1976 | Markman |
| 4,001,951 A | 1/1977 | Fasse |
| 4,001,952 A | 1/1977 | Kleppinger |
| 4,321,047 A | 3/1982 | Landis |
| 4,323,350 A | 4/1982 | Bowden, Jr. |
| 4,332,569 A | 6/1982 | Burbank |
| 4,371,345 A | 2/1983 | Palmer et al. |
| 4,386,917 A | 6/1983 | Forrest |
| 4,459,113 A | 7/1984 | Boscaro Gatti et al. |
| 4,481,001 A | 11/1984 | Graham et al. |
| 4,596,528 A | 6/1986 | Lewis et al. |
| 4,726,772 A | 2/1988 | Amplatz |
| 4,737,109 A | 4/1988 | Abramson |
| 4,789,340 A | 12/1988 | Zikria |
| 4,832,978 A | 5/1989 | Lesser |
| 4,867,686 A | 9/1989 | Goldstein |
| 4,907,973 A | 3/1990 | Hon |
| 4,938,696 A | 7/1990 | Foster et al. |
| 4,940,412 A | 7/1990 | Blumenthal |
| 5,061,187 A | 10/1991 | Jerath |
| 5,083,962 A | 1/1992 | Pracas |
| 5,104,328 A | 4/1992 | Lounsbury |
| 5,149,270 A | 9/1992 | McKeown |
| 5,180,308 A | 1/1993 | Garito et al. |
| 5,230,630 A | 7/1993 | Burgett |
| 5,273,435 A | 12/1993 | Jacobson |
| 5,295,694 A | 3/1994 | Levin |
| 5,310,348 A | 5/1994 | Miller |
| 5,318,448 A | 6/1994 | Garito et al. |
| 5,320,537 A | 6/1994 | Watson |
| 5,358,408 A | 10/1994 | Medina |
| 5,368,487 A | 11/1994 | Medina |
| 5,380,207 A | 1/1995 | Siepser |
| 5,403,191 A | 4/1995 | Tuason |
| 5,425,644 A | 6/1995 | Szinicz |
| 5,425,731 A | 6/1995 | Daniel et al. |
| 5,472,345 A | 12/1995 | Eggert |
| 5,518,406 A | 5/1996 | Waters |
| 5,518,407 A | 5/1996 | Greenfield et al. |
| 5,520,633 A | 5/1996 | Costin |
| 5,541,304 A | 7/1996 | Thompson |
| 5,620,326 A | 4/1997 | Younker |
| 5,720,742 A | 2/1998 | Zacharias |
| 5,722,836 A | 3/1998 | Younker |
| 5,727,948 A | 3/1998 | Jordan |
| 5,743,730 A | 4/1998 | Clester et al. |
| 5,762,458 A | 6/1998 | Wang et al. |
| 5,769,640 A | 6/1998 | Jacobus et al. |
| 5,775,916 A | 7/1998 | Cooper et al. |
| 5,785,531 A | 7/1998 | Leung |
| 5,800,178 A | 9/1998 | Gillio |
| 5,803,746 A | 9/1998 | Barrie et al. |
| 5,807,378 A | 9/1998 | Jensen et al. |
| 5,810,880 A | 9/1998 | Jensen et al. |
| 5,814,038 A | 9/1998 | Jensen et al. |
| 5,850,033 A | 12/1998 | Mirzeabasov et al. |
| 5,855,583 A | 1/1999 | Wang et al. |
| 5,873,732 A | 2/1999 | Hasson |
| 5,873,863 A | 2/1999 | Komlosi |
| 5,908,302 A | 6/1999 | Goldfarb |
| 5,947,743 A | 9/1999 | Hasson |
| 5,951,301 A | 9/1999 | Younker |
| 6,080,181 A | 6/2000 | Jensen et al. |
| 6,083,008 A | 7/2000 | Yamada et al. |
| 6,113,395 A | 9/2000 | Hon |
| 6,234,804 B1 | 5/2001 | Yong |
| 6,271,278 B1 | 8/2001 | Park et al. |
| 6,336,812 B1 | 1/2002 | Cooper et al. |
| 6,398,557 B1 | 6/2002 | Hoballah |
| 6,413,264 B1 | 7/2002 | Jensen et al. |
| 6,474,993 B1 | 11/2002 | Grund et al. |
| 6,485,308 B1 | 11/2002 | Goldstein |
| 6,488,507 B1 | 12/2002 | Stoloff et al. |
| 6,497,902 B1 | 12/2002 | Ma |
| 6,511,325 B1 | 1/2003 | Lalka et al. |
| 6,517,354 B1 | 2/2003 | Levy |
| 6,568,941 B1 | 5/2003 | Goldstein |
| 6,589,057 B1 | 7/2003 | Keenan et al. |
| 6,620,174 B2 | 9/2003 | Jensen et al. |
| 6,654,000 B2 | 11/2003 | Rosenberg |
| 6,659,776 B1 | 12/2003 | Aumann et al. |
| 6,773,263 B2 | 8/2004 | Nicholls et al. |
| 6,780,016 B1 | 8/2004 | Toly |
| 6,817,973 B2 | 11/2004 | Merril et al. |
| 6,820,025 B2 | 11/2004 | Bachmann et al. |
| 6,854,976 B1 | 2/2005 | Suhr |
| 6,857,878 B1 | 2/2005 | Chosack et al. |
| 6,863,536 B1 | 3/2005 | Fisher et al. |
| 6,866,514 B2 | 3/2005 | Von Roeschlaub et al. |
| 6,887,082 B2 | 5/2005 | Shun |
| 6,929,481 B1 | 8/2005 | Alexander et al. |
| 6,939,138 B2 | 9/2005 | Chosack et al. |
| 6,950,025 B1 | 9/2005 | Nguyen |
| 6,960,617 B2 | 11/2005 | Omidian et al. |
| 6,997,719 B2 | 2/2006 | Wellman et al. |
| 7,008,232 B2 | 3/2006 | Brassel |
| 7,018,327 B1 | 3/2006 | Conti |
| 7,025,064 B2 | 4/2006 | Wang et al. |
| 7,056,123 B2 | 6/2006 | Gregorio et al. |
| 7,080,984 B1 | 7/2006 | Cohen |
| 7,118,582 B1 | 10/2006 | Wang et al. |
| 7,255,565 B2 | 8/2007 | Keegan |
| 7,269,532 B2 | 9/2007 | David et al. |
| 7,272,766 B2 | 9/2007 | Sakezles |
| 7,300,450 B2 | 11/2007 | Vleugels et al. |
| 7,364,582 B2 | 4/2008 | Lee |
| 7,404,716 B2 | 7/2008 | Gregorio et al. |
| 7,419,376 B2 | 9/2008 | Sarvazyan et al. |
| 7,427,199 B2 | 9/2008 | Sakezles |
| 7,431,189 B2 | 10/2008 | Shelton, IV et al. |
| 7,441,684 B2 | 10/2008 | Shelton, IV et al. |
| 7,465,168 B2 | 12/2008 | Allen et al. |
| 7,467,075 B2 | 12/2008 | Humphries et al. |
| 7,544,062 B1 | 6/2009 | Hauschild et al. |
| 7,549,866 B2 | 6/2009 | Cohen et al. |
| 7,553,159 B1 | 6/2009 | Arnal et al. |
| 7,575,434 B2 | 8/2009 | Palakodeti |
| 7,594,815 B2 | 9/2009 | Toly |

(56) References Cited

U.S. PATENT DOCUMENTS

| | | |
|---|---|---|
| 7,621,749 B2 | 11/2009 | Munday |
| 7,646,901 B2 | 1/2010 | Murphy et al. |
| 7,648,367 B1 | 1/2010 | Makower et al. |
| 7,648,513 B2 | 1/2010 | Green et al. |
| 7,651,332 B2 | 1/2010 | Dupuis et al. |
| 7,677,897 B2 | 3/2010 | Sakezles |
| 7,775,916 B1 | 8/2010 | Mahoney |
| 7,780,451 B2 | 8/2010 | Willobee et al. |
| 7,802,990 B2 | 9/2010 | Korndorffer et al. |
| 7,803,151 B2 | 9/2010 | Whitman |
| 7,806,696 B2 | 10/2010 | Alexander et al. |
| 7,819,799 B2 | 10/2010 | Merril et al. |
| 7,833,018 B2 | 11/2010 | Alexander et al. |
| 7,837,473 B2 | 11/2010 | Koh |
| 7,850,454 B2 | 12/2010 | Toly |
| 7,850,456 B2 | 12/2010 | Chosack et al. |
| 7,854,612 B2 | 12/2010 | Frassica et al. |
| 7,857,626 B2 | 12/2010 | Toly |
| 7,866,983 B2 | 1/2011 | Hemphill et al. |
| 7,931,470 B2 | 4/2011 | Alexander et al. |
| 7,931,471 B2 | 4/2011 | Senagore et al. |
| 7,988,992 B2 | 8/2011 | Omidian et al. |
| 7,993,140 B2 | 8/2011 | Sakezles |
| 7,997,903 B2 | 8/2011 | Hasson et al. |
| 8,007,281 B2 | 8/2011 | Toly |
| 8,007,282 B2 | 8/2011 | Gregorio et al. |
| 8,016,818 B2 | 9/2011 | Ellis et al. |
| 8,017,107 B2 | 9/2011 | Thomas et al. |
| 8,021,162 B2 | 9/2011 | Sui |
| 8,048,088 B2 | 11/2011 | Green et al. |
| 8,083,691 B2 | 12/2011 | Goldenberg et al. |
| 8,116,847 B2 | 2/2012 | Gattani et al. |
| 8,137,110 B2 | 3/2012 | Sakezles |
| 8,157,145 B2 | 4/2012 | Shelton, IV et al. |
| 8,197,464 B2 | 6/2012 | Krever et al. |
| 8,205,779 B2 | 6/2012 | Ma et al. |
| 8,221,129 B2 | 7/2012 | Parry et al. |
| 8,297,982 B2 | 10/2012 | Park et al. |
| 8,308,817 B2 | 11/2012 | Egilsson et al. |
| 8,323,028 B2 | 12/2012 | Matanhelia |
| 8,323,029 B2 | 12/2012 | Toly |
| 8,328,560 B2 | 12/2012 | Niblock et al. |
| 8,342,851 B1 | 1/2013 | Speeg et al. |
| 8,403,674 B2 | 3/2013 | Feygin et al. |
| 8,403,675 B2 | 3/2013 | Stoianovici et al. |
| 8,403,676 B2 | 3/2013 | Frassica et al. |
| 8,408,920 B2 | 4/2013 | Speller |
| 8,425,234 B2 | 4/2013 | Sakezles |
| 8,439,687 B1 | 5/2013 | Morriss et al. |
| 8,442,621 B2 | 5/2013 | Gorek et al. |
| 8,454,368 B2 | 6/2013 | Ault et al. |
| 8,459,094 B2 | 6/2013 | Yanni |
| 8,459,520 B2 | 6/2013 | Giordano et al. |
| 8,460,002 B2 | 6/2013 | Wang et al. |
| 8,465,771 B2 | 6/2013 | Wan et al. |
| 8,469,715 B2 | 6/2013 | Ambrozio |
| 8,469,716 B2 | 6/2013 | Fedotov et al. |
| 8,480,407 B2 | 7/2013 | Campbell et al. |
| 8,480,408 B2 | 7/2013 | Ishii et al. |
| 8,491,309 B2 | 7/2013 | Parry et al. |
| 8,500,753 B2 | 8/2013 | Green et al. |
| 8,512,044 B2 | 8/2013 | Sakezles |
| 8,517,243 B2 | 8/2013 | Giordano et al. |
| 8,521,252 B2 | 8/2013 | Diez |
| 8,535,062 B2 | 9/2013 | Nguyen |
| 8,544,711 B2 | 10/2013 | Ma et al. |
| 8,556,635 B2 | 10/2013 | Toly |
| 8,608,483 B2 | 12/2013 | Trotta et al. |
| 8,613,621 B2 | 12/2013 | Henderickson et al. |
| 8,636,520 B2 | 1/2014 | Iwasaki et al. |
| D699,297 S | 2/2014 | Bahsooun et al. |
| 8,641,423 B2 | 2/2014 | Gumkowski |
| 8,647,125 B2 | 2/2014 | Johns et al. |
| 8,678,831 B2 | 3/2014 | Trotta et al. |
| 8,679,279 B2 | 3/2014 | Thompson et al. |
| 8,696,363 B2 | 4/2014 | Gray et al. |
| 8,708,213 B2 | 4/2014 | Shelton, IV et al. |
| 8,708,707 B2 | 4/2014 | Hendrickson et al. |
| 8,764,449 B2 | 7/2014 | Rios et al. |
| 8,764,452 B2 | 7/2014 | Pravong et al. |
| 8,800,839 B2 | 8/2014 | Beetel |
| 8,801,437 B2 | 8/2014 | Mousques |
| 8,801,438 B2 | 8/2014 | Sakezles |
| 8,807,414 B2 | 8/2014 | Ross et al. |
| 8,808,004 B2 | 8/2014 | Misawa et al. |
| 8,808,311 B2 | 8/2014 | Heinrich et al. |
| 8,814,573 B2 | 8/2014 | Nguyen |
| 8,827,988 B2 | 9/2014 | Belson et al. |
| 8,840,628 B2 | 9/2014 | Green et al. |
| 8,870,576 B2 | 10/2014 | Millon et al. |
| 8,888,498 B2 | 11/2014 | Bisaillon et al. |
| 8,893,946 B2 | 11/2014 | Boudreaux et al. |
| 8,911,238 B2 | 12/2014 | Forsythe |
| 8,915,742 B2 | 12/2014 | Hendrickson et al. |
| 8,945,095 B2 | 2/2015 | Blumenkranz et al. |
| 8,961,190 B2 | 2/2015 | Hart et al. |
| 8,966,954 B2 | 3/2015 | Ni et al. |
| 8,968,003 B2 | 3/2015 | Hendrickson et al. |
| 9,008,989 B2 | 4/2015 | Wilson et al. |
| 9,017,080 B1 | 4/2015 | Placik |
| 9,026,247 B2 | 5/2015 | White |
| 9,050,201 B2 | 6/2015 | Egilsson et al. |
| 9,056,126 B2 | 6/2015 | Hersel et al. |
| 9,070,306 B2 | 6/2015 | Rappel et al. |
| 9,087,458 B2 | 7/2015 | Shim et al. |
| 9,096,744 B2 | 8/2015 | Wan et al. |
| 9,117,377 B2 | 8/2015 | Shim et al. |
| 9,119,572 B2 | 9/2015 | Gorek et al. |
| 9,123,261 B2 | 9/2015 | Lowe |
| 9,129,054 B2 | 9/2015 | Nawana et al. |
| 9,196,176 B2 | 11/2015 | Hager et al. |
| 9,226,799 B2 | 1/2016 | Lightcap et al. |
| 9,257,055 B2 | 2/2016 | Endo et al. |
| 9,265,587 B2 | 2/2016 | Vancamberg et al. |
| 9,295,468 B2 | 3/2016 | Heinrich et al. |
| 9,351,714 B2 | 5/2016 | Ross et al. |
| 9,336,694 B2 | 6/2016 | Shim et al. |
| 9,358,682 B2 | 6/2016 | Ruiz Morales |
| 9,364,224 B2 | 6/2016 | Nicholas et al. |
| 9,364,279 B2 | 6/2016 | Houser et al. |
| 9,370,361 B2 | 6/2016 | Viola et al. |
| 9,373,270 B2 | 6/2016 | Miyazaki |
| 9,387,276 B2 | 7/2016 | Sun et al. |
| 9,427,496 B2 | 8/2016 | Sun et al. |
| 9,439,649 B2 | 9/2016 | Shelton, IV et al. |
| 9,439,733 B2 | 9/2016 | Ha et al. |
| 9,449,532 B2 | 9/2016 | Black et al. |
| 9,468,438 B2 | 10/2016 | Baber et al. |
| 2001/0019818 A1 | 9/2001 | Yong |
| 2002/0168619 A1 | 11/2002 | Provenza |
| 2003/0031993 A1 | 2/2003 | Pugh |
| 2003/0091967 A1 | 5/2003 | Chosack et al. |
| 2003/0176770 A1 | 9/2003 | Merril et al. |
| 2004/0005423 A1 | 1/2004 | Dalton et al. |
| 2004/0126746 A1 | 7/2004 | Toly |
| 2004/0248072 A1 | 12/2004 | Gray et al. |
| 2005/0008997 A1 | 1/2005 | Herman |
| 2005/0026125 A1 | 2/2005 | Toly |
| 2005/0064378 A1 | 3/2005 | Toly |
| 2005/0084833 A1 | 4/2005 | Lacey et al. |
| 2005/0131390 A1 | 6/2005 | Heinrich et al. |
| 2005/0142525 A1 | 6/2005 | Cotin et al. |
| 2005/0192595 A1 | 9/2005 | Green et al. |
| 2005/0196739 A1 | 9/2005 | Moriyama |
| 2005/0196740 A1 | 9/2005 | Moriyama |
| 2005/0214727 A1 | 9/2005 | Stoianovici et al. |
| 2006/0046235 A1 | 3/2006 | Alexander et al. |
| 2006/0232664 A1 | 10/2006 | Toly |
| 2006/0252019 A1 | 11/2006 | Burkitt et al. |
| 2006/0275741 A1 | 12/2006 | Chewning et al. |
| 2007/0074584 A1 | 4/2007 | Talarico et al. |
| 2007/0077544 A1 | 4/2007 | Lemperle et al. |
| 2007/0078484 A1 | 4/2007 | Talarico et al. |
| 2007/0148626 A1 | 6/2007 | Ikeda |

(56) References Cited

U.S. PATENT DOCUMENTS

| | | |
|---|---|---|
| 2007/0166682 A1 | 7/2007 | Yarin et al. |
| 2007/0197895 A1 | 8/2007 | Nycz et al. |
| 2007/0225734 A1 | 9/2007 | Bell et al. |
| 2007/0238081 A1 | 10/2007 | Koh |
| 2007/0275359 A1 | 11/2007 | Rotnes et al. |
| 2008/0032272 A1 | 2/2008 | Palakodeti |
| 2008/0032273 A1 | 2/2008 | Macnamara et al. |
| 2008/0052034 A1 | 2/2008 | David et al. |
| 2008/0064017 A1 | 3/2008 | Grundmeyer, III |
| 2008/0076101 A1 | 3/2008 | Hyde et al. |
| 2008/0097501 A1 | 4/2008 | Blier |
| 2008/0108869 A1 | 5/2008 | Sanders et al. |
| 2008/0187895 A1 | 8/2008 | Sakezles |
| 2008/0188948 A1 | 8/2008 | Flatt |
| 2008/0299529 A1 | 12/2008 | Schaller |
| 2008/0317818 A1 | 12/2008 | Griffith et al. |
| 2009/0068627 A1 | 3/2009 | Toly |
| 2009/0142739 A1 | 6/2009 | Wang et al. |
| 2009/0142741 A1 | 6/2009 | Ault et al. |
| 2009/0143642 A1 | 6/2009 | Takahashi et al. |
| 2009/0176196 A1 | 7/2009 | Niblock et al. |
| 2009/0187079 A1 | 7/2009 | Albrecht et al. |
| 2009/0246747 A1 | 10/2009 | Buckman, Jr. |
| 2009/0298034 A1 | 12/2009 | Parry et al. |
| 2009/0314550 A1 | 12/2009 | Layton |
| 2010/0047752 A1 | 2/2010 | Chan et al. |
| 2010/0094312 A1 | 4/2010 | Ruiz Morales et al. |
| 2010/0099067 A1 | 4/2010 | Agro |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2010/0167254 A1 | 7/2010 | Nguyen |
| 2010/0094730 A1 | 8/2010 | Di Betta et al. |
| 2010/0196867 A1 | 8/2010 | Geerligs et al. |
| 2010/0204713 A1 | 8/2010 | Ruiz Morales |
| 2010/0209899 A1 | 8/2010 | Park |
| 2010/0248200 A1 | 9/2010 | Ladak |
| 2010/0258611 A1 | 10/2010 | Smith et al. |
| 2010/0273136 A1 | 10/2010 | Kandasami et al. |
| 2010/0279263 A1 | 11/2010 | Duryea |
| 2010/0285094 A1 | 11/2010 | Gupta |
| 2010/0324541 A1 | 12/2010 | Whitman |
| 2011/0020779 A1 | 1/2011 | Hannaford et al. |
| 2011/0046637 A1 | 2/2011 | Patel et al. |
| 2011/0046659 A1 | 2/2011 | Ramstein et al. |
| 2011/0087238 A1 | 4/2011 | Wang et al. |
| 2011/0091855 A1 | 4/2011 | Miyazaki |
| 2011/0137337 A1 | 6/2011 | van den Dool et al. |
| 2011/0200976 A1 | 8/2011 | Hou et al. |
| 2011/0207104 A1 | 8/2011 | Trotta |
| 2011/0218550 A1 | 9/2011 | Ma |
| 2011/0244436 A1 | 10/2011 | Campo |
| 2011/0269109 A2 | 11/2011 | Miyazaki |
| 2011/0281251 A1 | 11/2011 | Mousques |
| 2011/0301620 A1 | 12/2011 | Di Betta et al. |
| 2012/0015337 A1 | 1/2012 | Hendrickson et al. |
| 2012/0015339 A1 | 1/2012 | Hendrickson et al. |
| 2012/0016362 A1 | 1/2012 | Heinrich et al. |
| 2012/0028231 A1 | 2/2012 | Misawa et al. |
| 2012/0045743 A1 | 2/2012 | Okano et al. |
| 2012/0065632 A1 | 3/2012 | Shadduck |
| 2012/0082970 A1 | 4/2012 | Pravong et al. |
| 2012/0100217 A1 | 4/2012 | Green et al. |
| 2012/0115117 A1 | 5/2012 | Marshall |
| 2012/0115118 A1 | 5/2012 | Marshall |
| 2012/0116391 A1 | 5/2012 | Houser et al. |
| 2012/0148994 A1 | 6/2012 | Hori et al. |
| 2012/0164616 A1 | 6/2012 | Endo et al. |
| 2012/0165866 A1 | 6/2012 | Kaiser et al. |
| 2012/0172873 A1 | 7/2012 | Artale et al. |
| 2012/0179072 A1 | 7/2012 | Kegreiss |
| 2012/0202180 A1 | 8/2012 | Stock et al. |
| 2012/0264096 A1 | 10/2012 | Taylor et al. |
| 2012/0264097 A1 | 10/2012 | Newcott et al. |
| 2012/0282583 A1 | 11/2012 | Thaler et al. |
| 2012/0282584 A1 | 11/2012 | Millon et al. |
| 2012/0283707 A1 | 11/2012 | Giordano et al. |
| 2012/0288839 A1 | 11/2012 | Crabtree |
| 2012/0308977 A1 | 12/2012 | Tortola |
| 2013/0087597 A1 | 4/2013 | Shelton, IV et al. |
| 2013/0101973 A1 | 4/2013 | Hoke et al. |
| 2013/0105552 A1 | 5/2013 | Weir et al. |
| 2013/0116668 A1 | 5/2013 | Shelton, IV et al. |
| 2013/0157240 A1 | 6/2013 | Hart et al. |
| 2013/0171288 A1 | 7/2013 | Harders |
| 2013/0177890 A1 | 7/2013 | Sakezles |
| 2013/0192741 A1 | 8/2013 | Trotta et al. |
| 2013/0218166 A1 | 8/2013 | Elmore |
| 2013/0224709 A1 | 8/2013 | Riojas et al. |
| 2013/0245681 A1 | 9/2013 | Straehnz et al. |
| 2013/0253480 A1 | 9/2013 | Kimball et al. |
| 2013/0267876 A1 | 10/2013 | Leckenby et al. |
| 2013/0282038 A1 | 10/2013 | Dannaher et al. |
| 2013/0288216 A1 | 10/2013 | Parry, Jr. et al. |
| 2013/0302771 A1 | 11/2013 | Alderete |
| 2013/0324991 A1 | 12/2013 | Clem et al. |
| 2013/0324999 A1 | 12/2013 | Price et al. |
| 2014/0011172 A1 | 1/2014 | Lowe |
| 2014/0017651 A1 | 1/2014 | Sugimoto et al. |
| 2014/0030682 A1 | 1/2014 | Thilenius |
| 2014/0038151 A1 | 2/2014 | Hart |
| 2014/0051049 A1 | 2/2014 | Jarc et al. |
| 2014/0072941 A1 | 3/2014 | Hendrickson et al. |
| 2014/0087345 A1 | 3/2014 | Breslin et al. |
| 2014/0087346 A1 | 3/2014 | Breslin et al. |
| 2014/0087347 A1 | 3/2014 | Tracy et al. |
| 2014/0087348 A1* | 3/2014 | Tracy .................. G09B 23/30 434/272 |
| 2014/0088413 A1 | 3/2014 | Von Bucsh et al. |
| 2014/0093852 A1 | 4/2014 | Poulsen et al. |
| 2014/0093854 A1 | 4/2014 | Poulsen et al. |
| 2014/0099858 A1 | 4/2014 | Hernandez |
| 2014/0106328 A1 | 4/2014 | Loor |
| 2014/0107471 A1 | 4/2014 | Haider et al. |
| 2014/0156002 A1 | 6/2014 | Thompson et al. |
| 2014/0162016 A1 | 6/2014 | Matsui et al. |
| 2014/0163515 A1* | 6/2014 | Hyman .................. A61M 25/02 604/500 |
| 2014/0170623 A1 | 6/2014 | Jarstad et al. |
| 2014/0186809 A1 | 7/2014 | Hendrickson et al. |
| 2014/0187855 A1 | 7/2014 | Nagale et al. |
| 2014/0200561 A1 | 7/2014 | Ingmanson et al. |
| 2014/0212861 A1 | 7/2014 | Romano |
| 2014/0220527 A1 | 8/2014 | Li et al. |
| 2014/0220530 A1 | 8/2014 | Merkle et al. |
| 2014/0220532 A1 | 8/2014 | Ghez et al. |
| 2014/0242564 A1 | 8/2014 | Pravong et al. |
| 2014/0246479 A1 | 9/2014 | Baber et al. |
| 2014/0248596 A1 | 9/2014 | Hart et al. |
| 2014/0263538 A1 | 9/2014 | Leimbach et al. |
| 2014/0272878 A1 | 9/2014 | Shim et al. |
| 2014/0272879 A1 | 9/2014 | Shim et al. |
| 2014/0275795 A1 | 9/2014 | Little et al. |
| 2014/0275981 A1 | 9/2014 | Selover et al. |
| 2014/0277017 A1 | 9/2014 | Leimbach et al. |
| 2014/0303643 A1 | 10/2014 | Ha et al. |
| 2014/0303646 A1 | 10/2014 | Morgan et al. |
| 2014/0303660 A1 | 10/2014 | Boyden et al. |
| 2014/0308643 A1 | 10/2014 | Trotta et al. |
| 2014/0342334 A1 | 11/2014 | Black et al. |
| 2014/0349266 A1 | 11/2014 | Choi |
| 2014/0350530 A1 | 11/2014 | Ross et al. |
| 2014/0357977 A1 | 12/2014 | Zhou |
| 2014/0370477 A1 | 12/2014 | Black et al. |
| 2014/0371761 A1 | 12/2014 | Juanpera |
| 2014/0378995 A1 | 12/2014 | Kumar et al. |
| 2015/0031008 A1 | 1/2015 | Black et al. |
| 2015/0037773 A1 | 2/2015 | Quirarte Catano |
| 2015/0038613 A1 | 2/2015 | Sun et al. |
| 2015/0076207 A1 | 3/2015 | Boudreaux et al. |
| 2015/0086955 A1 | 3/2015 | Poniatowski et al. |
| 2015/0132732 A1 | 5/2015 | Hart et al. |
| 2015/0132733 A1 | 5/2015 | Garvik et al. |

(56) References Cited

U.S. PATENT DOCUMENTS

| | | | |
|---|---|---|---|
| 2015/0135832 | A1 | 5/2015 | Blumenkranz et al. |
| 2015/0148660 | A1 | 5/2015 | Weiss et al. |
| 2015/0164598 | A1 | 6/2015 | Blumenkranz et al. |
| 2015/0187229 | A1 | 7/2015 | Wachli et al. |
| 2015/0194075 | A1 | 7/2015 | Rappel et al. |
| 2015/0202299 | A1 | 7/2015 | Burdick et al. |
| 2015/0209035 | A1 | 7/2015 | Zemlock |
| 2015/0209059 | A1 | 7/2015 | Trees et al. |
| 2015/0209573 | A1 | 7/2015 | Hibner et al. |
| 2015/0228206 | A1 | 8/2015 | Shim et al. |
| 2015/0262511 | A1 | 9/2015 | Lin et al. |
| 2015/0265431 | A1 | 9/2015 | Egilsson et al. |
| 2015/0272571 | A1 | 10/2015 | Leimbach et al. |
| 2015/0272574 | A1 | 10/2015 | Leimbach et al. |
| 2015/0272580 | A1 | 10/2015 | Leimbach et al. |
| 2015/0272581 | A1 | 10/2015 | Leimbach et al. |
| 2015/0272583 | A1 | 10/2015 | Leimbach et al. |
| 2015/0272604 | A1 | 10/2015 | Chowaniec et al. |
| 2015/0332609 | A1 | 11/2015 | Alexander |
| 2015/0358426 | A1 | 12/2015 | Kimball et al. |
| 2015/0371560 | A1 | 12/2015 | Lowe |
| 2015/0374378 | A1 | 12/2015 | Giordano et al. |
| 2015/0374449 | A1 | 12/2015 | Chowaniec et al. |
| 2016/0000437 | A1 | 1/2016 | Giordano et al. |
| 2016/0022374 | A1 | 1/2016 | Haider et al. |
| 2016/0030240 | A1 | 2/2016 | Gonenc et al. |
| 2016/0031091 | A1 | 2/2016 | Popovic et al. |
| 2016/0058534 | A1 | 3/2016 | Derwin et al. |
| 2016/0066909 | A1 | 3/2016 | Baber et al. |
| 2016/0070436 | A1 | 3/2016 | Thomas et al. |
| 2016/0073928 | A1 | 3/2016 | Soper et al. |
| 2016/0074103 | A1 | 3/2016 | Sartor |
| 2016/0098933 | A1 | 4/2016 | Reiley et al. |
| 2016/0104394 | A1 | 4/2016 | Miyazaki |
| 2016/0117956 | A1 | 4/2016 | Larsson et al. |
| 2016/0125762 | A1 | 5/2016 | Becker et al. |
| 2016/0133158 | A1 | 5/2016 | Sui et al. |
| 2016/0140876 | A1 | 5/2016 | Jabbour et al. |
| 2016/0194378 | A1 | 7/2016 | Cass et al. |
| 2016/0199059 | A1 | 7/2016 | Shelton, IV et al. |
| 2016/0220150 | A1 | 8/2016 | Sharonov |
| 2016/0220314 | A1 | 8/2016 | Huelman et al. |
| 2016/0225288 | A1 | 8/2016 | East et al. |
| 2016/0232819 | A1 | 8/2016 | Hofstetter et al. |
| 2016/0235494 | A1 | 8/2016 | Shelton, IV et al. |
| 2016/0256187 | A1 | 9/2016 | Shelton, IV et al. |
| 2016/0256229 | A1 | 9/2016 | Morgan et al. |
| 2016/0262736 | A1 | 9/2016 | Ross et al. |
| 2016/0262745 | A1 | 9/2016 | Morgan et al. |
| 2016/0293055 | A1 | 10/2016 | Hofstetter |
| 2016/0296144 | A1 | 10/2016 | Gaddam et al. |

FOREIGN PATENT DOCUMENTS

| | | |
|---|---|---|
| CN | 2751372 Y | 1/2006 |
| CN | 2909427 Y | 6/2007 |
| CN | 101313842 A | 12/2008 |
| CN | 101528780 A | 9/2009 |
| CN | 201364679 Y | 12/2009 |
| CN | 201955979 U | 8/2011 |
| CN | 102458496 A | 5/2012 |
| CN | 202443680 U | 9/2012 |
| CN | 202563792 U | 11/2012 |
| CN | 202601055 U | 12/2012 |
| CN | 202694651 U | 1/2013 |
| CN | 103050040 A | 4/2013 |
| CN | 203013103 U | 6/2013 |
| CN | 203038549 U | 7/2013 |
| CN | 203338651 U | 12/2013 |
| CN | 203397593 U | 1/2014 |
| CN | 203562128 U | 4/2014 |
| CN | 102596275 B | 6/2014 |
| CN | 103845757 A | 6/2014 |
| CN | 103886797 A | 6/2014 |
| CN | 103396562 B | 7/2015 |
| CN | 105194740 A | 12/2015 |
| CN | 105504166 A | 4/2016 |
| DE | 9102218 U1 | 5/1991 |
| DE | 41 05 892 A1 | 8/1992 |
| DE | 93 20 422 U1 | 6/1994 |
| DE | 44 14 832 A1 | 11/1995 |
| DE | 19716341 A1 | 9/2000 |
| EP | 1 024 173 A1 | 8/2000 |
| EP | 0 990 227 B1 | 4/2002 |
| EP | 1 609 431 A1 | 12/2005 |
| EP | 0 870 292 B1 | 7/2008 |
| EP | 2 068 295 A2 | 6/2009 |
| EP | 2 218 570 A1 | 8/2010 |
| FR | 2 691 826 A1 | 12/1993 |
| FR | 2 917 876 A1 | 12/2008 |
| GB | 2488994 A | 9/2012 |
| JP | 10 211160 A | 8/1998 |
| JP | 2001005378 A | 1/2001 |
| JP | 2006187566 A | 7/2006 |
| JP | 2009063787 A | 3/2009 |
| JP | 2009236963 A | 10/2009 |
| JP | 3162161 U | 8/2010 |
| JP | 2011113056 A | 6/2011 |
| JP | 2013127496 A | 6/2013 |
| KR | 101231565 B1 | 2/2013 |
| MX | PA 02004422 A | 11/2003 |
| PT | 106230 | 9/2013 |
| WO | WO 1994/06109 A1 | 3/1994 |
| WO | WO 1996/042076 A1 | 12/1996 |
| WO | WO 1998/58358 A1 | 12/1998 |
| WO | WO 1999/01074 A1 | 1/1999 |
| WO | WO 2000/36577 A1 | 6/2000 |
| WO | WO 2002/38039 A2 | 5/2002 |
| WO | WO 2002/038039 A3 | 5/2002 |
| WO | WO 2004/032095 A1 | 4/2004 |
| WO | WO 2004/082486 A1 | 9/2004 |
| WO | WO 2005/071639 A1 | 8/2005 |
| WO | WO 2005/083653 A1 | 9/2005 |
| WO | WO 2006/083963 A2 | 8/2006 |
| WO | WO 2007/068360 A1 | 6/2007 |
| WO | WO 2008/021720 A2 | 2/2008 |
| WO | WO 2008/103383 A1 | 8/2008 |
| WO | WO 2009/000939 A1 | 12/2008 |
| WO | WO 2009/089614 A1 | 7/2009 |
| WO | WO 2010/094730 A1 | 8/2010 |
| WO | WO 2011/035410 A1 | 3/2011 |
| WO | WO 2011/046606 A1 | 4/2011 |
| WO | WO 2011/127379 A2 | 10/2011 |
| WO | WO 2011/151304 A1 | 12/2011 |
| WO | WO 2012/149606 A1 | 11/2012 |
| WO | WO 2012/168287 A1 | 12/2012 |
| WO | WO 2012/175993 A1 | 12/2012 |
| WO | WO 2013/048978 A1 | 4/2013 |
| WO | WO 2013/103956 A1 | 7/2013 |
| WO | WO 2014/022815 A1 | 2/2014 |
| WO | WO 2014/093669 A1 | 6/2014 |
| WO | WO 2014/197793 A1 | 12/2014 |
| WO | WO 2015/148817 A1 | 10/2015 |
| WO | WO 2016/138528 A1 | 9/2016 |
| WO | WO 2016/183412 A1 | 11/2016 |
| WO | WO 2016/198238 A1 | 12/2016 |
| WO | WO 2016/201085 A1 | 12/2016 |
| WO | WO 2017/031214 A1 | 2/2017 |
| WO | WO 2017/042301 A1 | 3/2017 |

OTHER PUBLICATIONS

European Patent Office, Extended European Search Report for European Patent Application No. EP 22172093.1, titled "Hysterectomy Model," dated Jul. 20, 2022, 9 pgs.

Society of Laparoendoscopic Surgeons, "Future Technology Session: The Edge of Innovation in Surgery, Space, and Business," http://www.laparoscopytoday.com/endourology/page/2/ , Figure 1B: http://laparoscopy.blogs.com/laparoscopy_today/images/6-1/6-1VlaovicPicB.jpg , Sep. 5-8, 2007, 10 pgs.

European Patent Office, International Search Report for International Application No. PCT/US2011/053859 A3, dated Apr. 5, 2012, entitled "Portable Laparoscopic Trainer," 8 pgs.

(56) References Cited

OTHER PUBLICATIONS

European Patent Office, The International Search Report and Written Opinion for International Application No. PCT/US2012/60997, dated Mar. 7, 2013, entitled "Simulated Tissue Structure for Surgical Training," 8 pgs.
European Patent Office, The International Search Report and Written Opinion for International Application No. PCT/US2012/070971, entitled "Advanced Surgical Simulation," dated Mar. 18, 2013, 10 pgs.
Human Patient Simulator, Medical Education Technologies, Inc., http://www.meti.com (1999) all, printed Apr. 12, 2013, 24 pgs.
The International Bureau of WIPO, International Preliminary Report on Patentability and Written Opinion for International Application No. PCT/US2011/053859, titled "Portable Laparoscopic Trainer" dated Apr. 2, 2013, 9 pgs.
European Patent Office, The International Search Report and Written Opinion for International Application No. PCT/US2013/062363, entitled "Surgical Training Model for Laparoscopic Procedures," dated Jan. 22, 2014, 11 pgs.
European Patent Office, The International Search Report and Written Opinion for International Application No. PCT/US2013/061949, entitled "Surgical Training Model for Laparoscopic Procedures," dated Feb. 17, 2014, 7 pgs.
Anonymous: Realsim Systems—LTS2000, Sep. 4, 2005, pp. 1-2, XP055096193, Retrieved from the Internet: URL:https://web.archive.org/web/2005090403;3030/http://www.realsimsystems.com/exersizes.htm (retrieved on Jan. 14, 2014).
European Patent Office, The International Search Report and Written Opinion for International Application No. PCT/US2013/062269, entitled "Surgical Training Model for Transluminal Procedures," dated Feb. 17, 2014, 8 pgs.
European Patent Office, The International Search Report and Written Opinion for International Application No. PCT/US2013/061557, entitled "Surgical Training Model for Laparoscopic Procedures," dated Feb. 10, 2014, 9 pgs.
European Patent Office, The International Search Report and Written Opinion for International Application No. PCT/US2013/061728, entitled "Surgical Training Model for Laparoscopic Procedures," dated Oct. 18, 2013, 9 pgs.
Limps and Things, EP Guildford MATTU Hernia Trainer, http://limbsandthings.com/us/products/tep-guildford-mattu-hernia-trainer/, printed May 29, 2014, 11 pgs.
Simulab, Hernia Model, http://www.simulab.com/product/surgery/open/hernia model, printed printed May 29, 2014, 4 pgs.
McGill Laparoscopic Inguinal Hernia Simulator, Novel Low-Cost Simulator for Laparoscopic Inguinal Hernia Repair, Feb. 8, 2011, 1 pg.
University of Wisconsin-Madison Biomedical Engineering, Inguinal Hernia Model, http://bmedesign.engr.wisc.edu/projects/s10/hernia_model/, printed May 29, 2014, 62 pgs.
The International Bureau of WIPO, International Preliminary Report on Patentability for International Application No. PCT/US2012/070971, titled "Advanced Surgical Simulation" dated Jun. 24, 2014, 7 pgs.
European Patent Office, The International Search Report and Written Opinion of the International Searching Authority for International Application No. PCT/US2014/038195 titled "Hernia Model", dated Oct. 15, 2014, 20 pgs.
European Patent Office, The International Search Report and Written Opinion of the International Searching Authority for International Application No. PCT/US2014/048027 titled "First Entry Model", dated Oct. 17, 2014, 10 pgs.
The International Bureau of WIPO, International Preliminary Report on Patentability for International Application No. PCT/US2012/060997, titled "Simulated Tissue Structure For Surgical Training" dated Apr. 22, 2014, 6 pgs.
European Patent Office, The International Search Report and Written Opinion for International Application No. PCT/US2014/019840, entitled "Advanced Surgical Simulation Constructions and Methods," dated Jul. 4, 2014, 8 pgs.

Kurashima Y et al, "A tool for training and evaluation of Laparoscopic inguinal hernia repair; the Global Operative Assessment of Laparoscopic Skills-Groin Hernia" American Journal of Surgery, Paul Hoeber, New York, NY, US vol. 201, No. 1, Jan. 1, 2011, pp. 54-61 XP027558745.
European Patent Office, The International Search Report and Written Opinion for International Application No. PCT/US2014/042998, title; Gallbladder Model, dated Jan. 7, 2015, 20 pgs.
The International Bureau of WIPO, International Preliminary Report on Patentability, for PCT application No. PCT/US2013/053497, titled, Simulated Stapling and Energy Based Ligation for Surgical Training, dated Feb. 12, 2015, 6 pgs.
The International Bureau of WIPO, International Preliminary Report on Patentability for International Application No. PCT/US2013/062363, titled Surgical Training Model for Laparoscopic Procedures, dated Apr. 9, 2015, 9 pgs.
The International Bureau of WIPO, International Preliminary Report on Patentability for International Application No. PCT/US2013/062269, titled Surgical Training Model for Laparoscopic Procedures, dated Apr. 9, 2015, 6 pgs.
The International Bureau of WIPO, International Preliminary Report on Patentability for International Application No. PCT/US2013/061557, titled Surgical Training Model for Laparoscopic Procedures, dated Apr. 9, 2015, 6 pgs.
The International Bureau of WIPO, International Preliminary Report on Patentability for International Application No. PCT/US2013/061728, titled Surgical Training Model for Laparoscopic Procedures, dated Apr. 9, 2015, 7 pgs.
The International Bureau of WIPO, International Preliminary Report on Patentability for International Application No. PCT/US2013/061949, titled Surgical Training Model for Laparoscopic Procedures, dated Apr. 9, 2015, 6 pgs.
The International Bureau of WIPO, International Preliminary Report on Patentability for International Application No. PCT/US2014/019840, titled "Simulated Tissue Structure For Surgical Training" dated Sep. 11, 2015, 8 pgs.
European Patent Office, The International Search Report and Written Opinion for International Application No. PCT/US2015/020574, titled "Advanced First Entry Model for Surgical Simulation," dated Jun. 1, 2015, 12 pgs.
European Patent Office, The International Search Report and Written Opinion for International Application No. PCT/US2015/022774, entitled "Simulated Dissectible Tissue," dated Jun. 11, 2015, 13 pgs.
Anonymous: Silicone rubber—from Wikipedia, the free encyclopedia, pp. 1-6, XP055192375, Retrieved from the Internet: URL:http://en.wikipedia.org/w.index.php?title=Silicone_rubber&oldid=596456058 (retrieved on May 29, 2015).
Lamouche, et al., "Review of tissue simulating phantoms with controllable optical, mechanical and structural properties for use in optical coherence tomography," Biomedical Optics Express, Jun. 1, 2012, 18 pgs., vol. 3, No. 6.
The International Bureau of WIPO, International Preliminary Report on Patentability for International Application No. PCT/US2014/038195, titled "Hernia Model," dated Nov. 26, 2015, 16 pgs.
The International Bureau of WIPO, International Preliminary Report on Patentability for International Application No. PCT/US2014/042998, titled "Gallbladder Model," dated Dec. 30, 2015, 15 pgs.
European Patent Office, International Search Report and Written Opinion for International Application No. PCT/US2013/053497, titled "Simulated Stapling and Energy Based Ligation for Surgical Training," dated Nov. 5, 2013, 8 pgs.
The International Bureau of WIPO, International Preliminary Report on Patentability for International Application No. PCT/US2014/048027, titled "First Entry Model," dated Feb. 4, 2016, 8 pgs.
European Patent Office, International Search Report and Written Opinion for International Application No. PCT/US2015/059668, titled "Simulated Tissue Models and Methods," dated Apr. 26, 2016, 20 pgs.
Australian Patent Office, Patent Examination Report No. 1 for Australian Application No. 2012358851, titled "Advanced Surgical Simulation," dated May 26, 2016, 3 pgs.

(56) References Cited

OTHER PUBLICATIONS

Miyazaki Enterprises, "Miya Model Pelvic Surgery Training Model and Video," www.miyazakienterprises, printed Jul. 1, 2016, 1 pg.
European Patent Office, International Search Report and Written Opinion for International Application No. PCT/US2016/032292 titled "Synthetic Tissue Structures for Electrosurgical Training and Simulation," dated Jul. 14, 2016, 11 pgs.
European Patent Office, International Search Report and Written Opinion for International Application No. PCT/US2016/018697 titled "Simulated Tissue Structures and Methods," dated Jul. 14, 2016, 21 pgs.
European Patent Office, International Search Report and Written Opinion for International Application No. PCT/US2016/034591, titled "Surgical Training Model for Laparoscopic Procedures," dated Aug. 8, 2016, 18 pgs.
European Patent Office, The International Search Report and Written Opinion of the International Searching Authority for International Application No. PCT/US2016/036664 titled "Hysterectomy Model", dated Aug. 19, 2016, 15 pgs.
3D-MED Corporation, "Validated Training Course for Laparoscopic Skills," https://www.3-dmed.com/sites/default/files/product-additional/product-spec/Validated%20Training%20Course%20for%20Laparoscopic%20Skills.docx 3.pdf , printed Aug. 23, 2016, pp. 1-6.
3D-MED Corporation, "Loops and Wire #1," https://www.3-dmed.com/product/loops-and-wire-1 , printed Aug. 23, 2016, 4 pgs.
Barrier, et al., "A Novel and Inexpensive Vaginal Hysterectomy Simulatory," Simulation in Healthcare: The Journal of the Society for Simulation in Healthcare, vol. 7, No. 6, Dec. 1, 2012, pp. 374-379.
The International Bureau of WIPO, International Preliminary Report on Patentability for International Application No. PCT/US2015/020574, entitled "Advanced First Entry Model for Surgical Simulation," dated Sep. 22, 2016, 9 pgs.
European Patent Office, The International Search Report and Written Opinion of the International Searching Authority for International Application No. PCT/US2016/0043277 titled "Appendectomy Model", dated Oct. 4, 2016, 12 pgs.
The International Bureau of WIPO, International Preliminary Report on Patentability for International Application No. PCT/US2015/022774, titled "Simulated Dissectible Tissue," dated Oct. 6, 2016, 9 pgs.
European Patent Office, The International Search Report and Written Opinion of the International Searching Authority for International Application No. PCT/US2016/041852 titled "Simulated Dissectible Tissue", dated Oct. 13, 2016, 12 pgs.
European Patent Office, Invitation to Pay Additional Fees for International Application No. PCT/US2016/062669, titled "Simulated Dissectible Tissue", dated Feb. 10, 2017, 8 pgs.
European Patent Office, The International Search Report and Written Opinion of the International Searching Authority for International Application No. PCT/US2016/055148 titled "Hysterectomy Model", dated Feb. 28, 2017, 12 pgs.
European Patent Office, Examination Report for European Application No. 14733949.3 titled "Gallbladder Model," dated Dec. 21, 2016, 6 pgs.
European Patent Office, The International Search Report and Written Opinion of the International Searching Authority for International Application No. PCT/US2016/062669 titled "Simulated Dissectible Tissue," dated Apr. 5, 2017, 19 pgs.
European Patent Office, The International Search Report and Written Opinion of the International Searching Authority for International Application No. PCT/US2017/020389 titled "Simulated Tissue Cartridge", dated May 24, 2017, 13 pgs.
The International Bureau of WIPO, International Preliminary Report on Patentability and Written Opinion for International Application No. PCT/US2015/059668, entitled "Simulated Tissue Models and Methods," dated May 26, 2017, 16 pgs.
The International Bureau of WIPO, International Preliminary Report on Patentability for International Application No. PCT/US2016/018697, entitled "Simulated Tissue Structures and Methods," dated Aug. 31, 2017, 14 pgs.
The International Bureau of WIPO, International Preliminary Report on Patentability for International Application No. PCT/US2016/0032292, entitled "Synthetic Tissue Structures for Electrosurgical Training and Simulation," dated Nov. 23, 2017, 2017, 8 pgs.
The International Bureau of WIPO, International Preliminary Report on Patentability for International Application No. PCT/US2016/034591, entitled "Surgical Training Model for Laparoscopic Procedures," dated Dec. 7, 2017, 2017, 14 pgs.
The International Bureau of WIPO, International Preliminary Report on Patentability for International Application No. PCT/US2016/036664, entitled "Hysterectomy Model," dated Dec. 21, 2017, 10 pgs.
The International Bureau of WIPO, International Preliminary Report on Patentability for International Application No. PCT/US2016/041852, entitled "Simulated Dissectible Tissue," dated Jan. 25, 2018, 12 pgs.
European Patent Office, Extended European Search Report for European Patent Application No. EP 17202365.7, titled "Gallbladder Model", dated Jan. 31, 2018, 8 pgs.
The International Bureau of WIPO, International Preliminary Report on Patentability for International Application No. PCT/US2016/043277, entitled "Appendectomy Model," dated Feb. 1, 2018, 9 pgs.
The International Bureau of WIPO, International Preliminary Report on Patentability for International Application No. PCT/US2016/055148, entitled "Hysterectomy Model," dated Apr. 12, 2018, 12 pgs.
European Patent Office, The International Search Report and Written Opinion for International Application No. PCT/US2018/018895, entitled "Synthetic Tissue Structures for Electrosurgical Training and Simulation," dated May 17, 2018, 12 pgs.
The International Bureau of WIPO, International Preliminary Report on Patentability for International Application No. PCT/US2016/062669, entitled "Simulated Dissectible Tissue," dated May 31, 2018, 11 pgs.
European Patent Office, The International Search Report and Written Opinion for International Application No. PCT/US2018/018036, entitled "Laparoscopic Training System," dated Jun. 8, 2018, 13 pgs.
European Patent Office, The International Search Report and Written Opinion for International Application No. PCT/US2017/039113, entitled "Simulated Abdominal Wall," dated Aug. 7, 2017, 13 pgs.
European Patent Office, Extended European Search Report for European Patent Application No. EP 18177751.7, titled "Portable Laparoscopic Trainer," dated Jul. 13, 2018, 8 pgs.
European Patent Office, The International Search Report and Written Opinion for International Application No. PCT/US2018/034705, entitled "Laparoscopic Training System," dated Aug. 20, 2018, 14 pgs.
The International Bureau of WIPO, International Preliminary Report on Patentability for International Application No. PCT/US2017/020389, entitled "Simulated Tissue Cartridge," dated Sep. 13, 2018, 8 pgs.
European Patent Office, Extended European Search Report for European Patent Application No. EP 18184147.9, titled "First Entry Model," dated Nov. 7, 2018, 7 pgs.
The International Bureau of WIPO, International Preliminary Report on Patentability for International Application No. PCT/US2017/039113, entitled "Simulated Abdominal Wall," dated Jan. 10, 2019, 8 pgs.
European Patent Office, Extended European Search Report for European Patent Application No. EP 18210006.5, titled "Surgical Training Model for Laparoscopic Procedures," dated Jan. 21, 2019, 7 pgs.
European Patent Office, Extended European Search Report for European Patent Application No. EP 18207214.0, titled "Synthetic Tissue Structures for Electrosurgical Training and Simulation," dated Mar. 28, 2019, 6 pgs.

(56) References Cited

OTHER PUBLICATIONS

European Patent Office, Extended European Search Report for European Patent Application No. EP 18216002.8, titled "Surgical Training Model for Laparoscopic Procedures," dated Apr. 2, 2019, 6 pgs.
European Patent Office, Extended European Search Report for European Patent Application No. EP 18216005.1, titled "Surgical Training Model for Laparoscopic Procedures," dated Apr. 2, 2019, 7 pgs.
European Patent Office, Extended European Search Report for European Patent Application No. EP 19159065.2, titled "Simulated Tissue Structures and Methods," dated May 29, 2019, 8 pgs.
The International Bureau of WIPO, International Preliminary Report on Patentability for International Application No. PCT/US2018/018036, entitled "Laparoscopic Training System," dated Aug. 29, 2019, 8 pgs.
The International Bureau of WIPO, International Preliminary Report on Patentability for International Application No. PCT/US2018/018895, entitled "Synthetic Tissue Structures for Electrosurgical Training and Simulation," dated Sep. 6, 2019, 7 pgs.
European Patent Office, Extended European Search Report for European Patent Application No. EP 20153338.7, titled "Advanced Surgical Simulation Constructions and Methods," dated Mar. 5, 2020, 7 pgs.
European Patent Office, Extended European Search Report for European Patent Application No. EP 19215545.5, titled "Advanced First Entry Model for Surgical Simulation," dated Mar. 26, 2020, 8 pgs.
European Patent Office, Extended European Search Report for European Patent Application No. EP 20158500.7, titled "Surgical Training Device," dated May 14, 2020, 9 pgs.
"Surgical Female Pelvic Trainer (SFPT) with Advanced Surgical Uterus," Limbs & Things Limited, Issue 1, Jul. 31, 2003, URL:https://www.accuratesolutions.it/wp-content/uploads/2012/08/ Surgical_Female_Pelvic_Trainer_SFPT_with_Advanced_Uterus_Us er_Guide.pdf, retrieved Feb. 21, 2020, 2 pgs.
European Patent Office, Extended European Search Report for European Patent Application No. EP 20186713.2, titled "Simulated Dissectible Tissue," dated Nov. 10, 2020, 12 pgs.
European Patent Office, Extended European Search Report for European Patent Application No. 21159294.4, titled "Surgical Training Model for Laparoscopic Procedures," dated Apr. 5, 2021, 7 pgs.
Condino et al.; "How to build patient-specific synthetic abdominal anatomies. An innovative approach from physical toward hybrid surgical simulators," The International Journal of Medical Robotics and Computer Assisted Surgery, Apr. 27, 2011, vol. 7, No. 2, pp. 202-213.
Wilkes et al.; "Closed Incision Management with Negative Pressure Wound Therapy (CIM): Biomechanics," Surgical Innovation 19(1), URL:https://journals.sagepub.com/doi/pdf/10.1177/1553350611414920, Jan. 1, 2012, pp. 67-75.
European Patent Office, Extended European Search Report for European Patent Application No. EP 21182654.0, titled "Simulated Dissectible Tissue," dated Oct. 22, 2021, 13 pgs.
European Patent Office, Extended European Search Report for European Patent Application No. EP 21191452.8, titled "Advanced Surgical Simulation Constructions and Methods," dated Dec. 13, 2021, 8 pgs.
European Patent Office, Extended European Search Report for European Patent Application No. 22212824.1, titled "Surgical Training Model for Laparoscopic Procedures," dated Feb. 28, 2023, 20 pgs.
European Patent Office, Extended European Search Report for European Patent Application No. 22214865.2, titled "Gallbladder Model," dated Feb. 28, 2023, 18 pgs.

\* cited by examiner

SURGICAL TRAINING MODEL FOR LAPAROSCOPIC PROCEDURES

CROSS-REFERENCE TO RELATED APPLICATIONS

This application is a divisional of U.S. patent application Ser. No. 16/897,142 entitled "Surgical training model for laparoscopic procedures" filed on Jun. 9, 2020 which is a continuation of U.S. patent application Ser. No. 15/166,661 entitled "Surgical training model for laparoscopic procedures" filed on May 27, 2016, now U.S. Pat. No. 10,679,520 which claims priority to and benefit of U.S. Provisional Patent Application Ser. No. 62/318,902 entitled "Surgical training model for laparoscopic procedures" filed on Apr. 6, 2016, U.S. Provisional Patent Application Ser. No. 62/167,129 entitled "Surgical training model for laparoscopic procedures" filed on May 27, 2015, hereby incorporated herein by reference in their entireties.

FIELD OF THE INVENTION

This application is generally related to medical training devices, and in particular, to models for practicing suturing.

BACKGROUND OF THE INVENTION

Medical students as well as experienced doctors learning new surgical techniques must undergo extensive training before they are qualified to perform surgery on human patients. The training must teach proper techniques employing various medical devices for cutting, penetrating, clamping, grasping, stapling, cauterizing and suturing a variety of tissue types. The range of possibilities that a trainee may encounter is great. For example, different organs and patient anatomies and diseases are presented. The thickness and consistency of the various tissue layers will also vary from one part of the body to the next and from one patient to another. Different procedures demand different skills. Furthermore, the trainee must practice techniques in various anatomical environs that are influenced by factors such as the size and condition of the patient, the adjacent anatomical landscape and the types of targeted tissues and whether they are readily accessible or relatively inaccessible.

Numerous teaching aids, trainers, simulators and model organs are available for one or more aspects of surgical training. However, there is a need for models or simulated tissue elements that are likely to be encountered in and that can be used for practicing endoscopic and laparoscopic, minimally invasive surgical procedures. In laparoscopic surgery, a trocar or cannula is inserted to access a body cavity and to create a channel for the insertion of a camera such as a laparoscope. The camera provides a live video feed capturing images that are then displayed to the surgeon on one or more monitors. At least one additional small incision is made through which another trocar/cannula is inserted to create a pathway through which surgical instruments can be passed for performing procedures observed on the monitor. The targeted tissue location such as the abdomen is typically enlarged by delivering carbon dioxide gas to insufflate the body cavity and create a working space large enough to accommodate the scope and instruments used by the surgeon. The insufflation pressure in the tissue cavity is maintained by using specialized trocars. Laparoscopic surgery offers a number of advantages when compared with an open procedure. These advantages include reduced pain, reduced blood and shorter recovery times due to smaller incisions.

Laparoscopic or endoscopic minimally invasive surgery requires an increased level of skill compared to open surgery because the target tissue is not directly observed by the clinician. The target tissue is observed on monitors displaying a portion of the surgical site that is accessed through a small opening. Therefore, clinicians need to practice visually determining tissue planes, three-dimensional depth perception on a two-dimensional viewing screen, hand-to-hand transfer of instruments, suturing, precision cutting and tissue and instrument manipulation. Typically, models simulating a particular anatomy or procedure are placed in a simulated pelvic trainer where the anatomical model is obscured from direct visualization by the practitioner. Ports in the trainer are employed for passing instruments to practice techniques on the anatomical model hidden from direct visualization. Simulated pelvic trainers provide a functional, inexpensive and practical means to train surgeons and residents the basic skills and typical techniques used in laparoscopic surgery such as grasping, manipulating, cutting, tying knots, suturing, stapling, cauterizing as well as how to perform specific surgical procedures that utilized these basic skills. Simulated pelvic trainers are also effective sales tools for demonstrating medical devices required to perform these laparoscopic procedures.

One of the techniques mentioned above that requires practice in endoscopic or laparoscopic minimally invasive surgery is the passing of sutures and suturing which requires the clinician to develop skills such as three-dimensional depth perception and hand-to-hand transfer of a needle and suture while the target tissue and instruments are observed on a two-dimensional video monitor. Therefore, it is desirable to present a model suitable for practicing suturing and, in particular, there is a need for a model that isolates a particular step of a procedure for the trainee such as the passing of sutures for the clinician to practice in a simulated laparoscopic environment. The laparoscopic training model is removably placed inside a simulated laparoscopic environment such as a laparoscopic trainer in which it is at least partially obscured from direct visualization. A camera and monitor provide visualization to the practitioner. After a technique is practiced, it is furthermore desirable that such a model permits repeatable practice with ease, speed and cost savings. In view of the above, it is an object of this invention to provide a surgical training device that realistically simulates an anatomy and isolates a particular stage or step of a procedure that also enables repeatable practice. It has been demonstrated that the use of simulation trainers greatly enhances the skill levels of new laparoscopists and are a great tool to train future surgeons in a non-surgical setting. There is a need for such improved, realistic and effective surgical training models.

SUMMARY OF THE INVENTION

According to one aspect of the invention, a suture training model is provided. The suture training model includes a base having a top surface interconnected with a bottom surface. The base includes a plurality of openings in the top surface extending toward the bottom surface. The suture training model further includes a plurality of suture tabs removably connected to the base. Each suture tab is made of elastic material having a longitudinal axis and capable of being pierced with a suture needle and pulled along the longitudinal axis from a resting configuration to an elongated configuration. At least one suture tab is located inside one or more of the plurality of openings such that it is removably retained inside the opening and permitting more than one fixed orientation of the suture tab about its longitudinal axis with respect to the base. Each suture tab has a top portion and a bottom portion. At least part of the top portion of the suture tab extends above the top surface of the base when residing inside an opening of the base and when pulled into the elongated configuration, the bottom portion is retained with respect to the base and the length of the suture tab along the longitudinal axis is increased in the elongated configuration relative to the resting configuration.

According to another aspect of the invention a suture training model is provided. The suture training model includes a base that holds a plurality of suture tabs that can be replaced, stretched, and rotated with respect to the base. Each suture tab includes a tab face that is capable of being pierced or including at least one pre-formed aperture through which a suture is to be passed. The base includes a plurality of openings for receiving the plurality of suture tabs. Each opening in the base holding one or more suture tabs. The base includes at least one angle to form at least two planes with openings for holding suture tabs.

According to another aspect of the invention, a suture training model is provided. The suture training model includes a base having a top surface interconnected with a bottom surface. The base including a plurality of openings in the top surface extending toward the bottom surface. The suture training model includes a plurality of suture tabs removably connected to the base. Each suture tab has a longitudinal axis and is capable of being pierced with a suture needle or including a pre-formed opening through which a suture is to be passed. At least one suture tab is located inside one or more of the plurality of openings such that it is removably retained inside the opening. Each suture tab has a top portion and a bottom portion. At least part of the top portion of the suture tab extends above the top surface of the base when residing inside an opening of the base. The opening has at least one mating surface such as an angled surface about the longitudinal axis and the suture tab has at least one mating surface such as an angled surface that is sized configured to mate with the at least one mating surface of the opening to prevent rotation of the suture tab about the longitudinal axis. In one variation, the suture tab and opening in which it is disposed are configured to permit more than one fixed orientation of the suture tab about its longitudinal axis with respect to the base. The suture tab and opening have more than one mating surface to permit more than one fixed orientation about the longitudinal axis with respect to the base.

According to another aspect of the invention, a method for practicing suture passing is provided. The method includes the step of providing a suture training model that includes a base having a plurality of openings configured to hold a plurality of suture tabs. Each suture tab of the model has a tab face that is capable of being pierced or includes at least one pre-formed aperture for passing a suture. The base of the model includes a plurality of openings for receiving the plurality of suture tabs. Each opening holds one or more suture tabs. Each suture tab is capable of being pulled along the longitudinal axis from a resting configuration to an elongated configuration. The suture tab in the elongated configuration has a longer length along the longitudinal axis relative to the resting configuration. The method further includes the steps of providing a suture and a suture needle, pulling a suture tab relative to the base from a resting configuration to an elongated configuration, and passing the suture and suture needle through the tab face while in the elongated configuration.

DETAILED DESCRIPTION OF THE INVENTION

Figure 1:
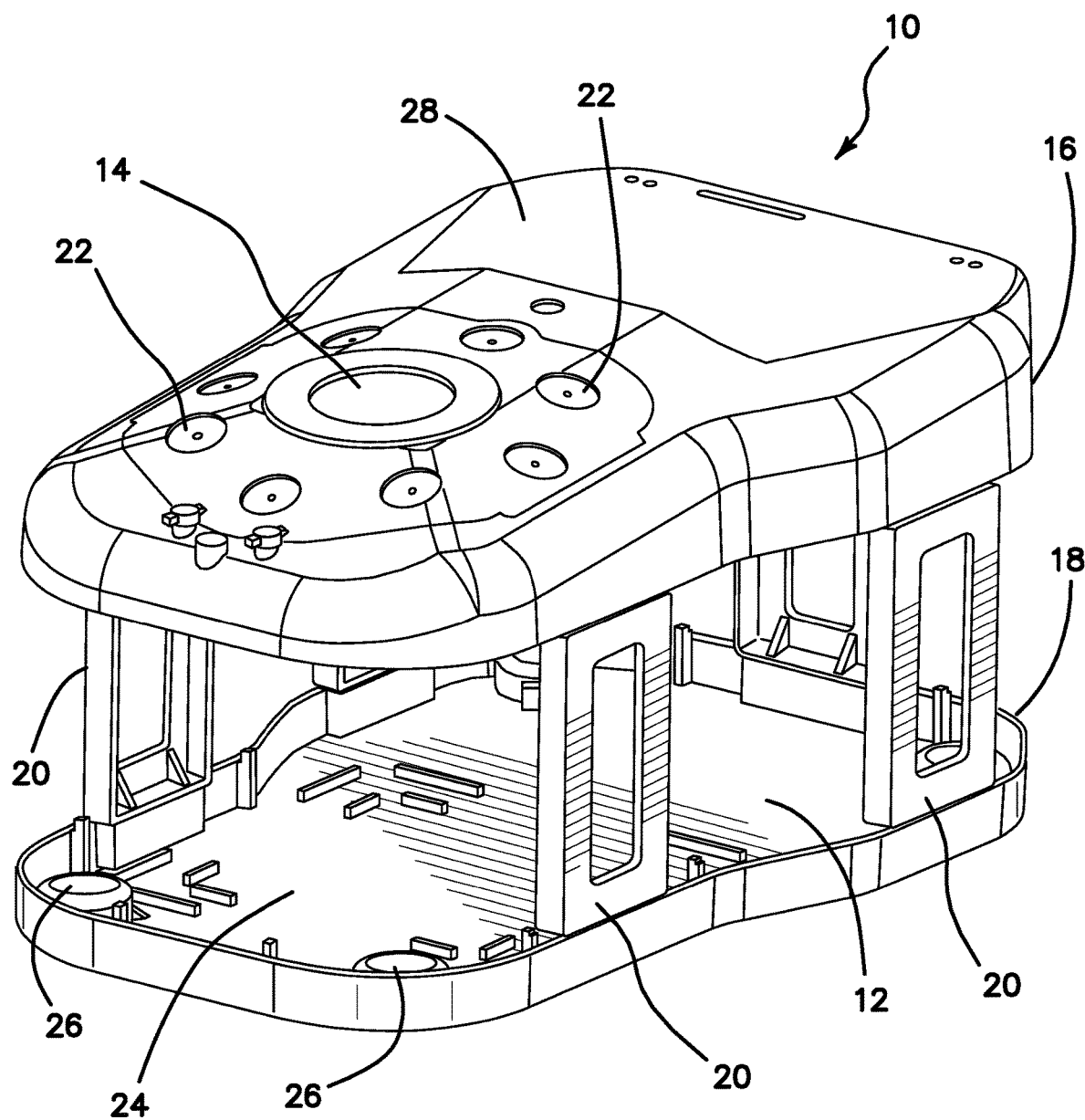
FIG. 1 illustrates a top perspective view of a surgical training device according to the present invention.

A surgical training device 10 that is configured to mimic the torso of a patient such as the abdominal region is shown in FIG. 1. The surgical training device 10 provides a body cavity 12 substantially obscured from the user for receiving simulated or live tissue or model organs or training models of the like described in this invention. The body cavity 12 is accessed via a tissue simulation region 14 that is penetrated by the user employing devices to practice surgical techniques on the tissue or practice model found located in the body cavity 12. Although the body cavity 12 is shown to be accessible through a tissue simulation region, a hand-assisted access device or single-site port device may be alternatively employed to access the body cavity 12. An exemplary surgical training device is described in U.S. patent application Ser. No. 13/248,449 entitled "Portable Laparoscopic Trainer" filed on Sep. 29, 2011 and incorporated herein by reference in its entirety. The surgical training device 10 is particularly well suited for practicing laparoscopic or other minimally invasive surgical procedures.

Still referencing FIG. 1, the surgical training device 10 includes a top cover 16 connected to and spaced apart from a base 18 by at least one leg 20. FIG. 1 shows a plurality of legs 20. The surgical training device 10 is configured to mimic the torso of a patient such as the abdominal region. The top cover 16 is representative of the anterior surface of the patient and the space 12 between the top cover 16 and the base 18 is representative of an interior of the patient or body cavity where organs reside. The surgical trainer 10 is a useful tool for teaching, practicing and demonstrating various surgical procedures and their related instruments in simulation of a patient undergoing a surgical procedure. Surgical instruments are inserted into the cavity 12 through the tissue simulation region 14 as well as through pre-established apertures 22 in the top cover 16. Various tools and techniques may be used to penetrate the top cover 16 to perform mock procedures on simulated organs or practice models placed between the top cover 16 and the base 18. The base 18 includes a model-receiving area 24 or tray for staging or holding a simulated tissue model or live tissue. The model-receiving area 24 of the base 18 includes frame-like elements for holding the model (not shown) in place. To help retain a simulated tissue model or live organs on the base 18, a clip attached to a retractable wire is provided at locations 26. The retractable wire is extended and then clipped to hold the tissue model in position substantially beneath the tissue simulation region 14. Other means for retaining the tissue model include a patch of hook-and-loop type fastening material (VELCRO®) affixed to the base 18 in the model receiving area 24 such that it is removably connectable to a complementary piece of hook-and-loop type fastening material (VELCRO®) affixed to the model.

A video display monitor 28 that is hinged to the top cover 16 is shown in a closed orientation in FIG. 1. The video monitor 62 is connectable to a variety of visual systems for delivering an image to the monitor. For example, a laparoscope inserted through one of the pre-established apertures 22 or a webcam located in the cavity and used to observe the simulated procedure can be connected to the video monitor 28 and/or a mobile computing device to provide an image to the user. Also, audio recording or delivery means may also be provided and integrated with the trainer 10 to provide audio and visual capabilities. Means for connecting a portable memory storage device such as a flash drive, smart phone, digital audio or video player, or other digital mobile device is also provided, to record training procedures and/or play back pre-recorded videos on the monitor for demonstration purposes. Of course, connection means for providing an audio visual output to a screen larger than the monitor is provided. In another variation, the top cover 10 does not include a video display but includes means for connecting with a laptop computer, a mobile digital device or tablet such as an IPAD® and connecting it by wire or wirelessly to the trainer.

When assembled, the top cover 16 is positioned directly above the base 18 with the legs 20 located substantially around the periphery and interconnected between the top cover 16 and base 18. The top cover 16 and base 18 are substantially the same shape and size and have substantially the same peripheral outline. The internal cavity is partially or entirely obscured from view. In the variation shown in FIG. 1, the legs include openings to allow ambient light to illuminate the internal cavity as much as possible and also to advantageously provide as much weight reduction as possible for convenient portability. The top cover 16 is removable from the legs 20 which in turn are removable or collapsible via hinges or the like with respect to the base 18. Therefore, the unassembled trainer 10 has a reduced height that makes for easier portability. In essence, the surgical trainer 10 provides a simulated body cavity 12 that is obscured from the user. The body cavity 12 is configured to receive at least one surgical model accessible via at least one tissue simulation region 14 and/or apertures 22 in the top cover 16 through which the user may access the models to practice laparoscopic or endoscopic minimally invasive surgical techniques.

Figure 2:
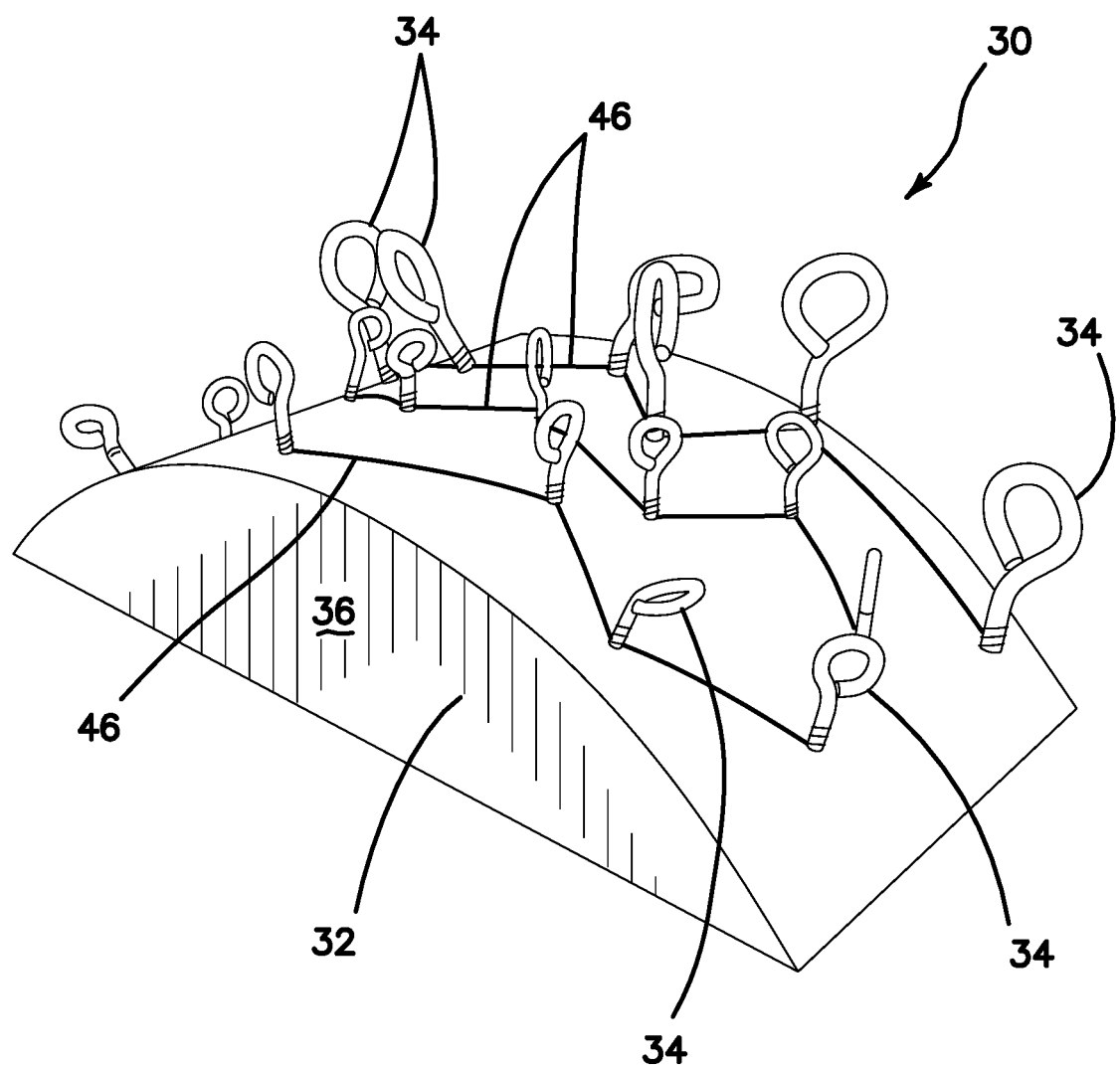
FIG. 2 illustrates a top perspective view of a model according to the present invention.

A model 30 for the practice of passing sutures in laparoscopic procedures according to the present invention is shown in FIG. 2. The model 30 is configured to be placed inside the surgical training device 10 described above or other similar surgical trainer to simulate suturing within a body cavity. The model 30 includes a base 32, and a plurality of eyelets 34 connected to the surface of the base 32.

The base 32 of the model 30 is a platform that serves as a bottom support for the rest of the model 30 and it is sized and configured such that the model does not tip over. The platform is made of any material such as metal or plastic. The base 32 is of sufficient heft to maintain the stability of the model 30 in the upright position while being manipulated by a user. The model 30 is sized and configured to be placed into the body cavity 12 of the surgical trainer 10 in the location of the model receiving area 24. The underside of the base 32 is provided with means to affix the model 30 inside the surgical trainer 10. Such means to affix the model 30 inside the trainer 10 include but are not limited to adhesive, suction cup, magnet, snap-fit, and a hook-and-loop type fastener material attached to the bottom surface of the base 32 and configured to connect with a complementary hook-and-loop type fastener material or adhesive attached to the base 18 of the surgical trainer 30.

Figure 3:
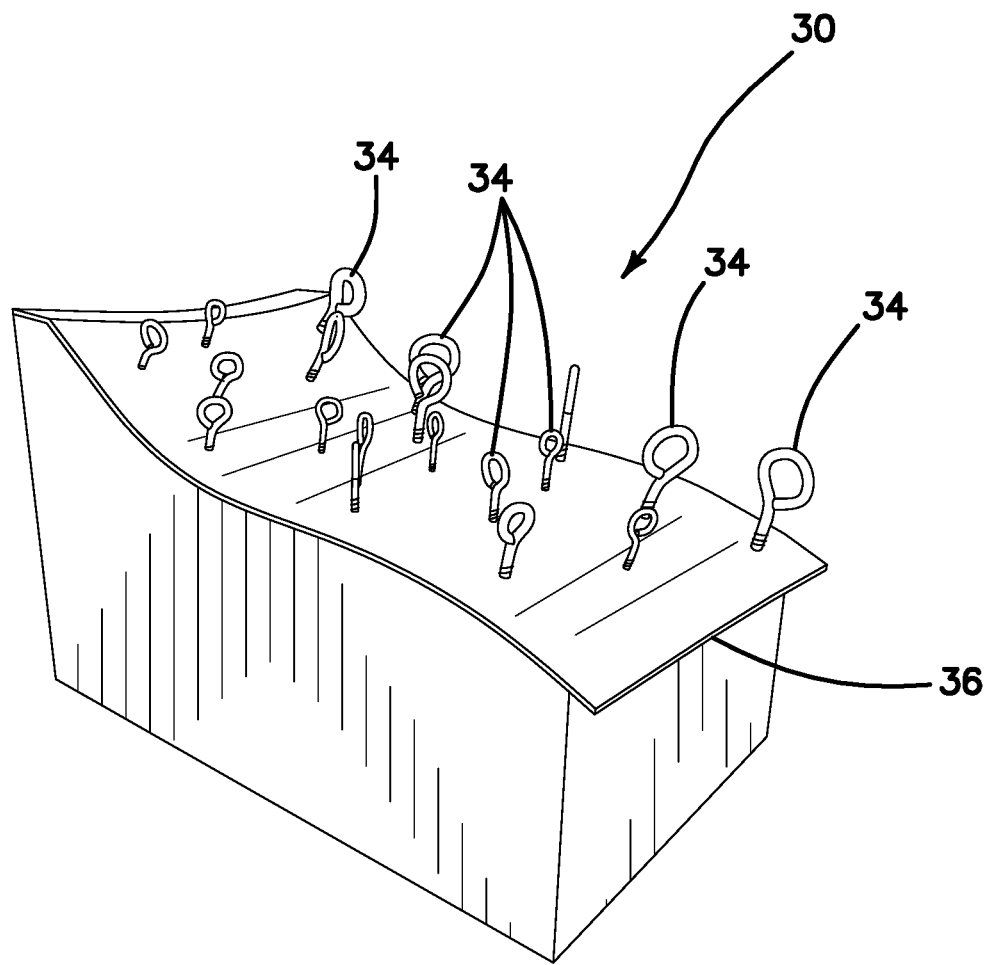
FIG. 3 illustrates a top perspective view of a model according to the present invention.

The base 32 of the model 30 includes an outer surface 36 which may be flat or contoured in various ways. For example, the outer surface can be convex as shown in FIG. 2. The outer surface 36 may be concave, curved, sloped, undulating or otherwise have any configuration or geography including an upward hill, a downward hill, valleys and peaks including smaller surface additions such asv bumps or divots that complement the larger features. The geography of the outer surface 36 creates a varying surface or numerous planes to permit the user to practice depth perception in laparoscopic surgery. In one variation, the base 32 is not rigid and solid but is pliable, resilient and flexible, and deflectable when manipulated with surgical instruments that would be used in laparoscopic surgery. As such, the base 32 is made of pliable, resilient material such as rubber or silicone. Another example of the geography of the outer surface 36 of the base 32 is shown in FIG. 3. The model 30 in FIGS. 2 and 3 is shown positioned with the operative outer surface 36 facing upwardly. However, the model 30 may be positioned on its side in the trainer 10 to provide another variation and representation of internal bodily structures for practicing laparoscopic procedures. In this alternative orientation, the side surface of the model 30 is provided with eyelets 34.

Figure 4A:
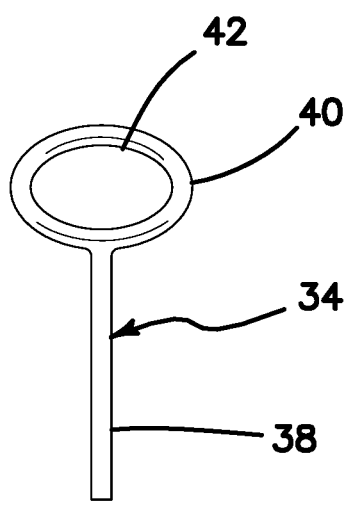
FIG. 4A is a front elevational view of an eyelet according to the present invention.
Figure 4B:
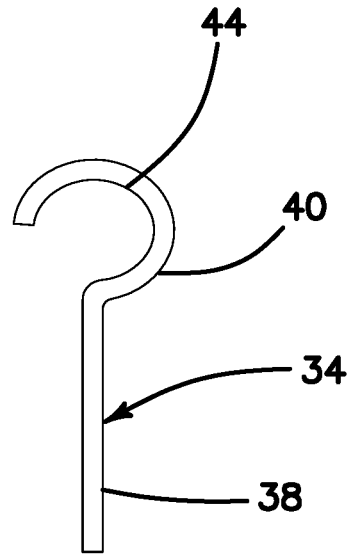
FIG. 4B is a front elevational view of an eyelet according to the present invention.

The model 30 includes a plurality of eyelets or apertures 34 connected to the base 32 such that the eyelets 34 are configured to reside above the outer surface 36 or side surface of the model 30 as shown in FIGS. 2 and 3. An exemplary eyelet 34 is shown in FIG. 4A. In general, the eyelet 34 is configured to provide an opening through which a clinician can practice passing a needle and suture. The eyelet 34 includes a neck portion 38 and a head portion 40. The head portion 40 includes at least one aperture 42 defining an aperture plane in which it lies. Although the aperture 42 is shown to have a circular shape, the invention is not so limited and the aperture 42 can have any shape such as a polygon or closed curve. While FIG. 4A depicts a closed aperture 42, an open aperture 44 is within the scope of the present invention as shown in FIG. 4B. An open or hook-like aperture 44 is an aperture that is open and only partially enclosed by surrounding material of the head portion 40 leaving an opening or entry into the aperture 40 that is anywhere from approximately ⅛ to ¼ of the aperture perimeter in size. In one variation, the aperture 42 of the eyelet 34 is covered with a layer of silicone or other penetrable material that may include a mesh or fabric reinforcement such that passing a needle and suture through the aperture 42 requires piercing the covering of the aperture 42 with the needle and suture. The covering mimics real tissue and thus contributes to the realism of the exercise.

Figure 4C:
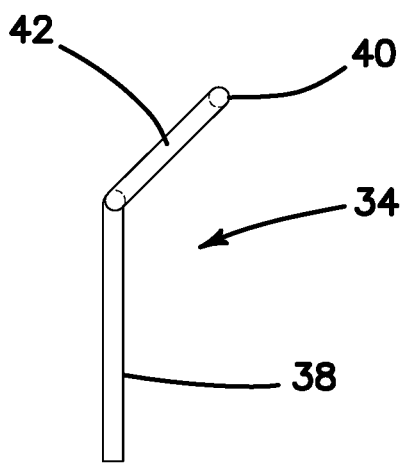
FIG. 4C is a side elevational view of an eyelet according to the present invention.
Figure 4D:
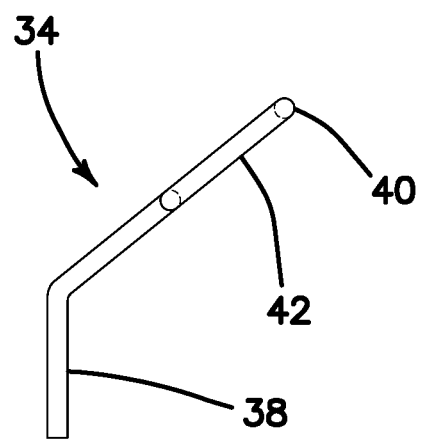
FIG. 4D is a side elevational view of an eyelet according to the present invention.

In one variation, the eyelet 34 is rigid. In another variation, the neck portion 38 of the eyelet 34 is flexible while the head portion 40 is rigid and in another variation both the neck portion 38 and head portion 40 are flexible or capable of being deflected. A deflectable or flexible eyelet 34 increases the difficult of performing suture passing. In another variation, the eyelet 34 is pre-bent or angled. The plane defined by the aperture intersects with the longitudinal axis of the neck portion 38 as shown in FIGS. 4C and 4D. In general, the eyelet 34 provides an aperture 42 for the surgeon to practice passing a needle and suture through. The neck 38 of the eyelet 34 is configured to space the aperture 42 from the outer surface 36 of the base 32. Other means for spacing the aperture 42 from the outer surface 36 of the base 32 are within the scope of the present invention. Also, the neck 38 is configured to connect to the base 32 and as such, the neck 38 may include threads, adhesive or other means for connection to the base. Also, the eyelet 34 may be mounted to the base 32 such that the entire eyelet 34 rotates or is rotatable with respect to the base 32 and, in another variation, the eyelet 34 is configured such that the head 40 of the eyelet 34 rotates with respect to the neck portion 38 in a free-spinning eyelet configuration. Such resulting rotatability of the aperture 42 with respect to the base 32 increases the difficulty of passing sutures.

A plurality of eyelets 34 are connected to the outer surface 36 of the base 32 as shown in FIGS. 2 and 3. In another variation, one or more eyelets 34 is retractable with respect to the outer surface 36 such that the retractable eyelet 34 has a first position in which the aperture 42 of the eyelet 34 is at a first distance relative to the outer surface 36 and a second position in which the aperture 42 is at a second distance relative to the outer surface 36 wherein the second distance is greater above the outer surface 36 than the first distance. In one variation, the eyelet 34 is biased towards the first position such that the eyelet 34 has a tendency to spring back toward the first position. Furthermore, at least one eyelet 34 is connected to the base 32 such that at least a portion of the eyelet 34, such as at least a portion of the aperture 42 of the eyelet 36, is beneath the upper surface 36 so that the eyelet 34 is visible to user but, in order to pass a suture through the eyelet 34, the eyelet 34 laying partially beneath the surface is pulled-up or extracted by the user and held with one instrument in the extracted position so that the suture needle and suture may be passed through the aperture 42 of the eyelet 34 with another instrument held in the opposite hand. When released from the extracted position, the eyelet 34 would retract back to its at least partial sub-surface position. The retractable eyelet 34 is embedded in an elastic base different from the upper surface 36 or spring biased with respect to the upper surface 36. Also, the retractable eyelet 34 is biased in the retracted position such that force is required to pull the eyelet above surface and hold it in position above the upper surface 36 for suture passing. When released, the eyelet 34 would be pulled back toward beneath the surface. In another variation, the retractable eyelets 34 are not biased inwardly but move in and out between a first position and a second above-surface position wherein the first position may be at least partially beneath the surface. The eyelets 34 would be slotted to move within a slot axially relative to the upper surface 36. Each eyelet 34 may be the same or the plurality of eyelets 34 may include a mixture of eyelets 34 having different features described above such as eyelets with apertures 42 of different sizes and shapes, flexible eyelets, rotatable eyelets, covered eyelets, open eyelets, deflectable eyelets, retractable eyelets, plastically deformable eyelets which when deflected remain deflected and deflectable eyelets that resume their previous position after being deflected. The plurality of eyelets 34 may include eyelets of different colors including colors that blend in against the background or color of the outer surface 36 of the base 32 for increased difficulty in visualizing the eyelet aperture 42 on a camera viewing monitor. Also, at least one of the eyelets 34 attached to the base 32 may also be colored such that the eyelet 34 visually stands out or is in contrast when viewed against the background or outer surface 36 of the base with a laparoscope. Furthermore, the plurality of eyelets 34 may include one or more groups of eyelets that have the same color, thus being color-coded so that a predetermined path along which a suture must be passed is defined by the color of the eyelets 34. For example, a set of green-colored eyelets 34 may define either a predetermined path that is particular to a surgical procedure or may define a relatively easy skill level defined by eyelets 34 with relatively large apertures 42, for example. Alternatively, the predetermined path may be marked not with the coloring of the eyelets 34 but with markings 46 on the outer surface 36 of the base 32 as shown in FIG. 2. Such markings 46 on the outer surface 36 can include anatomical landmarks from which the user can deduct the correct pathway to follow for passing sutures. Alternatively, the markings 46 are lines drawn on the outer surface 36 between eyelets 34 interconnecting them to define the predetermined path. The line 46 is contrast colored against the base 32 as in FIG. 2 and may be color-coded to indicate a particular predetermined pathway. Also, among the plurality of eyelets 34 attached to the base 32, groups of eyelets 34 may be interconnected with markings 46 such as lines drawn on the base 32 that connect the eyelets 34 within a certain group. The certain group of eyelets can define a predetermined pathway to follow for testing the skill of the user making sure that all eyelets 34 of a particular group lying along a particular pathway have been passed through with a suture. Hence, the arrangement and choice of eyelets 34 in a subset of eyelets 34 among a plurality attached to the base, can be used to improve the skill of passing a needle and suture through an aperture and as such the pathways and eyelets selected in each pathway can vary in difficulty from relatively easy eyelets, for example, ones having large apertures, standing upright, being rigid or located in relatively flat areas of the outer surface and being starkly contrasted against the background to more difficult eyelets, for example ones comprising smaller apertures, flexible eyelets, deflectable eyelets so eyelets colored so as to blend in with the background. The base 32 may be sold as part of a kit with a plurality of different types of eyelets 34 described above which the user would then assemble by selecting from the plurality of different eyelets and then placing them as desired into the base 32 to form a custom pathway for practice. The eyelets 34 and base 32 are configured such that the eyelets 34 can be pushed through the outer surface 36 of the base 32 to securely attach the eyelets 34. The kit may also include organs or other anatomical features that can also be connected to the base to create an anatomy suitable for a particular practice.

A predetermined pathway for passing sutures may be predefined based on the surgical procedure to be practiced. For example, the practice of closing the vaginal vault may require a generally circular pathway at a particular angle with eyelets having small apertures. Accordingly, such a pathway may be defined and marked by eyelets of the same color or markings on the base for the surgeon to follow. Another surgical procedure such as anastomosis of a bowel may require a larger generally circular pathway of closely spaced pairs of eyelets. Hence, the surgical procedure to be practiced may determine the types of eyelets used and their arrangement and the markings indicating that particular pathway to the user.

The eyelets 34 are embedded within the base in a variety of patterns and configurations creating patterns and pathways. Some pathways may be aimed at making sure the clinician visualizes all the eyelets and successfully passes through all within a set without missing ones that are difficult to visualize or to pass a suture through. Of course, the eyelets are placed at differing heights and angles with the objective being for the surgeon to pass an actual suture needle or simulated suture needle through each eyelet and in a specific order to complete each pathway. There are multiple pathways with different sized eyelets for different skill levels which allows for skill advancement within the same platform. The practice model 30 is placed inside a laparoscopic trainer 10 and a laparoscope is inserted into the cavity 12 to observe the model 30. A suture needle and suture are passed through one of the apertures 22 or tissue simulation region 14 into the cavity 12 and the procedure of passing the suture through the eyelets 34 is observed on the video display monitor 28 providing a two-dimensional video representation to the practitioner of the three-dimensional model 30 inside the laparoscopic trainer 10 and obscured from direct visualization. The model 30 and trainer 10 combination advantageously allow the user to practice identifying a desired surgical pathway for the suture, moving the needle and passing the suture through a number of eyelets 34 laparoscopically.

The model 30 may include interchangeable eyelets 34 in which the user may personally select certain eyelets or select a predetermined set of eyelets that corresponds to a pathway of a surgical procedure for practicing certain skills, difficulty levels or procedures. The model 30 is advantageously challenging and adjustable for all skill levels and effective in that the user must use both hands equally to complete the path. The suture needle must also be manipulated to be facing the proper direction for each pass in order to successfully pass it through the aperture. Hence, the model is particularly useful for the practice of laparoscopic suture passing, determining and visualizing tissue planes, the practice of depth perception and visualization of eyelets, hand-to-hand transfer of instruments and needles, suturing and tissue manipulation. This model allows clinicians to keep their skills sharp or to "warm-up" beforehand for successful outcomes in real surgery.

Figure 5A:
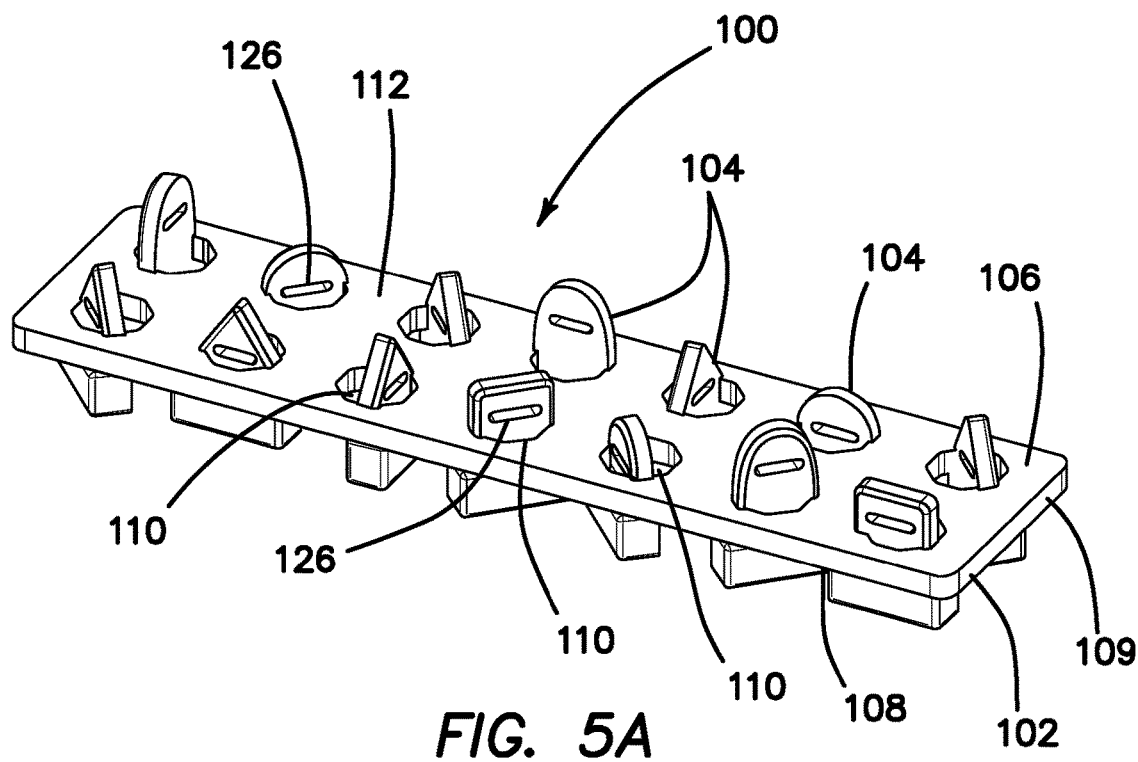
FIG. 5A illustrates a top perspective view of a suture training model with a single suture tab in each hole according to the present invention.
Figure 5B:
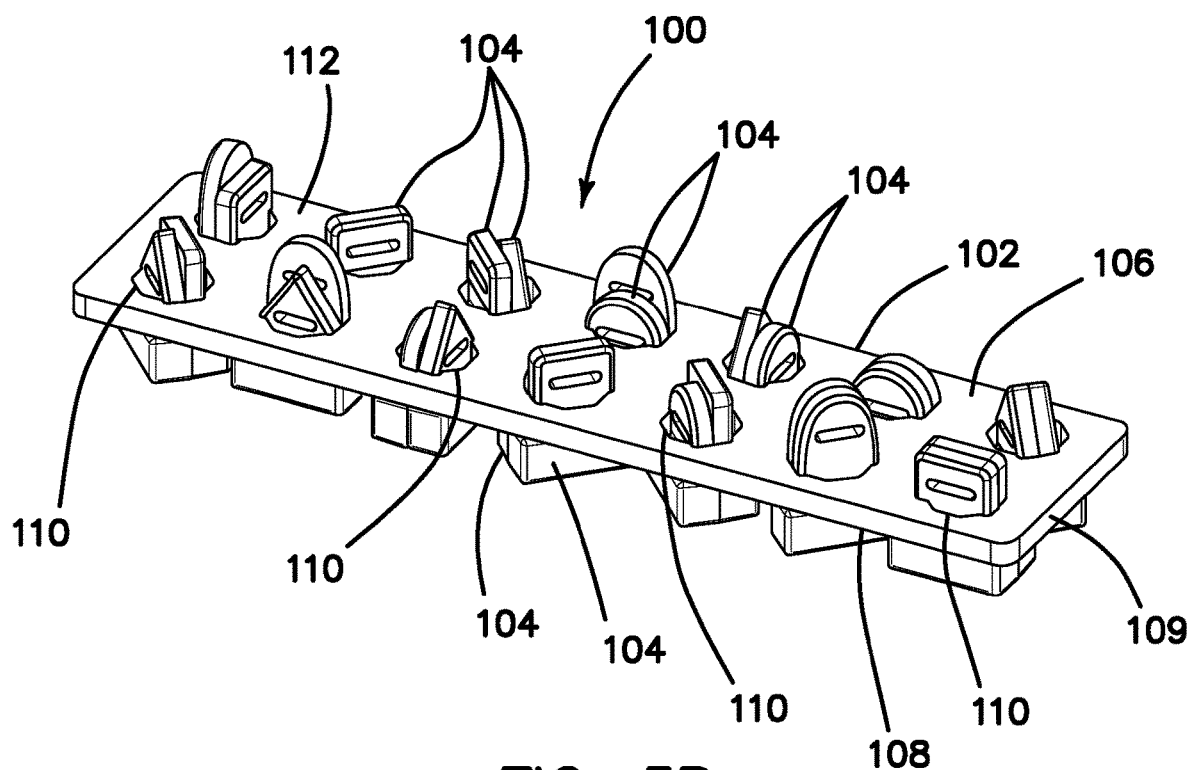
FIG. 5B illustrates a top perspective view of a suture training model with two eyelets in each hole according to the present invention.
Figure 7:
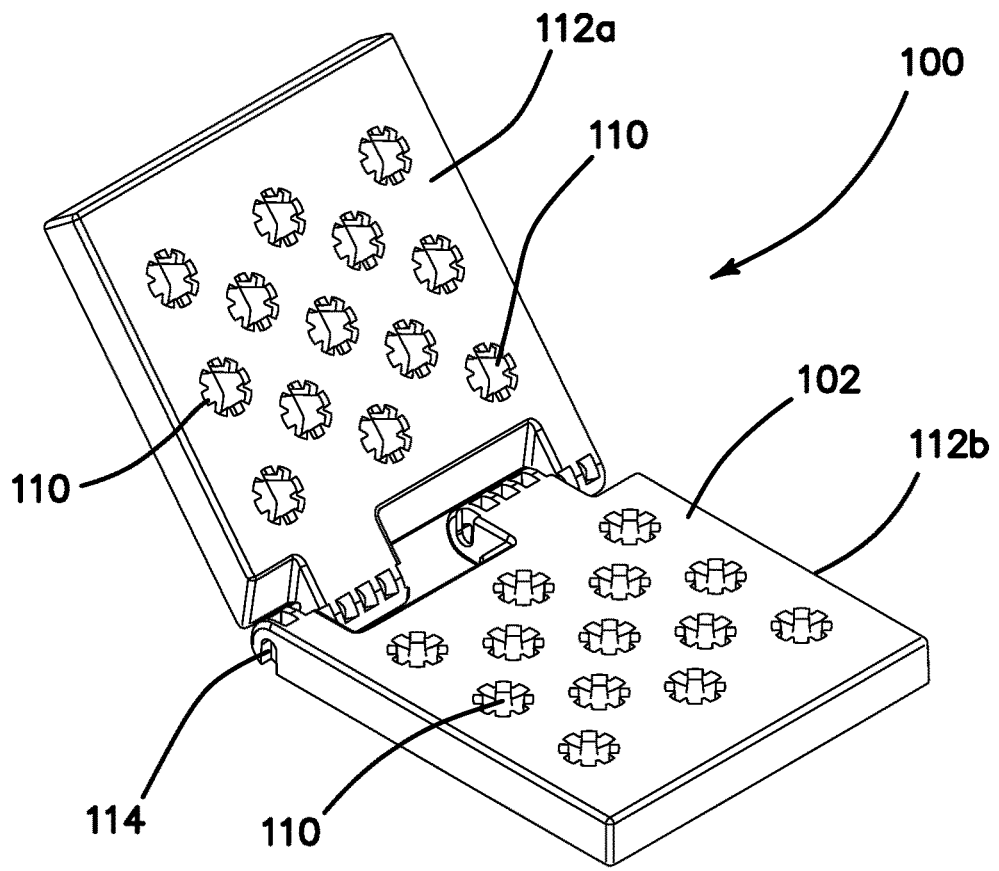
FIG. 7 illustrates a suture training model having two planes hinged together according to the present invention.

Turning now to FIGS. 5A-5B, there is shown another variation of a suture training model 100 according to the present invention. The model 100 includes a base 102 and a plurality of suture tabs 104 connected to the base 102. The base 102 includes a top surface 106 and a bottom surface 108 interconnected by a sidewall 109. Typically, the top surface 106 is parallel to the bottom surface 108 to define plate or planar structure having a thickness. A plurality of openings 110 are formed in the base 102 and extend between the top surface 106 and the bottom surface 108. The openings 110 are configured to receive a plurality of suture tabs 104. The base 106 is made of plastic, polymer or of any suitable material. The base 106 is generally rigid or semi-rigid and made be made of a single layer of material or contain one or more layers of material having different properties and characteristics. For example, a top base layer may be provided to impart a realistic tissue-like appearance to the model in color and/or texture and/or to increase the difficulty in approaching the target suture tabs 104 as will be discussed in greater detail below. The base 102 includes at least one opening-containing portion 112 that includes openings 110. For example, in FIG. 7 the suture training model 100 includes two portions 112A, 112B hinged together. Each portion 112 may comprise a single plane or include multiple interconnected planes or surfaces. In FIG. 7, each opening-containing portion 112A, 112B defines a separate plane. The separate planes may be formed/molded integrally with each other such that the planes and their relative angles are fixed such as shown in FIGS. 12-15. In another variation, the one or more opening-containing portions 112, whether they are planar or not, are movable with respect to each other such that the angle between one or more opening-containing portions 112 can be adjusted as desired. The angle may be adjusted and re-adjusted as needed to create a different suture passing landscape that may or may not be representative of anatomical situations. Also, the angle may be adjusted to create a custom and variable level of difficulty for practicing suture passing on the model and, thereby, create a progressive learning experience. The angle between two or more distinct and separate opening-containing portions 112 may be fixed with a thumb screw, friction-fit or other arrangement configured to lock the relative position such as by tightening a hinge 114 connecting the two or more planes 112. In another variation, the separate opening containing portion 112 or surfaces of opening-containing portions 112, whether they are planar or not, are moved relative to each other by bending the base 102. In such a variation, the base 102 is made of a suitable pliable material, such as aluminum, and having a thickness that would permit the base to bend.

Figure 6:
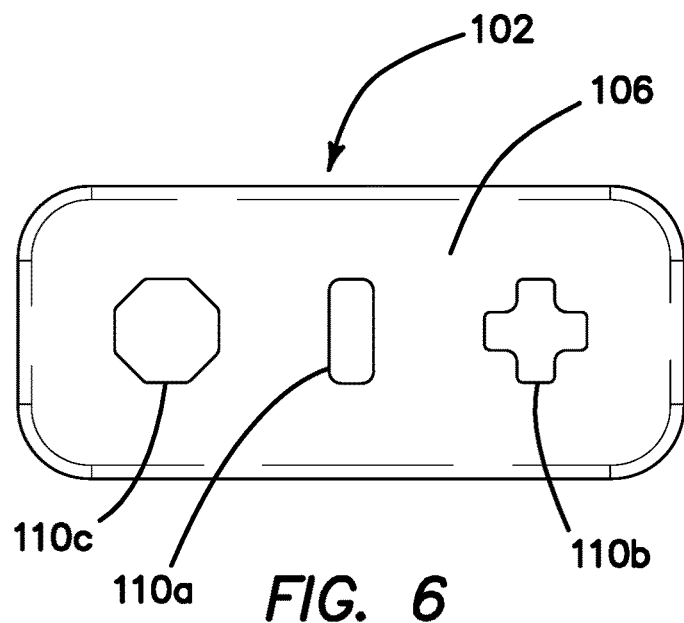
FIG. 6 illustrates a plurality of holes with different shapes in a section of a base of a suture training model according to the present invention.

With reference back to FIGS. 5A-5B and with additional reference to FIGS. 6-7, the openings 110 in the base 102 will now be described in greater detail. Each opening 110 defines a longitudinal axis that is substantially normal to the opening 110 at the top surface. Each opening 110 is sized and configured to removably receive at least one suture tab 104. Some of the possible shapes of the openings 110 in the base 102 when viewed along the longitudinal axis are shown in FIG. 6. In FIG. 6, one opening 110A has shape of a slot. The slot is rectangular and elongate. The opening 110A has a shape that is complementary to the rectangular shape of at least a portion the suture tab 104 that is to be received in the opening 110A. The slot is sized to be slightly larger or slightly smaller to create a friction-fit engagement with the suture tab for retaining the tab inside the base opening. Still referencing FIG. 6, another exemplary opening 110B has a cross-like or X-like shape. The cross-shaped opening 110B is formed by two rectangular openings, each similar to the rectangular slot-like opening 110A, that intersect at 90 degrees. The cross-like shape of opening 110B allows at least a portion of a suture tab 104 with a complementary rectangular shape to be inserted into one of the two legs of the opening 110B. The tab 104 is inserted in a first direction or orientation and removable to be also inserted in the other leg of the opening 110B in a second direction that is lateral, perpendicular or angled with respect to the first direction. The ability to receive a suture tab 104 in more than one orientation within a single opening 110 allows the suture pathway to be defined as desired making it easier or more difficult to pass sutures through the suture tabs 104 because of their orientation within multi-directional openings 110 relative to the orientation of adjacent suture tabs 110. Still referencing FIG. 6, in another variation, an opening 110C has an octagonal shape permitting alignment of suture tabs 104 inside the opening along four different directions. The opposite facets of a multi-faceted opening, such as the octagon, provide alignment and a friction-fit engagement against the suture tab 104 inside the opening 110C. At least part of the suture tab 104 is sized to conform closely to the facets and abut the edges of the opening 110. Similar to the octagonal-shaped opening 110C, FIG. 7 illustrates a star-like shaped opening 110 defined by four intersecting rectangular openings that permit a suture tab 104 to be oriented in four different angles and directions within one of the four intersecting rectangular openings. A circular opening 110 would also work to retain the suture tab 104 within the opening 110 but would not act to orient the tab in any predefined direction.

With reference to FIG. 7, there is shown a suture training model 100 according to the present invention. The suture training model 100 includes two opening-containing portions 112A, 112B movably connected at a hinge 114. A first opening-containing portion 112A can angulate with respect to a second opening-containing portion 112B. Each of the first and second opening containing portions 112A, 112B is substantially planar and includes a plurality of star-like shaped openings 110. All of the openings 110 are shown to have the same shape. In another variation, the openings 110 may have different shapes. A base 102 with openings 110 having different shapes help communicate a pre-defined pathway to the user who would insert suture tabs 104 into the openings 110 according to their predefined angulation relative to adjacent openings.

Figure 8:
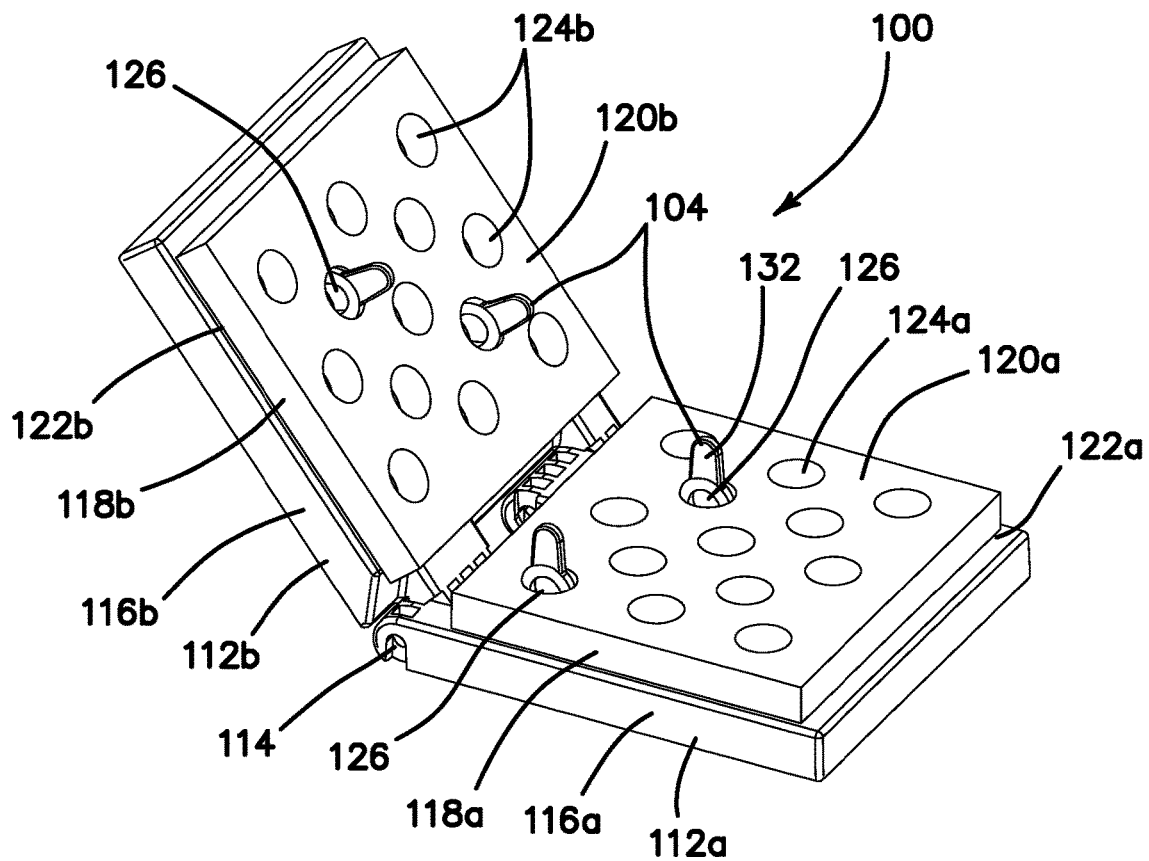
FIG. 8 illustrates a suture training model having a base with two planes hinged together, each plane having a layer of compressible material and a plurality of suture tabs connected to the base according to the present invention.

Turning now to FIG. 8, there is shown another suture training model 100 according to the present invention. The suture training model 100 includes a base 102 having more than one layer. In particular, the base 102 includes a first layer 116 and a second layer 118. The second layer 118 is located above the first layer 116. In the variation of the suture training model 100 shown in FIG. 8, the base 102 includes a first opening-containing portion 112A connected at an angle to a second opening-containing portion 112B via a hinge 114 making the first opening-containing portion 112A adjustable and movable with respect to the second opening-containing portion 112B. In one variation, each portion 112A, 112B has a separate second layer 118A, 118B, respectively. In another variation, a single second layer 118 spans both portions 112A, 112B bridging any gap therebetween. The second layer 118 includes a top surface 120 and a bottom surface 122 defining a thickness. The bottom surface 122 of the second base layer 118 abuts and overlays the top surface of the first base layer 116 and may be attached with adhesive. The second base layer 118 further includes a plurality of apertures 124 extending between the top surface 120 and the bottom surface 122. The apertures 124 of the second base layer 118 are aligned with the openings 110 in the first base layer 116 to permit suture tabs 104 to extend through both layers 116, 118. In one variation, at least a portion of the suture tab 104 extends above the top surface 120. In another variation, the suture tab 104 does not extend above the top surface 120. The variation of the suture training model 100 of FIG. 8 includes two opening-containing portions 112A, 112B that are connected to each other with a hinge 114 and each is shown to include a first base layer 116A, 116B, second base layer 118A, 118B, and apertures 124A, 124B, respectively. The second layer 118 is made of soft compressible material, such as foam, imparting the base 102 with a realistic tissue surface while serving to hide and embed the suture tabs 104. The addition of a soft foam second layer 118 adds to the experience, providing another material which must be manipulated by the user in order to complete the exercise. For example, the user may push down or compress the foam second layer 118 to access or view the aperture 126 of the suture tab 104.

Figures 9A, 9B:
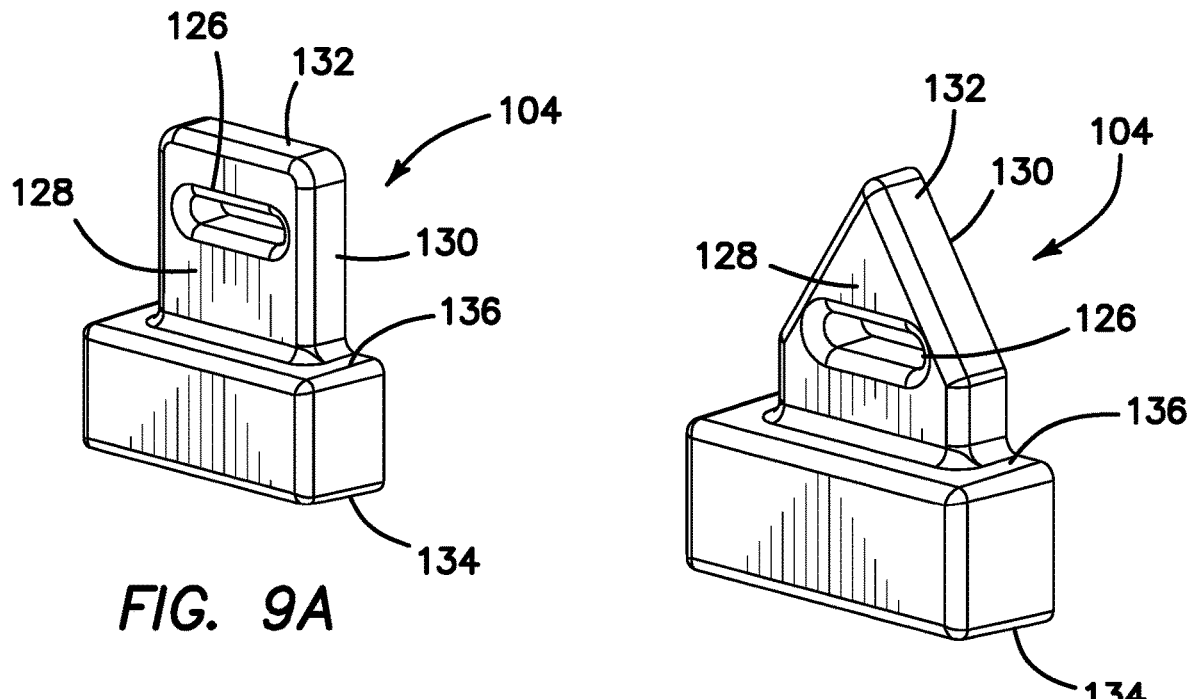
FIG. 9A is a top perspective view of a suture tab according to the present invention.
FIG. 9B is a top perspective view of a suture tab according to the present invention.
Figure 9C:
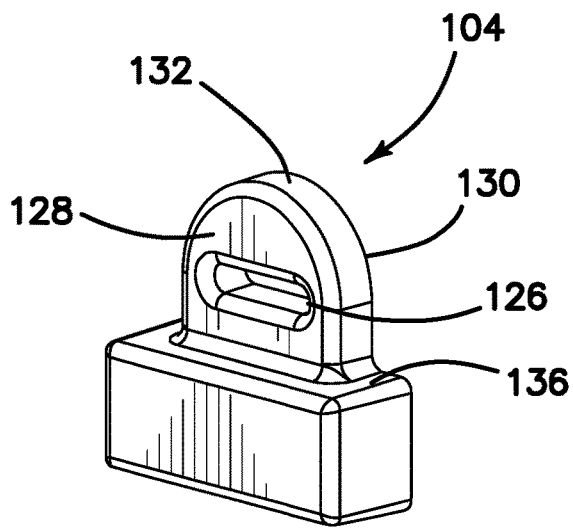
FIG. 9C is a top perspective view of a suture tab according to the present invention.
Figure 9D:
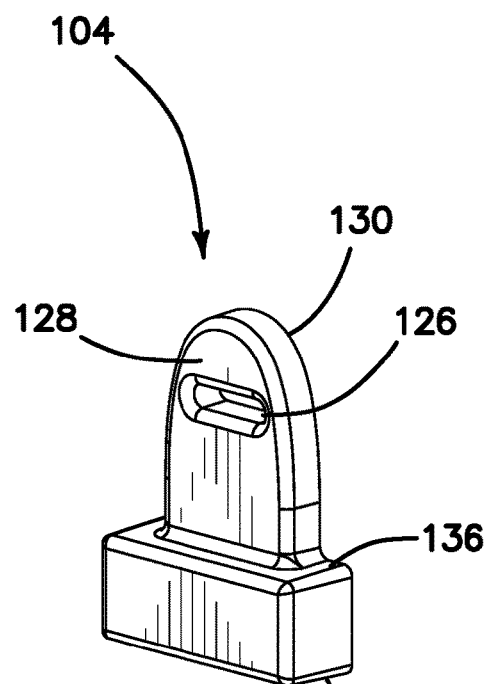
FIG. 9D is a top perspective view of a suture tab according to the present invention.

Turning now to FIGS. 9A-9D, there are shown several variations of a suture tab 104 according to the present invention. The suture tab 104 includes a first side 128 and a second side 130 defining a thickness therebetween. The first and second sides 128, 130 are substantially vertical and are interconnected by a top 132 and a bottom 134. The suture tab 104 includes at least one pre-formed aperture 126 that extends between the first side 128 and the second side 130. The aperture 126 can be any shape and size. In one variation, the aperture 126 has an elongate slot-like shape. The elongate-shaped aperture 126 may include curved sides and be oval-like such that the aperture 126 has fewer stress concentrations when pulled. The suture tab 104 is made of elastic material such as silicone, elastomer, rubber or polymer. The suture tab 104 may also be made of rigid plastic. The bottom 134 of the suture tab 104 has a larger footprint and is larger than the top 132 portion. A ledge 136 is defined around at least a portion of the suture tab 104 at the intersection of the larger bottom 134 with the smaller top 132. The top 132 of the suture tab 104 may have any type of shape. For example, in FIG. 9A, the top 132 of the suture tab 104 has a flat shape to form a top that is square-like or rectangular-like around the aperture 126. In FIG. 9B, the top 132 has a taper or pointed end to form a triangular-like shape around the aperture 126. In FIG. 9C, the top 132 is rounded or curved. In FIG. 9D, the top 132 is also rounded and curved and longer and narrower than the top 132 of the suture tab 104 shown in FIG. 9C. The aperture 126 in FIG. 9D is also shorter than the aperture 126 of FIG. 9C. The suture tab 104 is sized and configured to be inserted into an opening 110 in the base 102. Prior to insertion, the suture tab 104 is aligned with an opening 110 in the base 102. In particular, if the opening 110 in the base 102 is configured for receiving a suture tab 104 in one direction such as the opening 110A in FIG. 6, the suture tab 104 is aligned with the opening 110. If the opening 110 is configured to permit multiple orientations of the suture tab 104 such as openings 110B, 110C in FIG. 6 and openings 110 in FIG. 7, the orientation of the suture tab 104 is selected and the suture tab 104 is inserted such that the suture tab 104 outer surface is aligned with the facets of the opening 110 to be retained therein. To insert the suture tab 104 into the base 102, the base 102 is approached from the bottom surface 108 and the smaller and narrower top 132 of the suture tab 104 leads the insertion into the opening 110 as aligned. When sufficiently inserted, the ledge 136 of the suture tab 104 will abut the bottom surface 108 of the base 102 to retain the suture tab 104 inside the opening 110. The suture tabs 104 are retained in the openings 110 with a slight interference fit between the soft silicone tabs 104 and the rigid plastic base 102.

Furthermore, the plurality of suture tabs 104 may include one or more groups of tabs 104 that have the same color, thus being color-coded so that a predetermined path along which a suture must be passed is defined by the color of the tabs 104. For example, a set of green-colored tabs 104 may define either a predetermined path that is particular to a surgical procedure or may define a relatively easy skill level defined by the tabs 104. The suture passing exercise would require users to pass the suture through the green tabs, for example, while avoiding the red tabs. In another variation, the red tabs can be replaced with tabs that do not contain apertures 126.

When inserted, the suture tabs 104 will rest in connection with the base 102 as shown in FIG. 5A. In FIG. 5A, the apertures 126 of the suture tabs 104 are resident substantially above the top surface 106 of the base 102. In another variation, the apertures 126 are resident substantially beneath the top surface 106 of the base 102 to hide or at least partially conceal the aperture 126 or part of the tab 104. In another variation, the openings 110 in the base 102 are sized and configured to receive more than one suture tab 104 side-by-side as shown in FIG. 5B. In FIG. 5B, two side-by-side suture tabs 104 are shown inserted in each opening 110. The two suture tabs 104 may have the same-shaped tops 132 or different shaped tops 132. Also, the adjacent suture tabs may be color-coded with different colors or have the same color. The suture tabs 104 extend above the top surface 106 of the base 102 such that the top 132 of the suture tab 104 may be grasped by the surgeon and pulled in a vertical direction. Pulling the elastic suture tab 104 will result in the suture tab 104 stretching in the vertical direction. Such stretching elongates the suture tab aperture 126 in the vertical direction making the aperture 126 larger. All the while, the pulling of the suture tab 104 is biased by the ledge 136 contacting the base 102 preventing the suture tab 104 from being pulled completely out of the base 102 when pulled upwardly. The suture tabs are removable with respect to the base 102 when moved downwardly. With more than one suture tab located inside an opening in a side-by-side placement of suture tabs, the user takes care to pull on the appropriate tab or to pull on both tabs as needed to complete the exercise. The suture tab 104 has a first resting configuration in which the suture tab aperture 126 has a first size and a second extracted, elongated or pulled configuration in which the suture tab aperture 126 has a second size that is larger than the first size. The suture tab 104 is movable between the first configuration and the second configuration by pulling the proximal end or top of the suture tab 104 upwardly relative to the base top surface 106. The second configuration makes suture passing easier as the aperture 126 has an enlarged vertical dimension when pulled. The elongated, slot-like aperture 126 of FIGS. 9A-9D has a longitudinal axis that is substantially perpendicular to the vertical pulling direction such that the vertical dimension of the aperture 126 is enlarged when pulled. In one variation the aperture 126 is merely a slit or cut in the tab that is barely visible, yet opens when pulled and stretched against the base.

Another variation of the suture tab 104 is shown in FIG. 8. The suture tab 104 of FIG. 8 has a circular aperture 126 and an extended top 132 that provides an area or extension that can be easily grasped by the user. The extension may have a different shape that is more difficult to grasp and to hold. In this variation, if the suture tab 104 is pulled upwardly the circular aperture will form an elongated and narrower configuration making suture passing through the aperture 126 more difficult; thereby, teaching the surgeon respect for tissue skills to more delicately handle the simulated tissue represented by the suture tab 104 during suturing. Hence, the suture tab 104 has a first resting configuration in which the suture tab aperture 126 has a first size having a first dimension and a second extracted or pulled configuration in which the suture tab aperture 126 has a second size wherein the first dimension is smaller than when in the first configuration, the first dimension being the same measured dimension in the first and second configurations. The suture tab 104 is movable between the first configuration and the second configuration by pulling the proximal end or top of the suture tab 104 upwardly relative to the base top surface 106. The second configuration makes suture passing more difficult by a narrowing of the aperture 126. The aperture 126 has a lateral dimension that has a component perpendicular to the vertical or pulling direction and it is the lateral dimension that decreases in size in the second configuration relative to the first configuration.

Figure 10A:
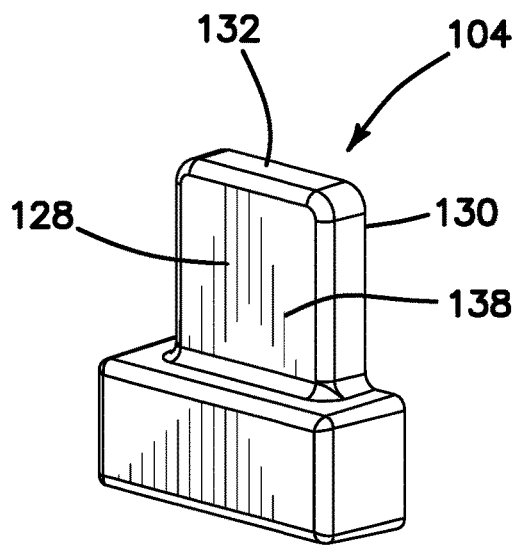
FIG. 10A is a top perspective view of a suture tab according to the present invention.
Figure 10B:
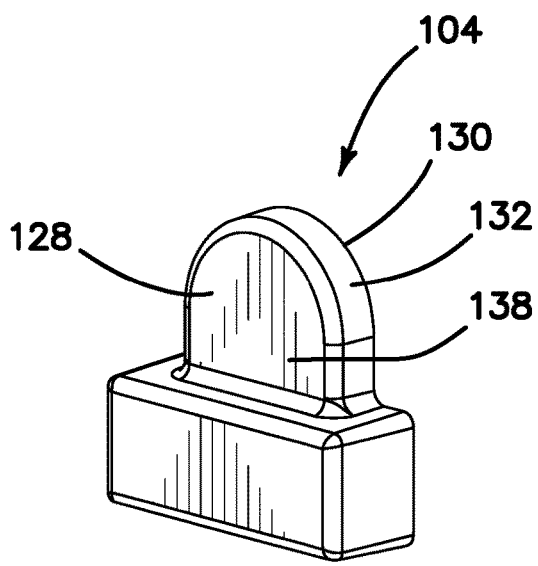
FIG. 10B is a top perspective view of a suture tab according to the present invention.

Turning now to FIGS. 10A-10B, there is shown variations of suture tabs 104 that do not have apertures 126. These suture tabs 104 are similar to the suture tabs of FIGS. 9A-9D but without apertures 126. The suture tab 104 in FIG. 10A has a flat top 132 forming a rectangular-like or square-like shape. The top 132 of the suture tab 104 defines a penetrable portion 138 between the first side 128 and the second side 130. In this variation, there is no pre-defined aperture 126 for practicing the passing of needle and suture. Instead, the practitioner pierces an aperture with a needle and passes a suture through the top 132 of the suture tab 104. The silicone material of the suture tab 104 creates a tissue-like feel when penetrating with a needle. Also, the top 132 of the tab 104 can be pulled upwardly and stretched and the suture tab 104 will respond like real tissue and stretch in a similar fashion to permit the passage of needle and suture. These aperture-less suture tabs 104 may be placed side-by-side in the same opening 110 with more than one other aperture-less suture tab 104 or be placed with more than one suture tab 104 having an aperture 126. In one variation, the suture tabs 104 do not have a ledge 136 on one side of the tab 104 such that the side is flush from top 132 to the bottom 134. This flush side of the suture tab 104 is placed against another flush side of another suture tab 104 in a side-by-side placement of two suture tabs 104 in one opening 110 leaving no space between the two tabs 104 making it more difficult to grasp and pull a single suture tab 104. In another variation, both opposite sides of a suture tab may not have a ledge such that a ledge is only located on two of the opposite four sides of the tab or along at least a portion of the tab sufficient to abut against the base and retain the tab.

Figure 11A:
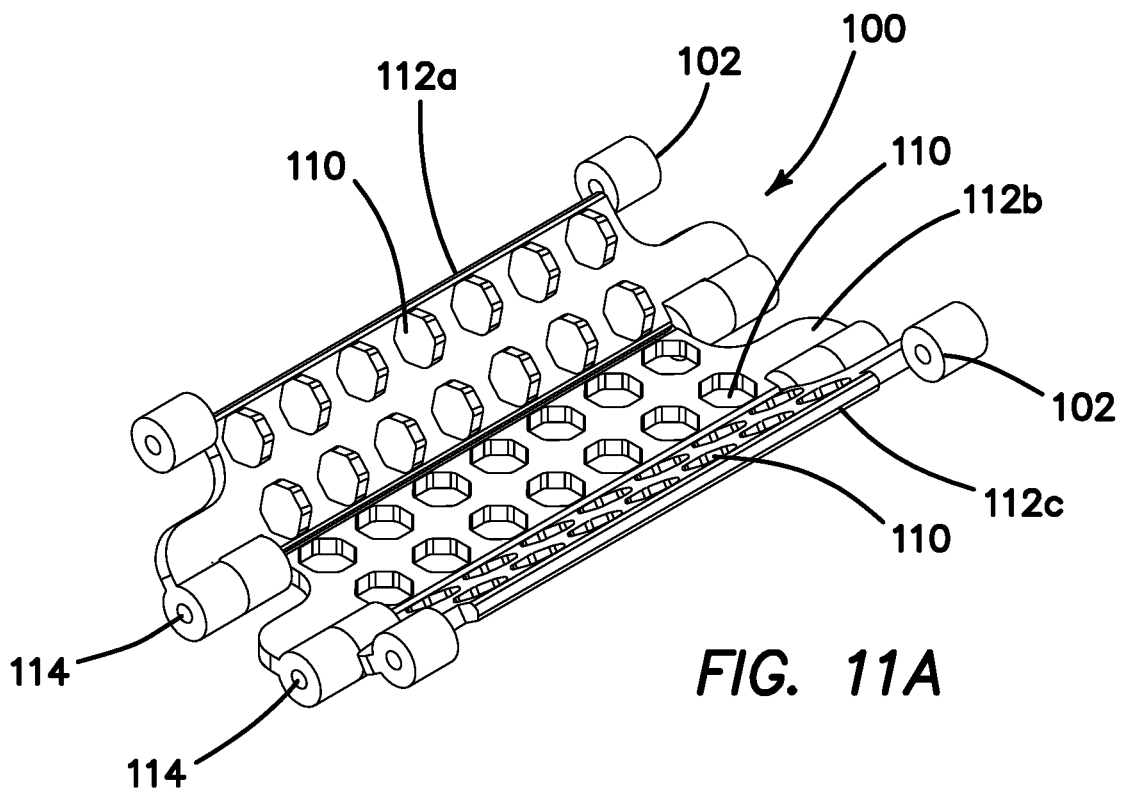
FIG. 11A is a top perspective view of a suture training model having a base with three planes hinged together according to the present invention.
Figure 11B:
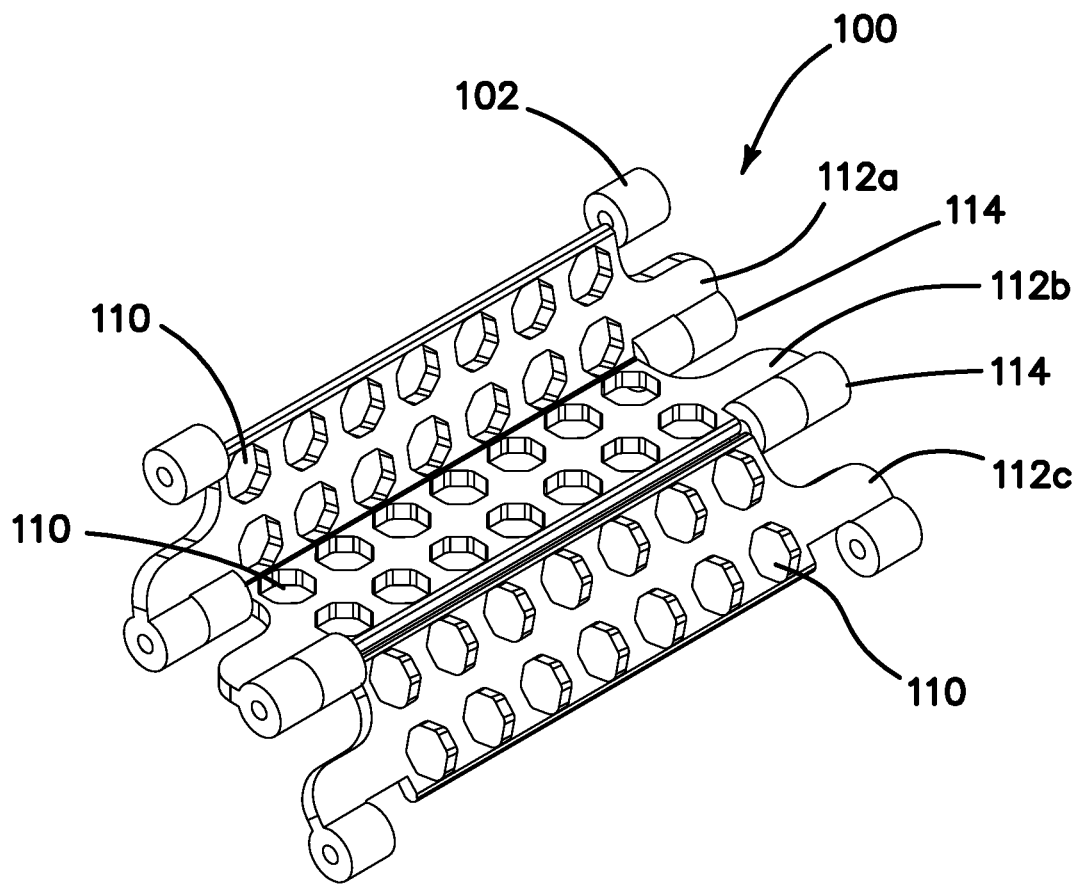
FIG. 11B is a top perspective view of a suture training model having a base with three planes hinged together according to the present invention.

Turning now to FIGS. 11A and 11B, there is shown another variation of the model 100 with a base 102 having more than one interconnected surface 112. In particular, FIGS. 11A-11B illustrate three opening-containing portions 112A, 112B and 112C interconnected by hinges 114. Each opening-containing portion 112 includes openings 110 and defines a movable surface or plane which can be arranged at an angle as desired relative to another opening-containing portion 112 to increase the difficulty of the exercise or to simulate an anatomical landscape.

Figure 12:
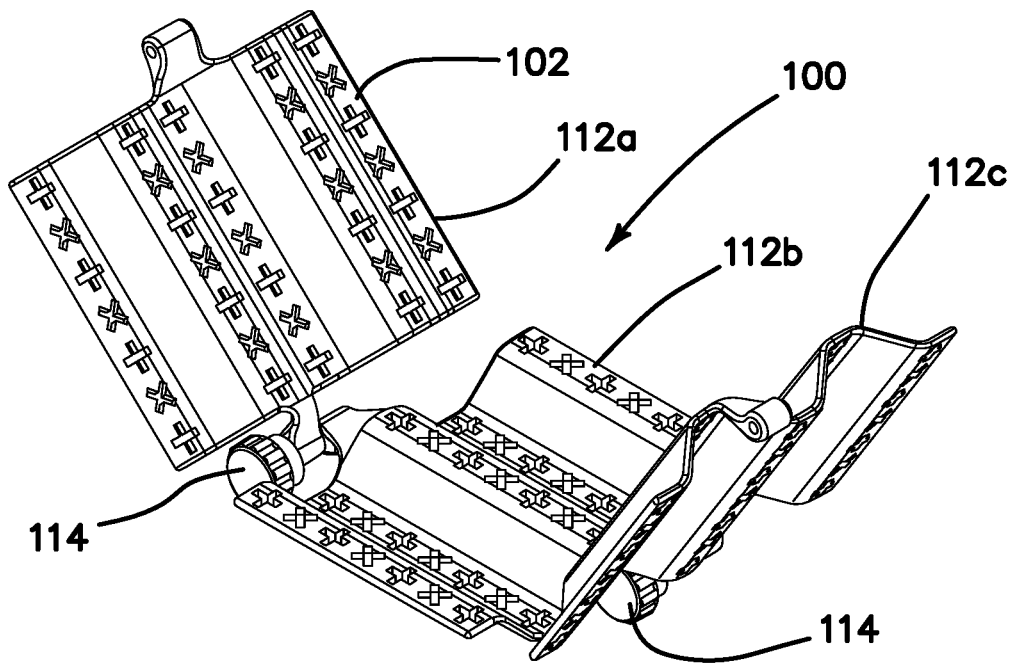
FIG. 12 illustrates a top perspective view of a suture training model having a base with three planes hinged together according to the present invention.

Turning now to FIG. 12, there is shown another variation of the model 100 with a base 102 having more than one interconnected surface 112. In particular, FIG. 12 illustrates three opening-containing portions 112A, 112B and 112C interconnected by hinges 114. Each opening-containing portion 112 includes openings 110 and defines a movable surface or plane which can be arranged and angulated as desired relative to another opening containing portion 112 to increase the difficulty of the exercise or to simulate an anatomical landscape. The variation of FIG. 12 includes complementary surfaces within each portion 112 to create a collapsible version such that one opening-containing portion 112 can fold over and into juxtaposition with another opening-containing portion 112.

Figure 13A:
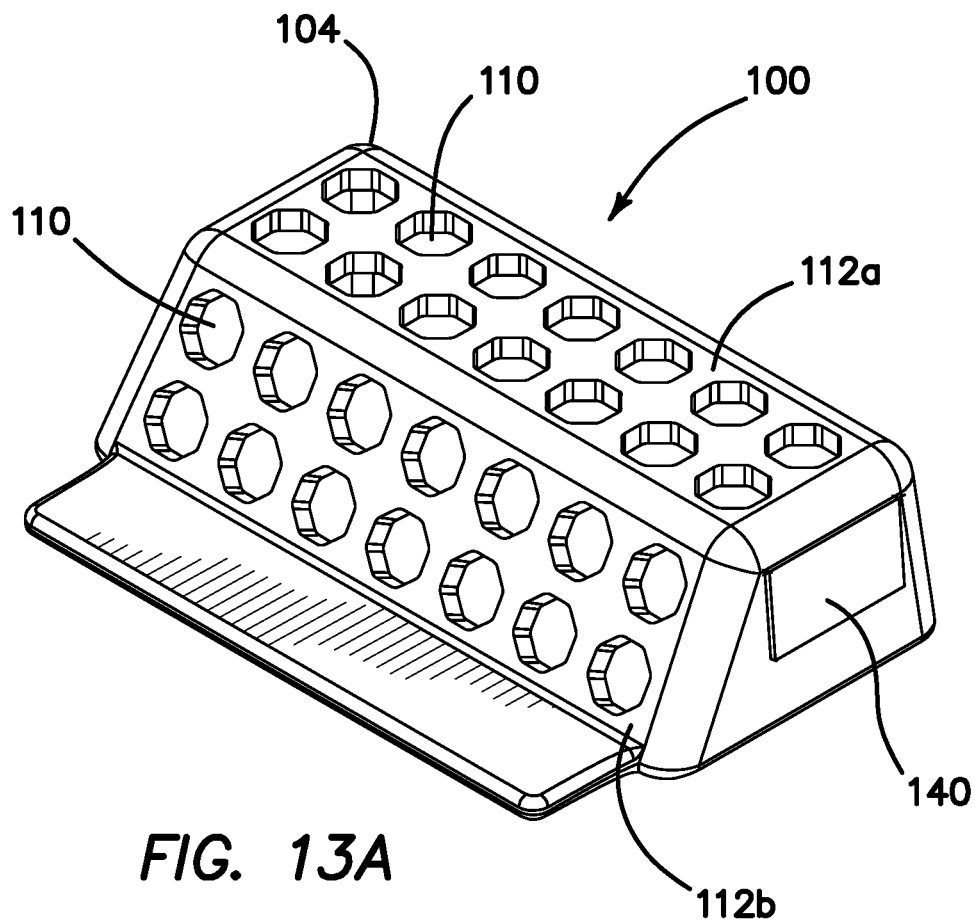
FIG. 13A illustrates a top perspective view of a suture training model according to the present invention.
Figure 13B:
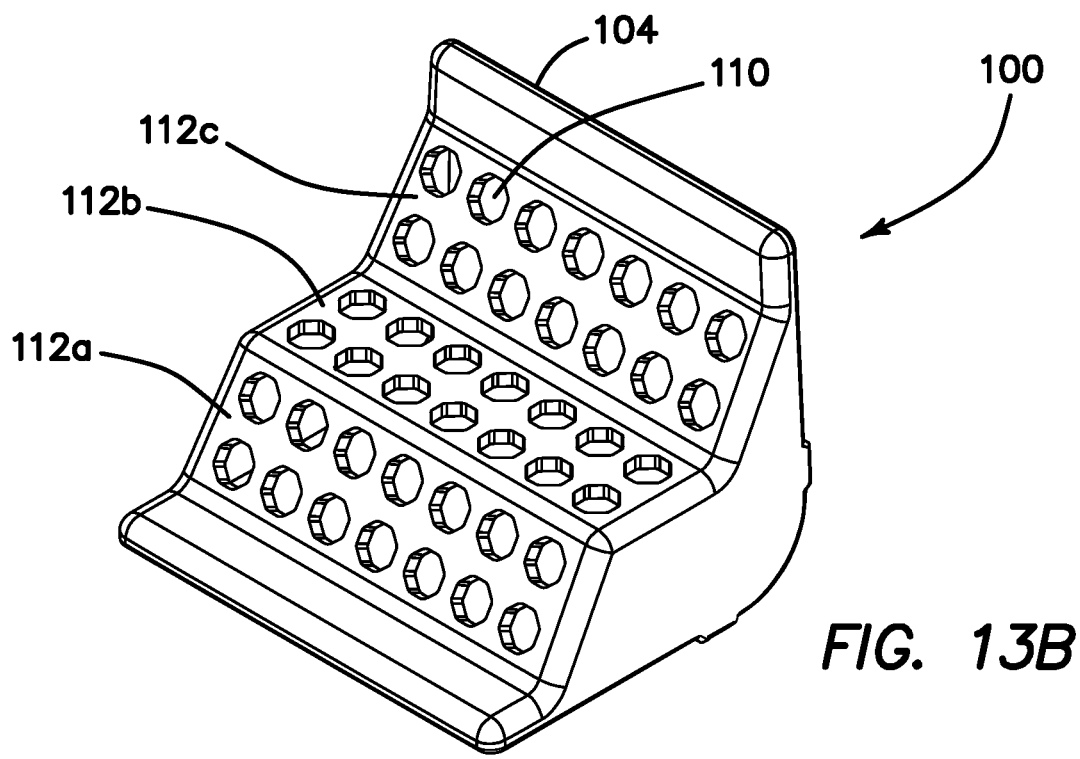
FIG. 13B illustrates a top perspective view of a suture training model in a first orientation according to the present invention.
Figure 13C:
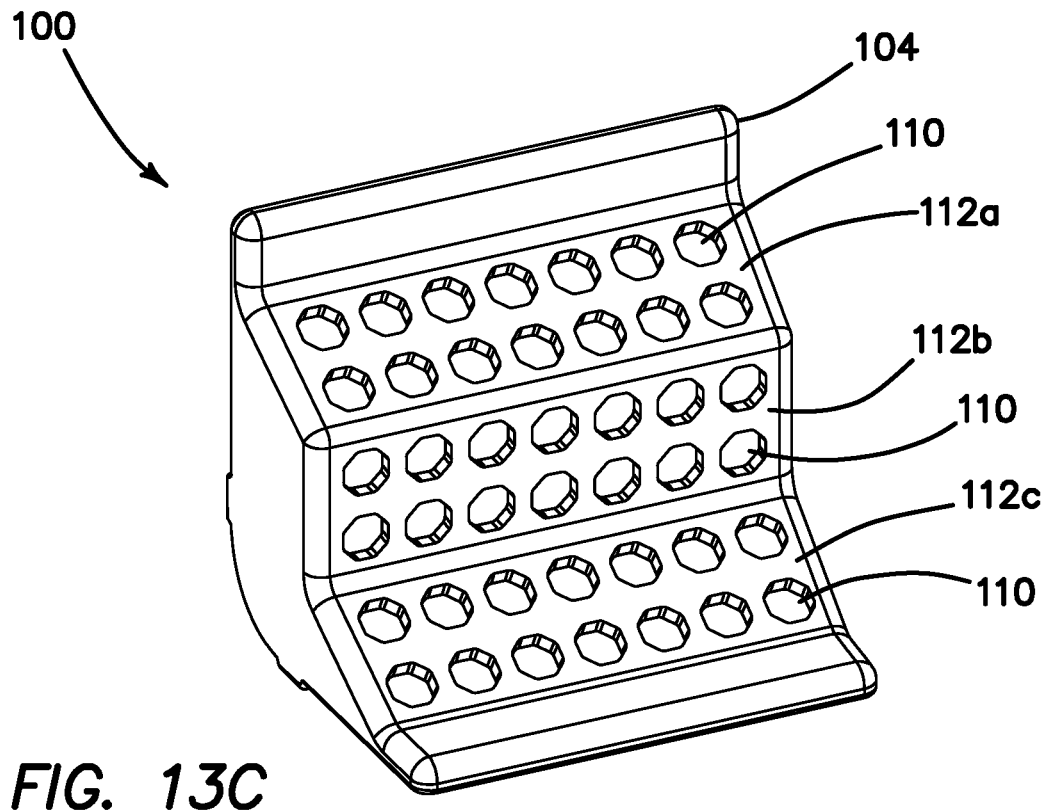
FIG. 13C illustrates a top perspective view of the suture training model of FIG. 13B in a second orientation according to the present invention.

Turning now to FIGS. 13A-13C, additional variations of the suture-passing model 100 are shown that do not have movable opening-containing portions 112. The model 100 of FIG. 13A includes two opening-containing portions 112A, 112B integrally interconnected at a predetermined angle defined between the two portions 112A, 112B as part of the base 102 of the model 100. The two opening-containing portions 112A, 112B include a plurality of openings 110 in each portion. In one variation, the angle included between the two portions 112A, 112B is greater than 90 degrees. The base 102 can be connected to the base 18 of a surgical training device 10 via a hook-and-loop type fastener 140 or other means of attachment, parts of which are attached to model 100 in one or more locations of the model 100 such that the model 100 can be removable fixed to the base 18 or other surface of a training device 10 at different orientations/angulations with respect thereto. FIGS. 13B-13C, illustrate a model 100 having three opening-containing portions 112A, 112B, 112C integrally interconnected at predetermined angles defined between the portions 112A, 112B, 112C as part of the base 104 of the model 100. The model 100 can be connected to a table top or base 18 of a surgical trainer 10 via an optional fastener 140 such as a hook-and-loop type fastener 140 in a first orientation such as shown in FIG. 13B and oriented upside-down, for example, in a second orientation such as shown in FIG. 13C to provide multiple options and angled variations for practicing suture passing with the same model 100. Also, the model 100 may be turned on one or more of its sides to provide further variation of the relative fixed angles for practice.

Figure 14A:
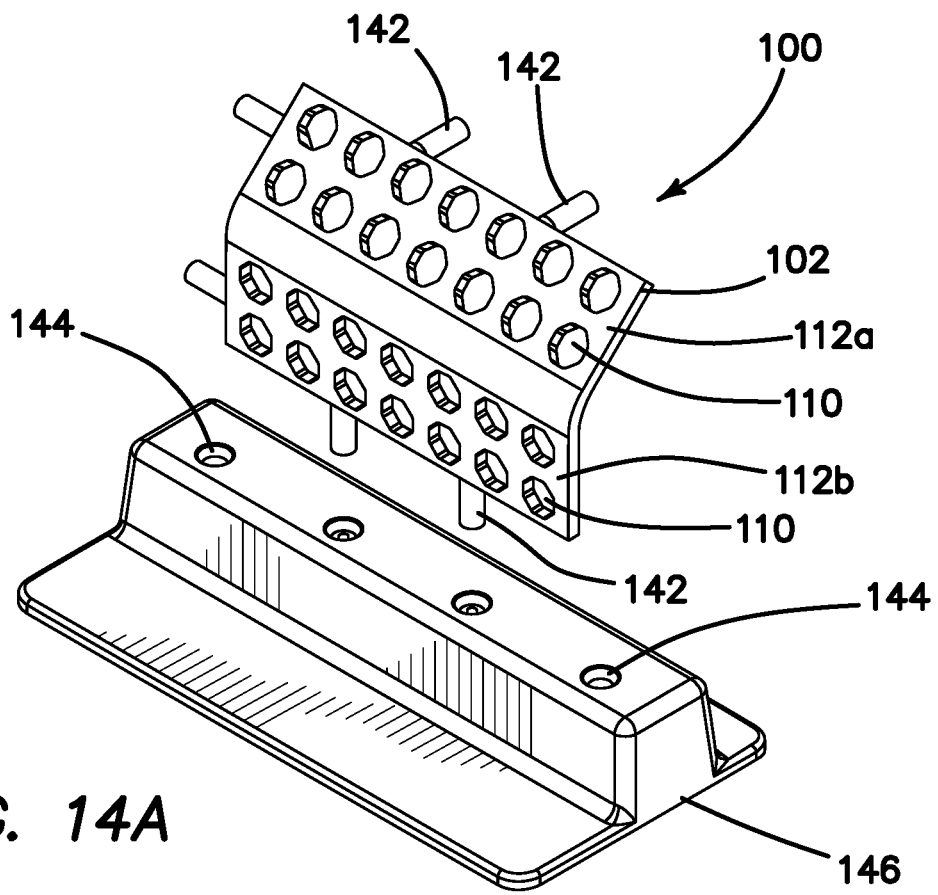
FIG. 14A illustrates a top perspective exploded view of a suture training model according to the present invention.
Figure 14B:
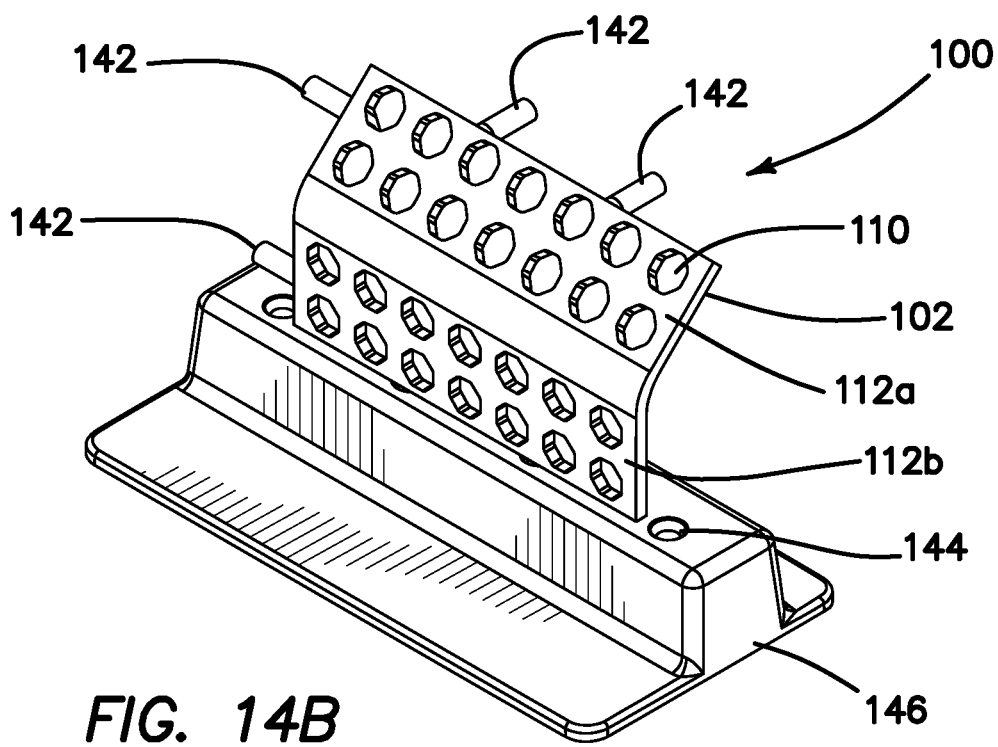
FIG. 14B illustrates a top perspective view of a suture training model according to the present invention.

Turning now to FIGS. 14A-14B, there is shown another variation of the suture passing model 100 according to the present invention. The model 100 includes a base 102 containing a plurality of openings 110. The base 102 may further include one or more connected opening-containing portions 112 that are angled with respect to each other. In FIGS. 14A-14B, the base 102 includes two opening-containing portions 112A, 112B that are angled with respect to each other. The model 100 further includes pegs along the periphery of the base 102 that are sized and configured to be inserted into holes 144 formed in a stand 146. The stand 146 is configured to hold the base 102 in an upright and stable orientation with respect to a table top or other surface such as a base surface 18 in a surgical trainer 10. The base 102 is removable with respect to the stand 146 so that the base 102 can be oriented in another direction by inserting a different set of pegs 142 on another side of the base 102 into the holes 144 in the stand 146. FIG. 14A illustrates the base 102 disconnected from the stand 146 and FIG. 14B illustrates the base 102 connected to the stand 146. The holes 144 in the stand 146 are configured to receive the pegs 144 and to hold the base 102 steady in any of its orientations with respect to the base so that suture training exercises can be performed. The base 102 in FIGS. 14A-14B illustrates an integrally angled base 102 having two or more suture planes 112A, 112B. In another variation, the base 102 may include more than one suture planes 112A, 112B that are connected together via a hinge.

Figure 15A:
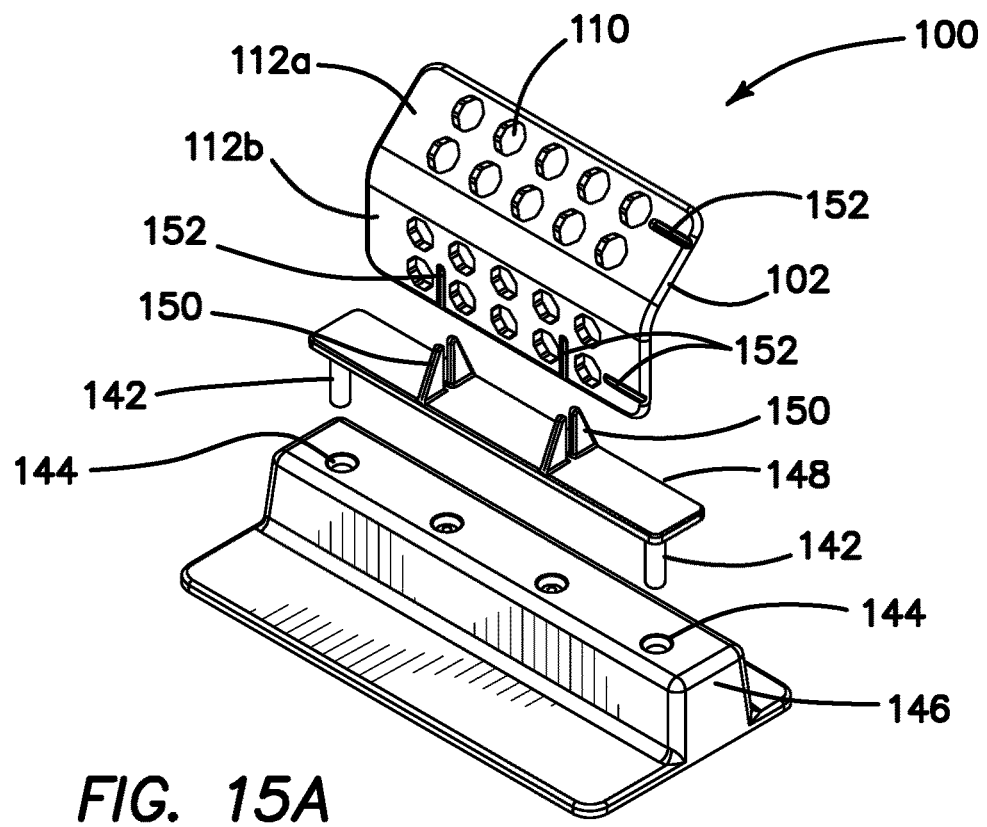
FIG. 15A illustrates a top perspective exploded view of a suture training model according to the present invention.
Figure 15B:
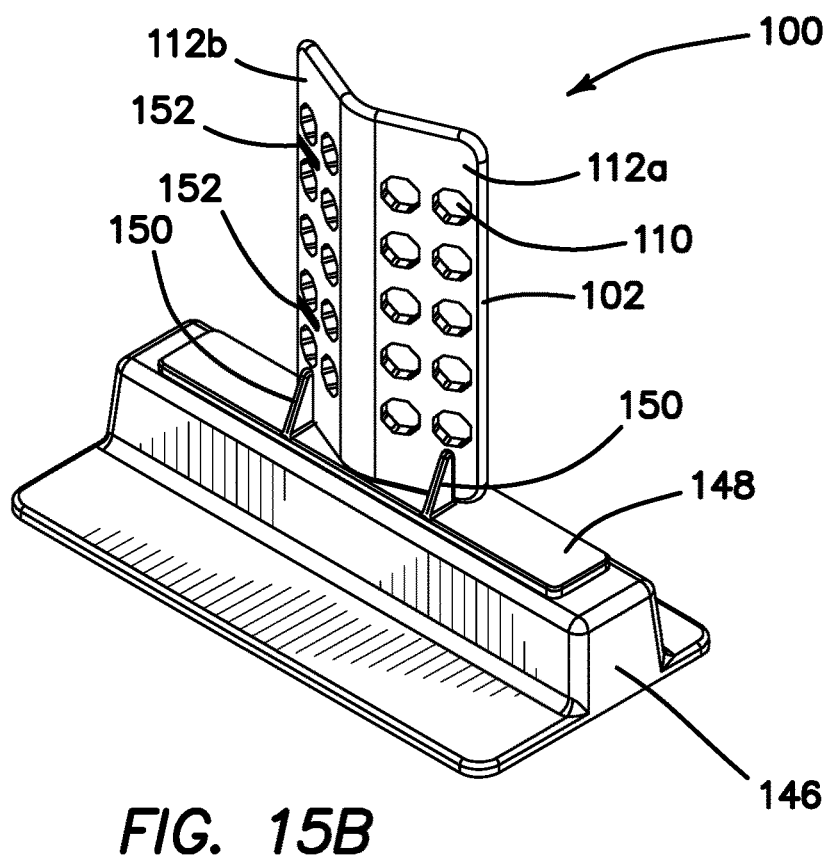
FIG. 15B illustrates a top perspective view of a suture training model according to the present invention.

Turning now to FIGS. 15A-15B, illustrates another variation of the suture training model 100. The model 100 includes a base 102 having a plurality of openings 110 arranged on one or more opening-containing portions 112. The variation of FIGS. 15A-15B contains two opening-containing portions 112A, 112B that are integrally formed at an angled with respect to each other. They may also be formed such that the two or more opening-containing portions 112 are movable with respect to each other to adjust the angles between the opening-containing portions 112. The model 100 includes a stand 146 having a plurality of holes 144 configured to mate with pegs 142 of a holder 148. The holder 148 is configured to snap into the stand 146 and to hold the base 102. The holder 148 includes at least one upstanding mouth 150 defining a gap into which notches 152 formed in the base 102 can mate and be received to hold the base 102 in an upright orientation with respect to the stand 146 which is configured to support the base 102 on a flat table top surface or other surface such as a base 18 in a surgical trainer 10. The base 102 includes a plurality of notches 152 formed around the periphery such that the base 102 can be oriented in multiple directions. For example, in FIG. 15A, the notches 152 on one side of the base 102 are engaged with the mouth 150 of the holder 148 to orientate the base 102 in a horizontal position. In FIG. 15B, the notches 152 on another side of the base 102 are mated with the gaps of the mouth 150 of the holder 148 to orientate the base 102 in a vertical position. With multiple orientations, a single model 100 is capable of providing variations in training for the passage of sutures through planes at different angles and orientations.

The suture training model 100 provides a flexible training platform that allows users of all skill levels to practice suturing and suture passing techniques. The model 100 employs flexible suture tabs 104 and an adjustable base 102 that can be configured and reconfigured depending on the technical skill of the user and the desired type of practice. The model 100 consists of a base 102 that contains a plurality of openings through which the suture tabs 104 are placed and can be pulled. The base 102 can be a single object with no moving parts or an object with multiple adjustable surfaces or planes. The suture tabs 104 have a wider stopper base 134 which prevents the suture tabs 104 from being pulled through the openings 110. The openings 110 in the base 102 can be a number of different shapes including slots, x-shapes, hexagons, octagons etc. Similarly, the suture tabs 104 can be a variety of shapes and sizes. Furthermore, the suture tabs 104 can contain one or more hole or slot 126 through which the suture is passed. Other tabs have neither a slot nor a hole 126 but provide a penetrable region and can be used alone or in conjunction with the slotted tabs to provide a greater challenge and more realistic simulation. In one practice scenario, the user targets the slotted tab 104 and avoids the aperture-less tab 104 and in another practice scenario, the user passes a suture through the aperture-less tab and avoids the slotted tab 104. In yet another practice scenario, the user may pass a suture through both tabs whether one or more of them contain apertures 126 or not. This practice requires the user to pull both adjacent tabs and carefully pass the target and pass the suture. The shape of the opening 110 in the base 102 determines the orientation of the tabs 104 relative to the base 102. The shape of the opening 110 and, hence, the orientation of the suture tab is predetermined relative to other openings 110 in one configuration of the base 102 and as such can be customized for predefining a suture pathway encountered in real surgery. In another variation, a single opening 110 has multi-directional orientation possibilities for a suture tab 104 permitting the user to orientate the tabs as desired or according to a manual designating various possible pathways for practicing various difficulty levels, test or anatomical situations and procedures. Because the suture tabs 104 are made of elastomeric material, when the tab 104 is manipulated with laparoscopic graspers or dissectors, the user can advantageously stretch the aperture 126 to a more open position through which the suture need can be passed. Because the apertures 126 are not at rest in an open position and the tab 104 tends to spring back to an unbiased, unstretched position, the user is forced to use both hands in concert to complete the exercise. Using one hand to keep the tab stretched in an aperture-open configuration and the other hand to pass the needle through the aperture 126 while it is in an open configuration. The suture passing exercise provided by the model 100 is open to the interpretation of the user. By providing a number of openings 110 through which to place the tabs 104 as well as providing an adjustable base 102, the device 100 can be used to challenge users of a range of skill levels. Furthermore, the exercise can be reconfigured to simulate specific anatomy of interest to a practitioner. Also, the size and shape of the tabs and their respective slots increases the challenge of the exercise. With the suture training model 100, the user must manipulate the tab in order to sufficiently open the aperture 126 in order to pass the suture through said aperture 126. This added dimension increases the challenge and realism of the simulation. Having tabs 104 of various shapes and sizes as well as the configuration in which they are placed on the base 102 provides for varying degrees of difficulty for the exercise. Larger tabs 104 with pre-formed holes are the easiest. The user can graduate to tabs 104 that have slots which require the use of two hands in order to turn the slot into a hole and pass the suture through. The small slot may be a line cut through the tab 104. The smaller the aperture 126, the higher level of precision is required in order to successfully complete the exercise. The addition of tabs 104 with no apertures 126 further increases the level of proficiency needed in order to avoid surrounding tissue while accessing the target anatomy with a suture. Furthermore, side-by-side placement of tabs with or without apertures 126 also increases the difficulty level of practice. Tabs 104 with no aperture 126 are used for a higher level of fidelity where the user must practice driving the needle through the tissue itself rather than a preformed aperture 126.

Figure 16A:
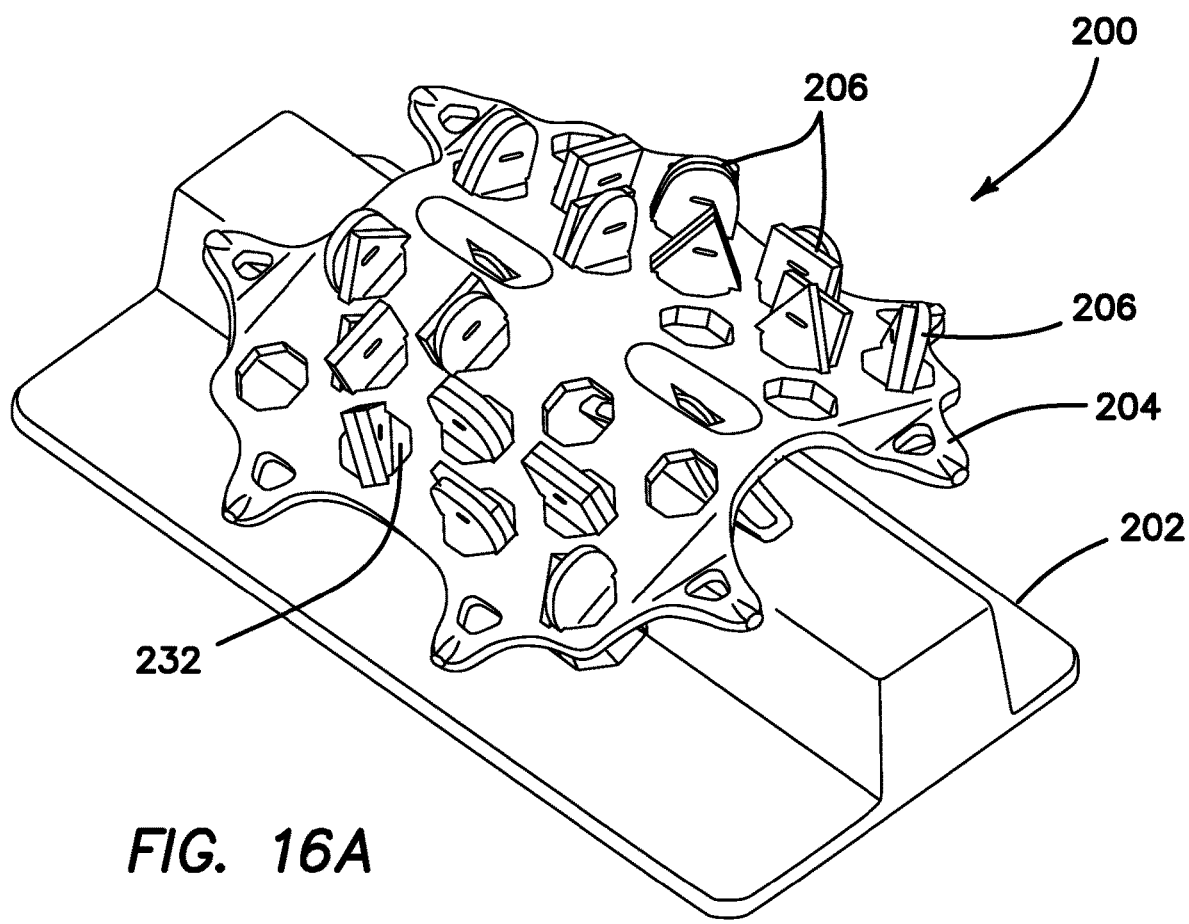
FIG. 16A illustrates a top perspective view of a suture training model according to the present invention.
Figure 16B:
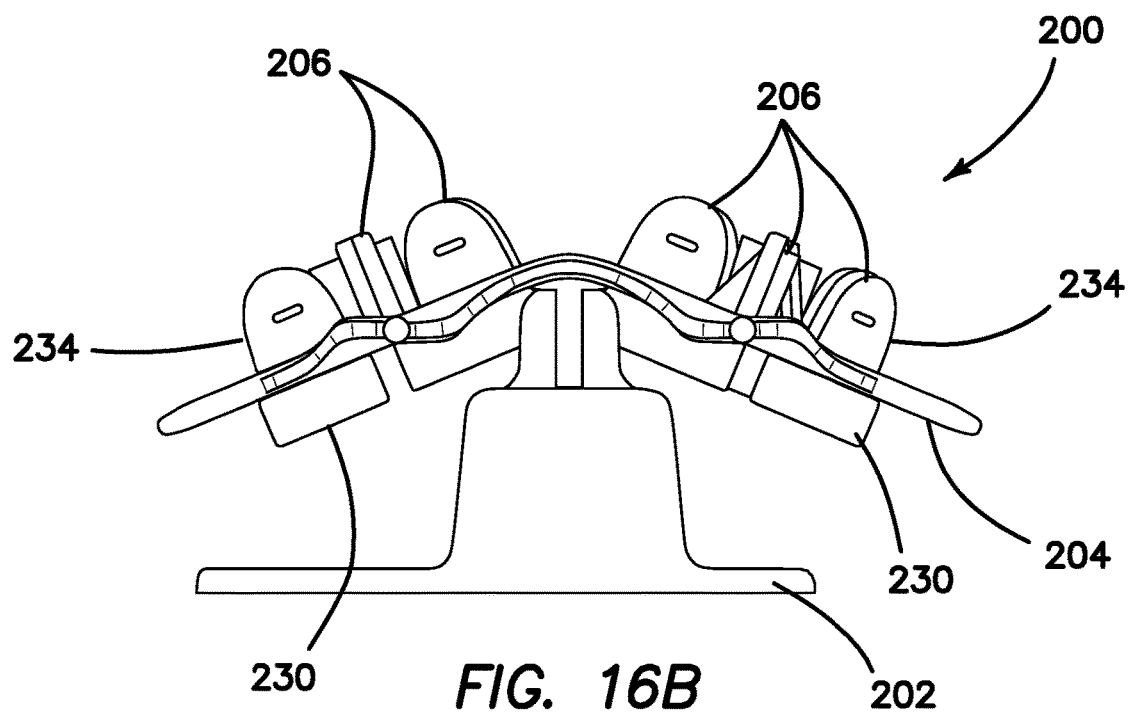
FIG. 16B illustrates a side elevational view of a suture training model of FIG. 16A according to the present invention.
Figure 16C:
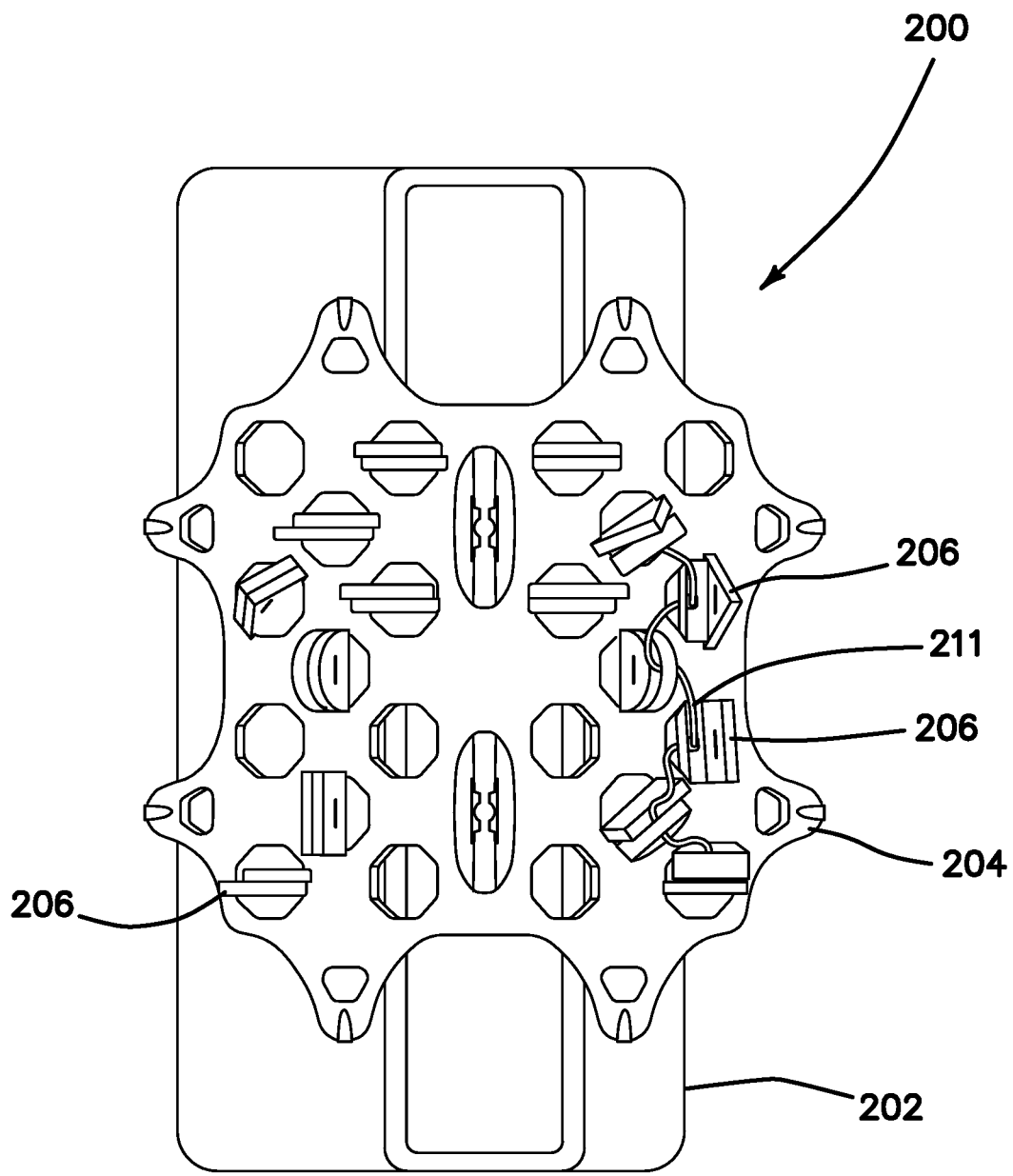
FIG. 16C illustrates a top view of the suture training model of FIG. 16A and a suture passed therethrough according to the present invention.
Figure 21A:
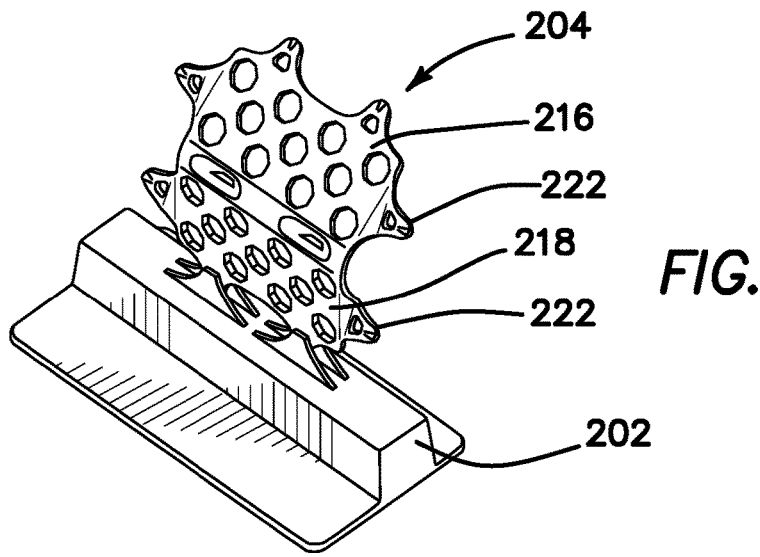
FIG. 21A illustrates a top perspective view of the base of FIG. 20 connected to a base in a first orientation according to the present invention.
Figure 21B:
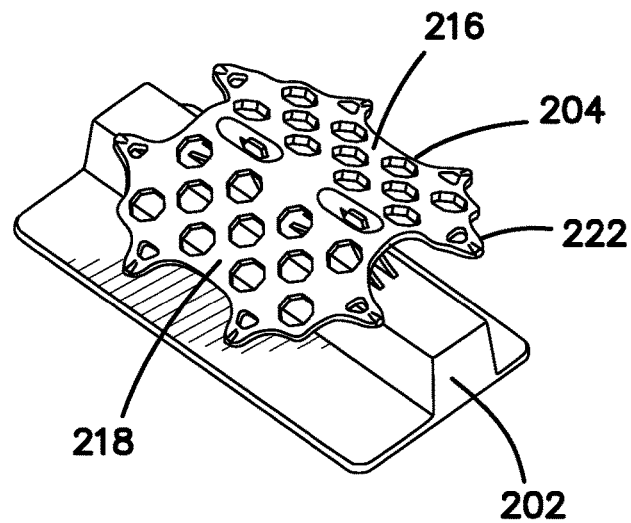
FIG. 21B illustrates a top perspective view of the base of FIG. 20 connected to a base in a second orientation according to the present invention.
Figure 21C:
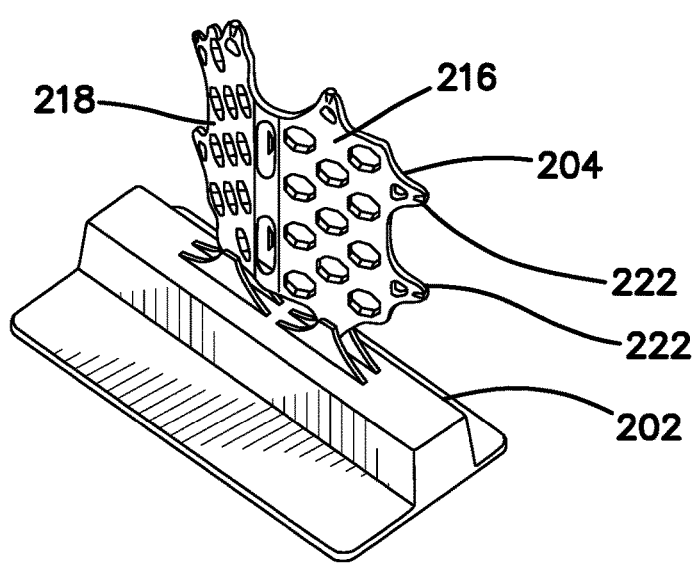
FIG. 21C illustrates a top perspective view of a base of FIG. 20 connected to a base in a third orientation according to the present invention.
Figure 23A:
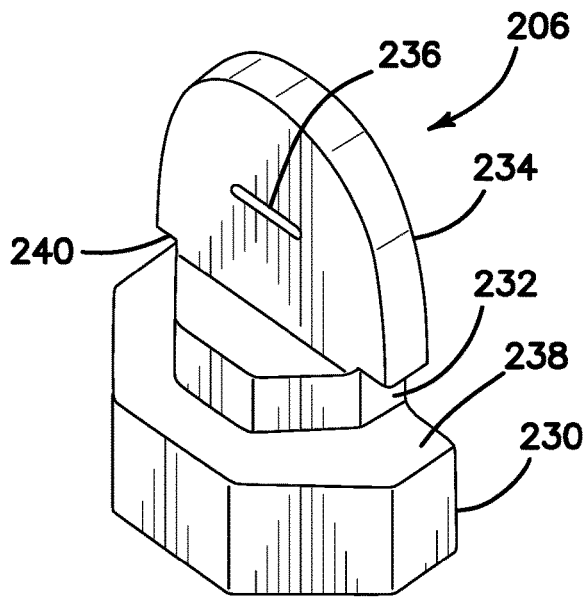
FIG. 23A illustrates a top perspective view of a tab according to the present invention.
Figure 23B:
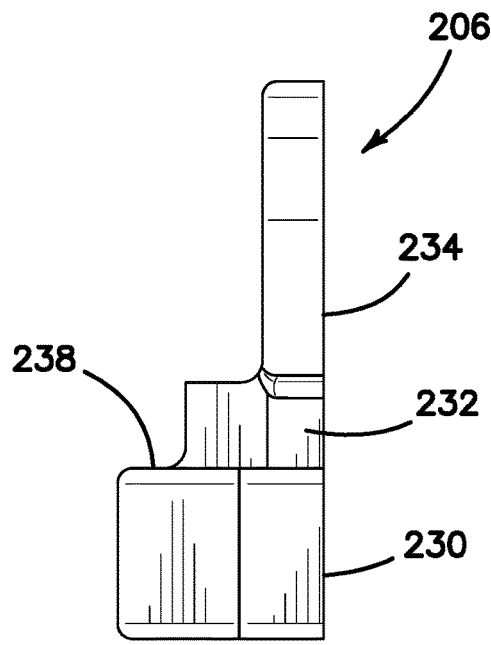
FIG. 23B illustrates a side elevational view of the tab of FIG. 23A according to the present invention.
Figure 23C:
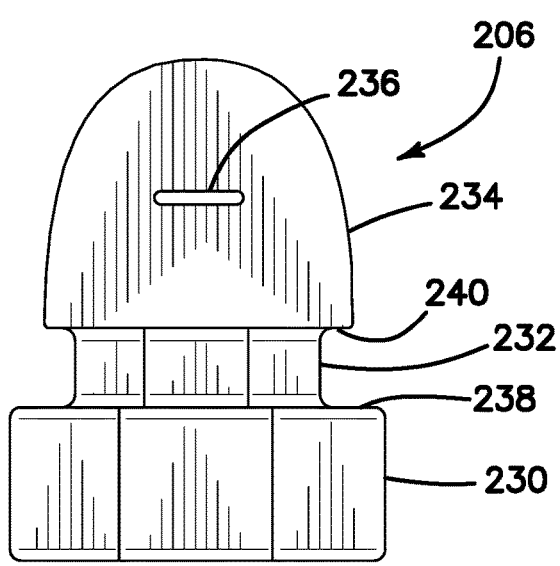
FIG. 23C illustrates a front elevational view of the tab of FIG. 23A according to the present invention.
Figure 23D:
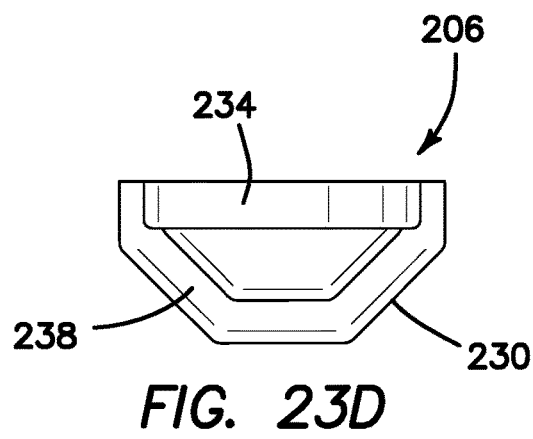
FIG. 23D illustrates a top view of the tab of FIG. 23A according to the present invention.
Figure 24A:
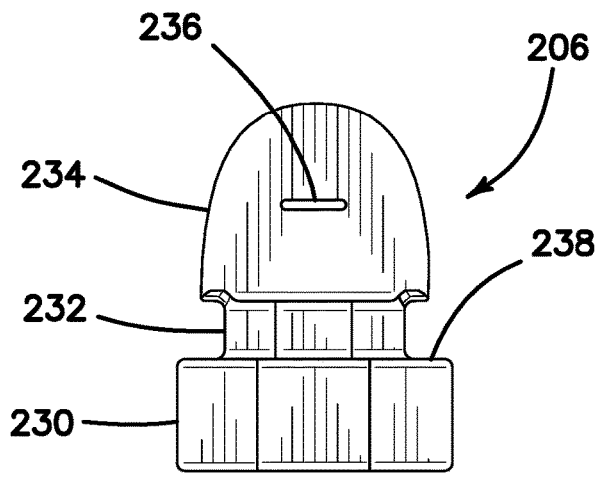
FIG. 24A illustrates a front elevational view of a tab in a first configuration according to the present invention.
Figure 24B:
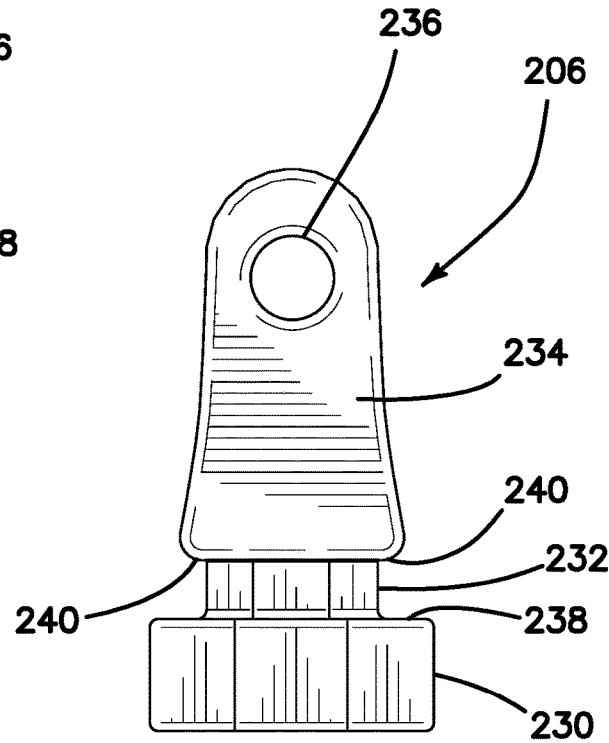
FIG. 24B illustrates a front elevational view of the tab of FIG. 24A in a second configuration according to the present invention.

Turning now to FIGS. 16A-16C, there is shown another variation of a suture training model 200. The model 200 includes a stand 202, a base 204, and one or more tabs 206. The stand 202 supports the base 204. The base 204 attaches to the stand 202 and may support the base 204 in a variety of orientations as shown in FIGS. 21A-21C. The one or more tabs 206 connect to the base 204 in a variety of orientations. The one or more tabs 206 are configured such that a suture and needle may pass through the one or more tabs 206. A suture 211 is shown in FIG. 16C passing through several tabs 206. The suture training model 200 is configured to be easily placed into and removed from inside the cavity 12 of a surgical training device 10. Alternatively, the model 200 may be used outside a training device 10 to practice suture passing. The stand 202 is configured to support the base 204 and tabs 204 and withstand forces exerted by the user during the passing of needle and suture without toppling over or responding in a manner that is not realistic when manipulated. The model 200 is configured to be secure enough to withstand such forces applied during suturing, including tying knots, pulling and pushing. The base 204 is easily connected and disconnected from the stand 202 to change the orientation of the base 204 with respect to the stand 202 and/or for portability purposes. Tabs 206 are removably connected to the base 204 so that used tabs 206 may be replaced with new tabs 206 after use if needed. Tabs 206 are configured to receive sutures 211 passed with a needle and/or other instrument and withstand forces applied during suturing, typing knots, and inadvertent or intentional pushing, pulling or rotating in multiple directions. The base 204 has a plurality of tab receiving locations such as apertures 220 providing a multitude of options for suture pathways and orientations offering varying levels of difficulty for simulated operations.

Figure 17A:
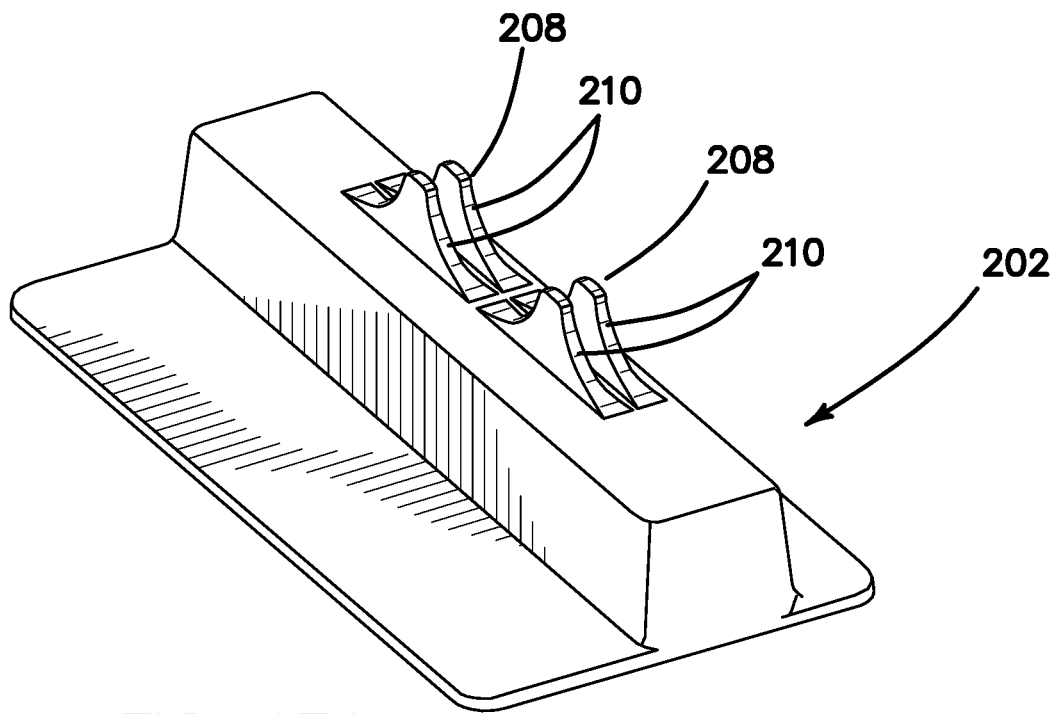
FIG. 17A illustrates a top perspective view of a base according to the present invention.
Figure 17B:
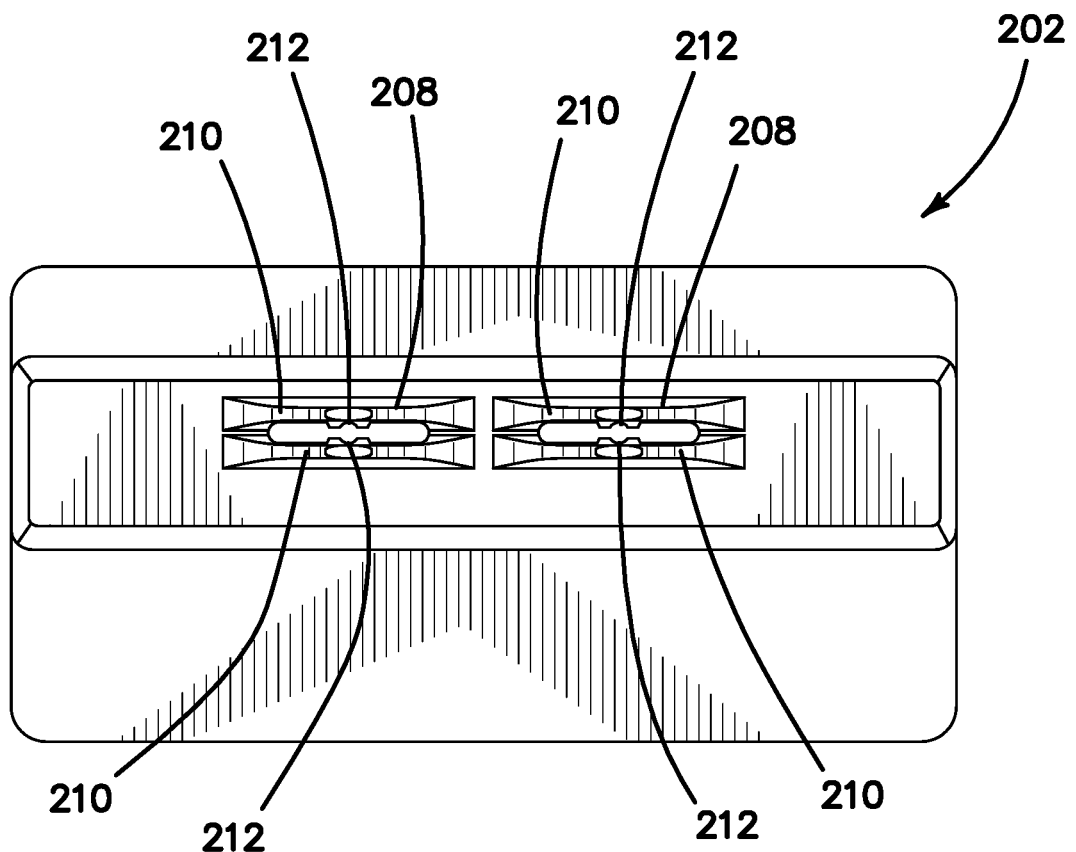
FIG. 17B illustrates a top view of the base of FIG. 17A according to the present invention.
Figure 18A:
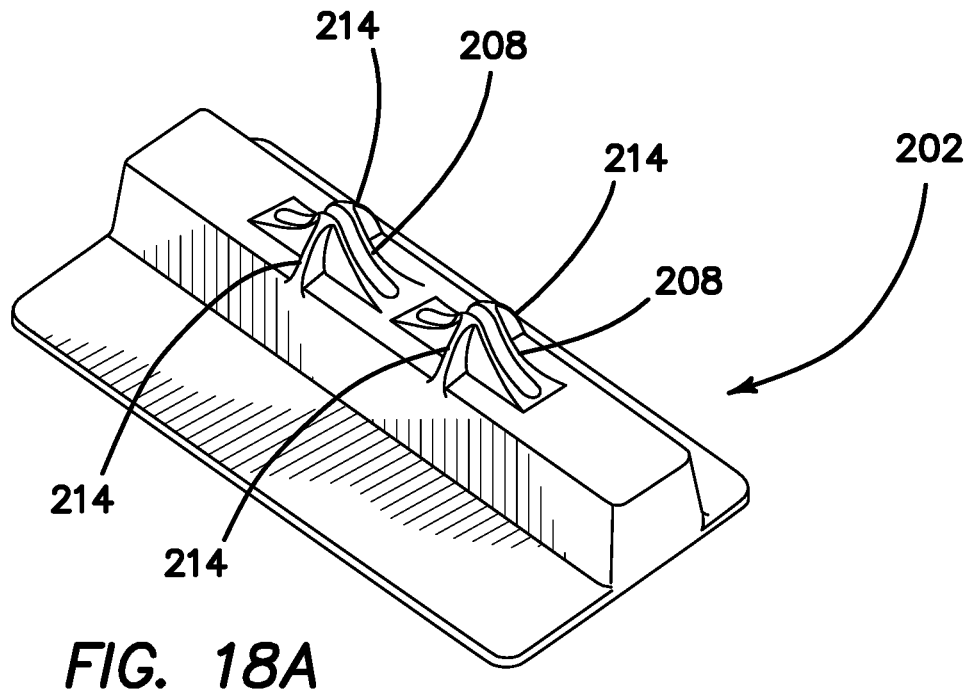
FIG. 18A illustrates a top perspective view of a base according to the present invention.
Figure 18B:
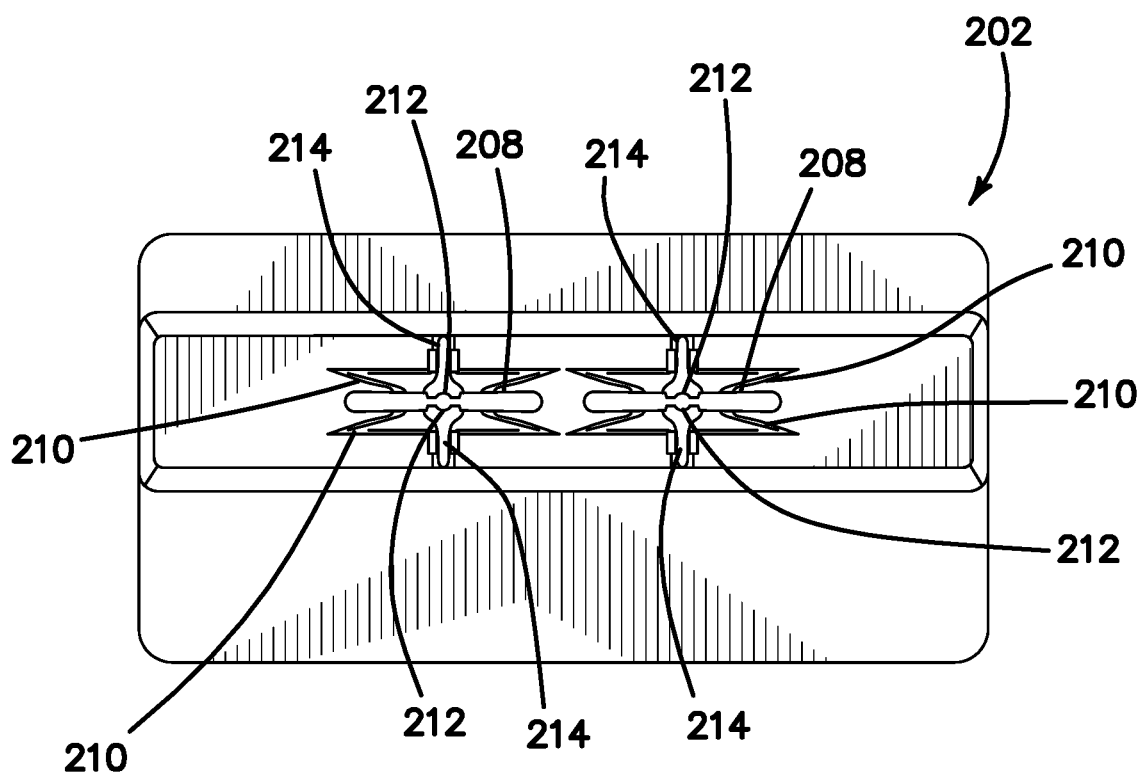
FIG. 18B illustrates a top view of a base of FIG. 18A according to the present invention.
Figure 19:
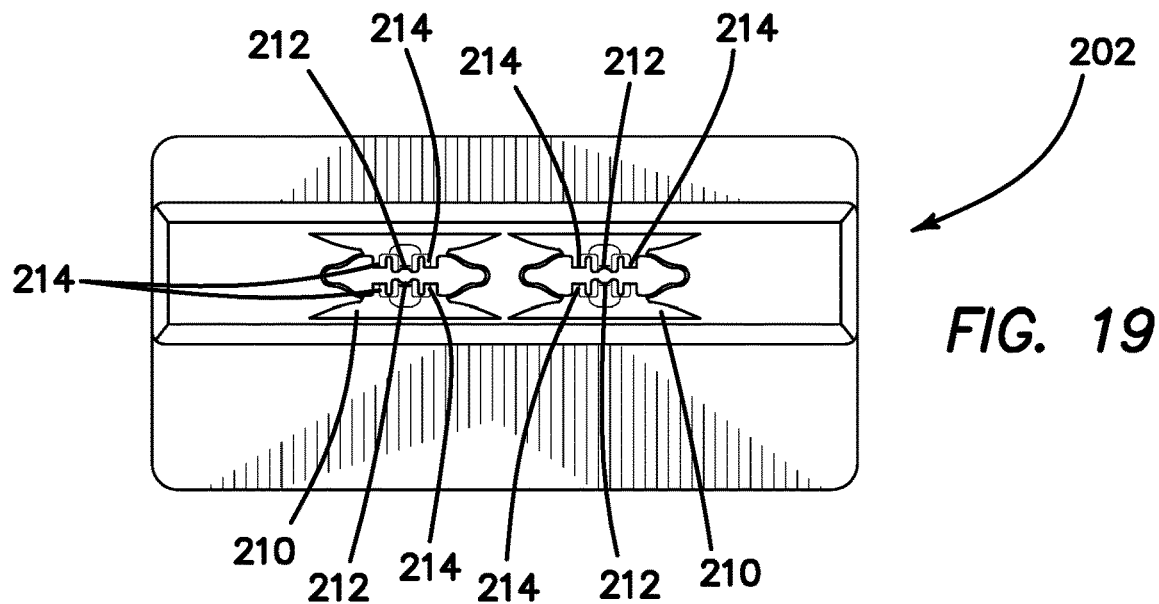
FIG. 19 illustrates a top view of a base according to the present invention.

Turning now to FIGS. 17A-17B, there is shown a stand 202 according to the present invention. The stand 202 includes a planar bottom surface for placement on a flat surface such as the base 18 of a surgical training device 10 or table top. The bottom surface is interconnected with a top surface that includes at least one upstanding clip 208. FIGS. 17A-17B illustrate a stand 202 with two clips 208 that are aligned and spaced apart from each other. Each clip 208 includes two finger-like projections 210 spaced apart from and facing each other to create a gap for receiving a portion of the base 204 within the gap. The facing surfaces of the projections 210 include features such as a channel 212 for guiding and receiving the base 204 and features for connecting with the base 204 such as in a snap-fit, friction-fit or other engagement. The features are not limited to the channel 212, clips, or any other structure that interacts with base 204 and facilitates connection therewith. In one variation, the base 204 includes complementary clip adapters that interact with the clips 208 to secure the base 204 to the base 200. One or more of the finger-like projections 210 may be provided per clip 208. In one variation, the one or more finger-like projections 210 includes one or more reinforcing rib 214 located on the outside surface of the projection 210 as shown in FIGS. 18A-18B or on the inside surface of the projection 210 as shown in FIG. 19. The reinforcing rib 214 of FIGS. 18A-18B is substantially perpendicular to the outer surface of the projection. The reinforcing rib 214 may also be oriented vertically on the outside surface or inside surface as shown in FIG. 19. The reinforcing rib 214 is configured to increase the rigidity of the projection 210 and prevent over-flexion of the base 204 when manipulated. The reinforcing rib 214 is connected or attached to or integrally formed with the projection 210.

The stand 202 is made of rigid material. In one variation, the stand 202 is configured to securely attach to the base 18 of a surgical training device 10 with hook-and-loop type fastening material. In such a variation, the bottom surface of the stand 202 includes one side of the hook-and-loop type fastening material facing outwardly. A complementary piece of hook-and-loop type fastening material is connected to a surface of the base 18 of the surgical training device 10. Other means are within the scope of the present invention for removably attaching the model 200 to a surface of the trainer 10 in order to secure the model 200 during use.

Figure 22:
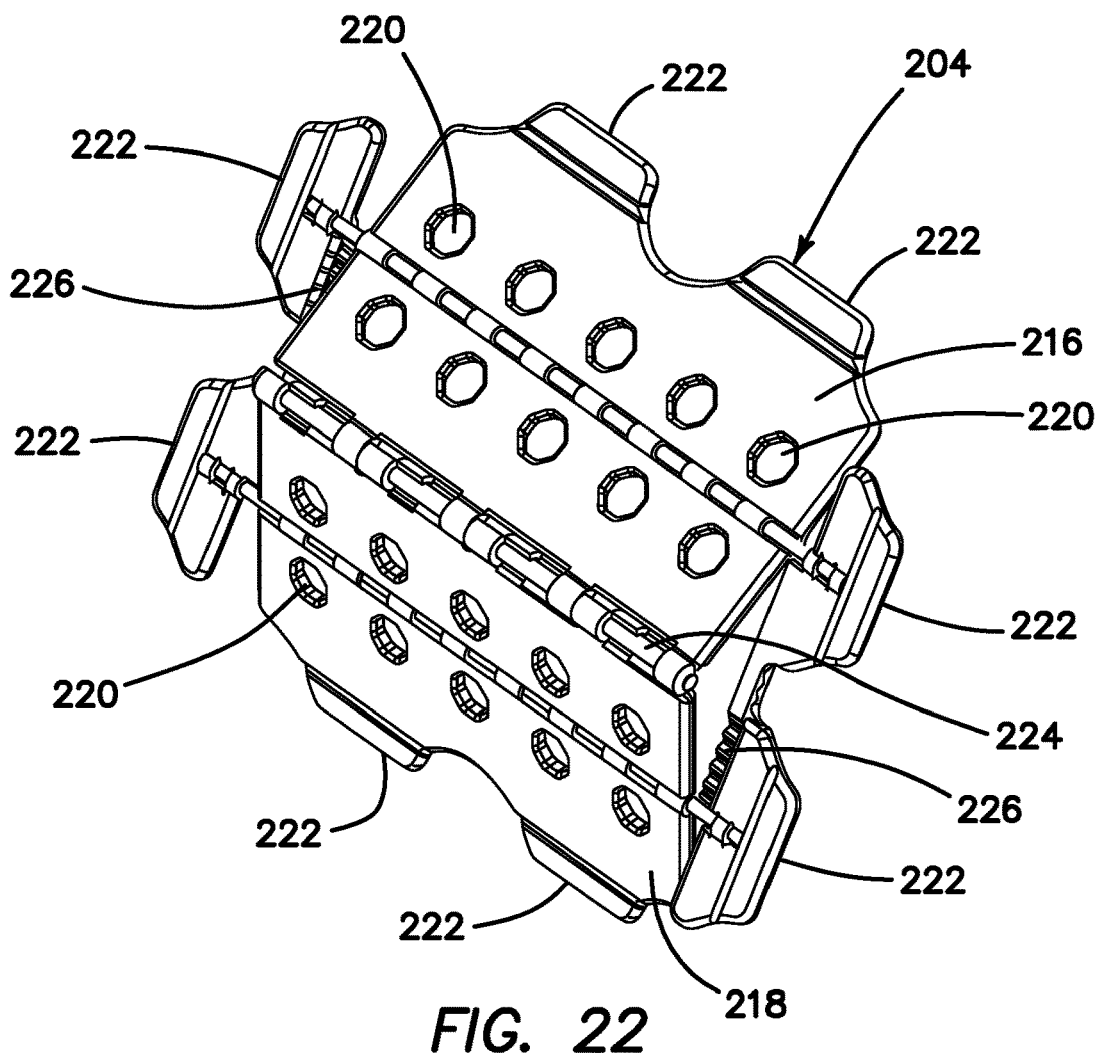
FIG. 22 illustrates a top perspective view of a base according to the present invention.
Figure 20A:
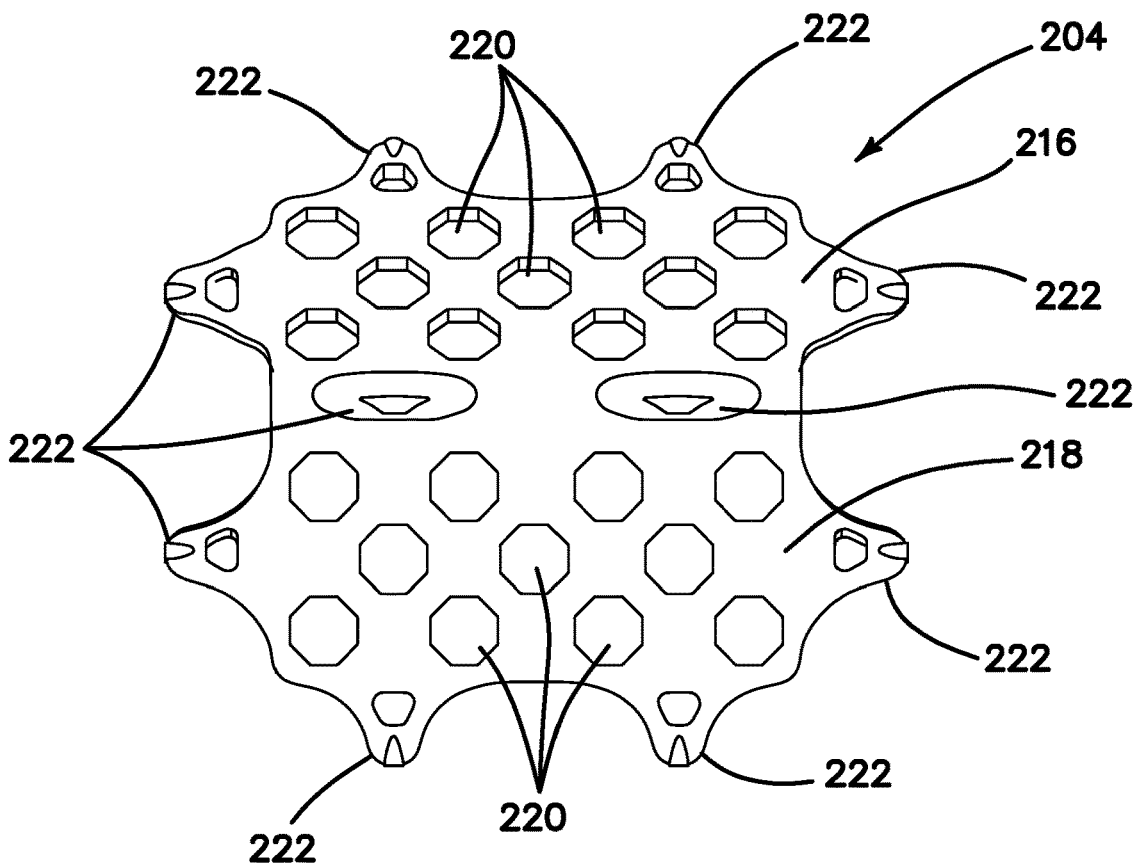
FIG. 20A illustrates a top view of a base according to the present invention.
Figure 20B:
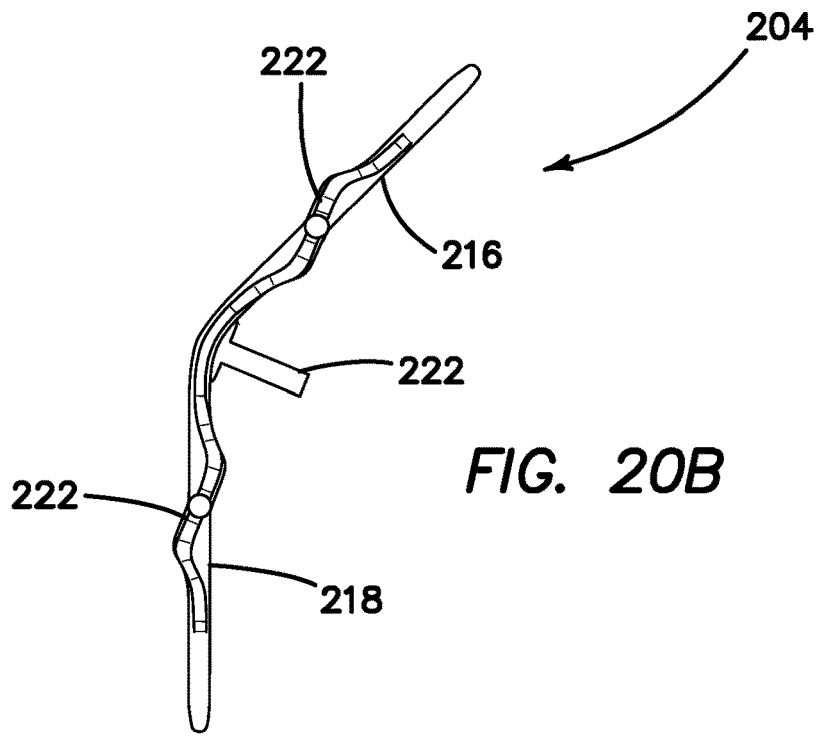
FIG. 20B illustrates a side view of the base of FIG. 20A according to the present invention.

Turning now to FIGS. 20-22, the base 204 will now be described. The base 204 is made of rigid material and has two operational planes 216, 218 angled with respect to each other. The angled planes 216, 218 are connected at a common intersection in one variation. In another variation, the angle between the two planes 216, 218 is approximately 120 degrees. Any number of operational planes 216, 218 may be provided with each plane serving as a simulated tissue plane such that suture passing may be practiced across the angled surfaces. The base 204 has a top surface and a bottom surface defining a thickness therebetween. A plurality of apertures 220 are formed in the base 204 through the top surface and bottom surface. These apertures 220 may have any shape suitable for receiving tabs 206 in a variety of directions, orientations, angulations to provide a variety of suture pathways which will be described in greater detail below. In the variation shown, the apertures 220 are polygonal in shape, in particular, they are octagonal. The base 204 further includes a plurality of mating surfaces 222 configured for connection with the clips 208 on the stand 202. In one variation, the mating surfaces 222 are extensions paired for direct engagement with the pair of clips 208 on the stand 202. The mating surfaces 222 may include apertures for snapping into the clips and/or ribs for slidably mating within the channel 212 in the clips 208. A plurality of mating surfaces 222 along the edges of the base 204 is provided so that the base 204 may be connected to the stand 202 in any number of orientations. Also, mating surfaces 222 may be provided as extensions from the top surface or the bottom surface of base 204 to further increase the number of possible orientations. Various orientations of the base 204 with respect to the stand 202 are shown in FIGS. 21A-21C. Three orientations of the base 204 are shown in FIGS. 21A-21C. In one variation, pairs of mating surfaces 222 are provided along at least three locations on the base 204. For a sloped conformation of the base 204, mating surfaces 222 that are located along the straight edge of the base 204 are snapped into the clips 208 as shown in FIG. 21A. For a corner conformation of the base 204, mating surfaces 222 that are located along the angled edge of the base 204 are snapped into the clips 208 as shown in FIG. 21C. For a turtle-back-like conformation of the base 204 with respect to the stand 202, the mating surfaces 222 that are located on the bottom surface of the base 204 are snapped into the clips 208.

With reference to FIG. 22 another variation of the base 204 is shown. In this variation of the base 204, a hinge 224 is provided between the two planes 216, 218 to connect them in a manner such that the angle between the two planes 216, 218 is adjustable. The angle between the two planes 216, 218 is fixed with the help of a ratchet 226 provided on one or more sides of the base 204 and located between the two planes 216, 218 and the mating surfaces 222. The mating surfaces 222 are connected to the ratchet 226 such that they are suitably adjusted with a change in the angle between the two planes 216, 218. The mating surfaces 222 are elongate flat tabs configured to connect with the clips 208 on the stand 202. The hinged variation of the base 204 of FIG. 22 allows for a variety of planar angles for suturing practice.

Turning now to FIGS. 23A-27, the tabs 206 will now be described in greater detail. Each tab 206 includes a tab base 230 interconnected with a tab face 234 by a tab neck 232. The tab base 230 has a shape in a cross-section taken perpendicular to the longitudinal axis of the tab 206 that substantially matches the shape or half the shape of the aperture 220 in the base 204 in which it is to be located. The tab base 230 is sized slightly larger than the apertures 220 and configured such that the tab base 230 can be inserted and removed from an aperture 220. When inserted into an aperture 220, the tab base 230 resides outside the aperture 220 and adjacent to the bottom surface of the base 204. In one variation, the tab 206 is made of soft compliant material, such as silicone, that mimics the consistency of real tissue. The silicone tabs 206 are easily deformed and pulled like real tissue making it suitable for practicing suturing and at the same time easily insertable into the apertures 220. The tab neck 232 has a shape in a cross-section taken perpendicular to the longitudinal axis of the tab 206 that substantially matches the shape or half the shape of the aperture 220 in which it is placed. A polygonal cross-sectional shape of the base neck 232 located inside a matching half or the full shape of the polygonal aperture 220 will be prevented from rotating inside the aperture 220 as opposed to a circular tab neck 232 inside a circular aperture 220. When placed inside the aperture 220, the tab neck 232 is substantially resident inside the aperture 220 between the top surface and the bottom surface of the base 204. The tab face 234 is resident above the top surface of the base 204. The tab face 234 includes at least one tab opening 236. The tab opening 236 may be any shape and size. In one variation, the tab opening 236 is a slit that is not readily apparent to the user. However, grasping the tab face 234 and pulling on it, as shown in FIG. 24B, elongates the tab face 234, and thereby, enlarges the tab opening 236 so that a suture may be passed through the tab opening 236. As such, the tab 206 has first configuration that is a relaxed configuration in which the tab opening 236 has a smaller first size and a second configuration that is stretched or elongated in which the tab opening 236 has a second size that is relatively larger. The elastic property of the tab material permits this tab to be moved from the first configuration to the second configuration. When the tab 236 is released from the second configuration, the tab 236 springs back to its relaxed first configuration. The tab opening 236 advantageously serves as a location to pass a suture wherein missing the tab opening 236 may serve as a means to measure the skill of the user. Also, the tab opening 236 helps to prevent the suture from tearing through the soft silicone of the tab face 234. In one variation, the tab face 234 is reinforced with mesh material to help hold a suture especially in a variation in which the tab face 234 does not including a tab opening 236. In such a variation, the tab face 234 is open to being pierced by the user in any location of the tab face 234. The transition between the tab base 230 and the tab neck 232 creates a ledge 238 around the tab 206 that prevents the tab 206 from being pulled proximally out of the aperture 220. Also, the transition between the tab neck 232 and the tab face 234 forms an undercut 240 that prevents the tab 206 from being pushed distally out of the aperture 220. Both the ledge 238 and undercut 240 help keep the tab 206, together with the faceted tab neck 232, which prevents rotation of the tab 206 relative to the base, securely yet removably, attached to the base 204 and capable of withstanding pulls and tugs associated with the suturing procedure.

A plurality of tabs 206 are typically inserted in various apertures 220 randomly selected throughout the base 204 or inserted in a predetermined fashion and configuration to create a predetermined suture pathway which can be associated with a particular level of difficulty for improving skill or mimicking a particular suture pathway likely to be encountered in a real surgical procedure. As such, any number of tabs 206 may be inserted into the base 204. Some apertures 220 may be left without tabs as desired. Approximately ten tabs 206 are inserted into the base 204 to create a prolonged practice session. Color-coded tabs 206 may be employed for the user to discern a predetermined suture pathway in which only red colored tabs 206 are to be pierced, for example, in a suture training exercise.

Figure 25:
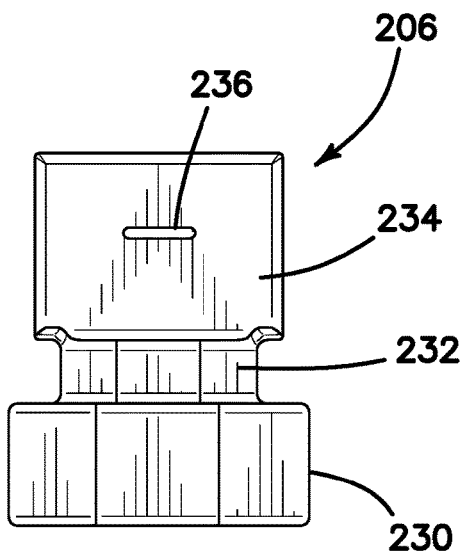
FIG. 25 illustrates a front elevational view of a tab according to the present invention.
Figure 26:
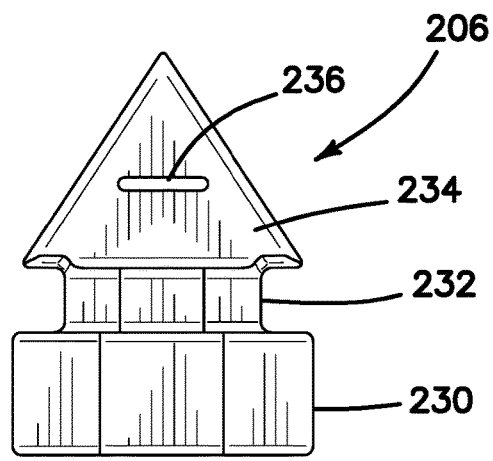
FIG. 26 illustrates a front elevational view of a tab according to the present invention.
Figures 27, 28, 29:
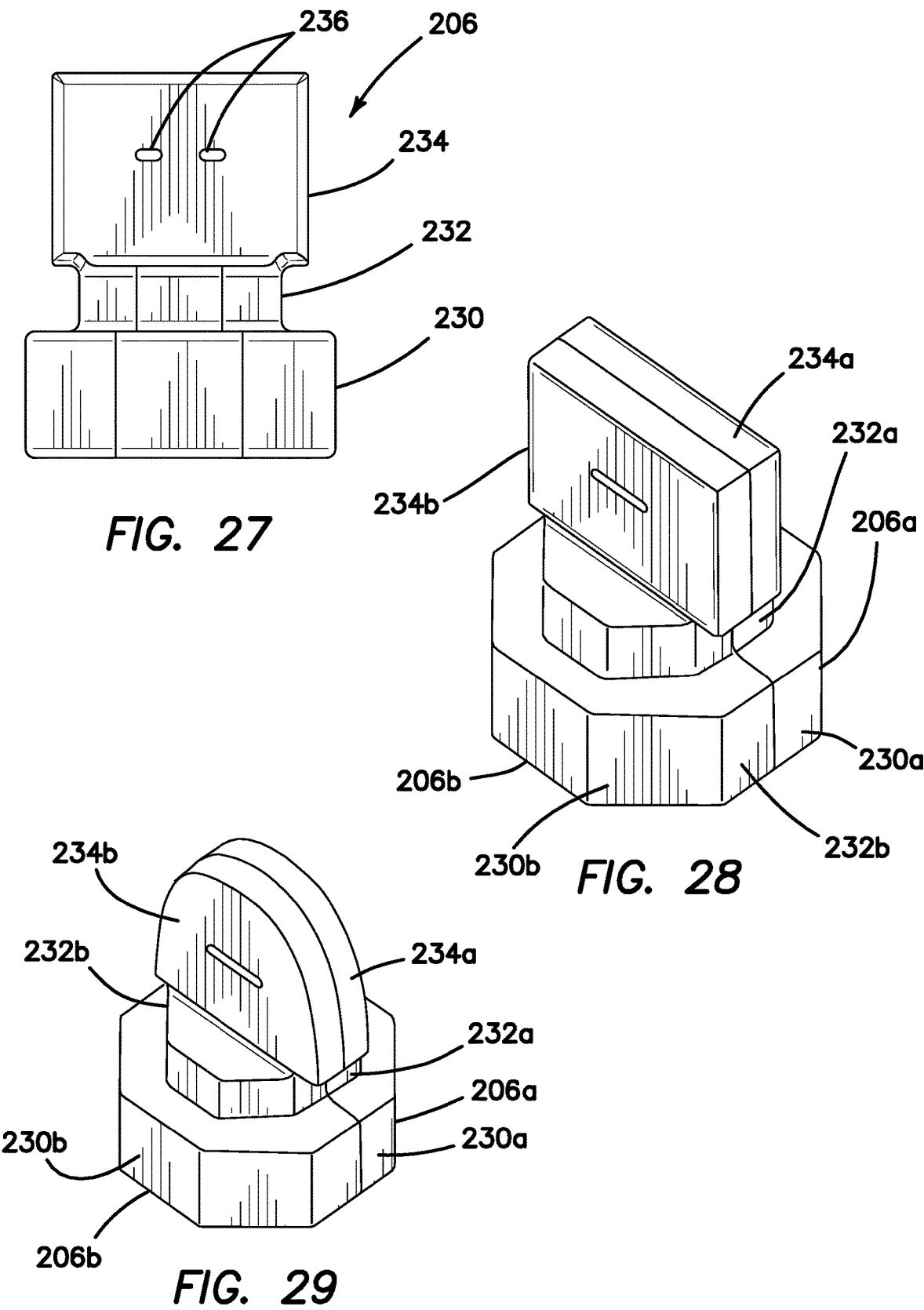
FIG. 27 illustrates a front elevational view of a tab according to the present invention.
FIG. 28 illustrates a top perspective view of two side-by-side half tabs according to the present invention.
FIG. 29 illustrates a top perspective view of two side-by-side half tabs according to the present invention.

Furthermore, with particular reference to FIGS. 25-27, the tab face 234 is configured with a shape in cross-section perpendicular to the longitudinal axis that is polygonal such as square, rectangular, as shown in FIG. 25, and triangular as shown in FIG. 26. Any shape such as circular, curved, elliptical are also within the scope of the present invention. The tabs 206 are designed in a variety of shapes and sizes to provide a variety of feature shapes for grasping, pulling and manipulating as well as a variety of tab opening 236 sizes and shapes. The tab opening 236 in FIGS. 25-26 is an elongated slit that has long axis and a short axis with the long axis substantially perpendicular to the longitudinal axis of the tab. In another variation, the slit is elongated at an angle or substantially parallel to the longitudinal axis. The tab opening 236 may have a long axis of approximately 0.25 inches long, 0.125 inches long, 0.0625 inches long, and 0.03125 inches in length for example. FIG. 27 also illustrates a variation of the face 234 that has more than one tab opening 236. In particular, two openings 236 in the shape of slits are located side-by-side and substantially along a line perpendicular to the longitudinal axis. These two side-by-side slits are each approximately 0.03125 inches in length.

In one variation of the tab 206 shown in FIGS. 23A-23D, the tab base 230 and tab neck 232 are approximately half the size and shape of a base aperture 220. This configuration permits two half tabs 206a, 206b to be placed side-by-side, back-to-back inside the same base opening 220 as shown in FIGS. 28-33. The tabs 206 are configured with a size and shape that facilitates secure attachment to the base 204 through friction and geometric constraints. The tabs 206 are kept from rotating inadvertently within the apertures 220 of the base 204 by the shape of the tab neck 232 wherein the corners of the trapezoid and/or polygon of the tab neck 232 hinder rotation out of the corners of the polygonal/octagonal aperture 220 of the openings 220 in the base 204 when the corners of the tab neck 232 are located within corresponding corners of the polygonal aperture 220. Furthermore, the octagonal shape of the aperture 220 and the corresponding shape of the tab neck 232 allow for four rotational orientations of the tabs 206 with a base aperture 220, and therefore, advantageously, a plurality of suture pathways and approach orientations for varied practice, that is, the tab 206 can be inserted in a first orientation defined along twelve o'clock and six o'clock and removed and re-inserted in a second orientation defined along a nine o'clock and three o'clock position and re-inserted in a third orientation defined along approximately the two-o'clock and the eight o'clock position and a fourth orientation defined along approximately the ten o'clock and four o'clock position.

Figure 30:
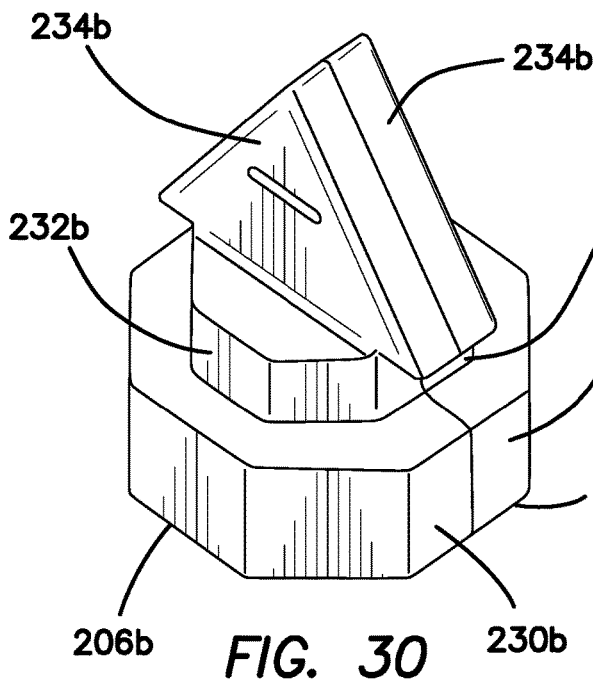
FIG. 30 illustrates a top perspective view of two side-by-side half tabs according to the present invention.
Figure 31A:
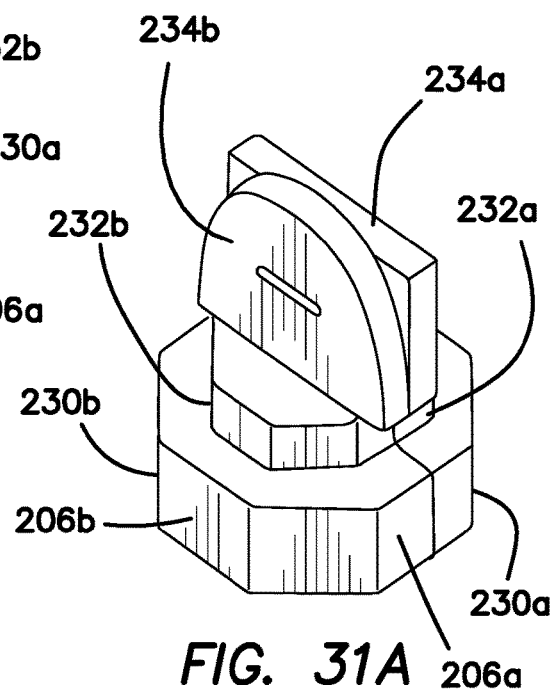
FIG. 31A illustrates a top perspective view of two side-by-side half tabs according to the present invention.
Figure 31B:
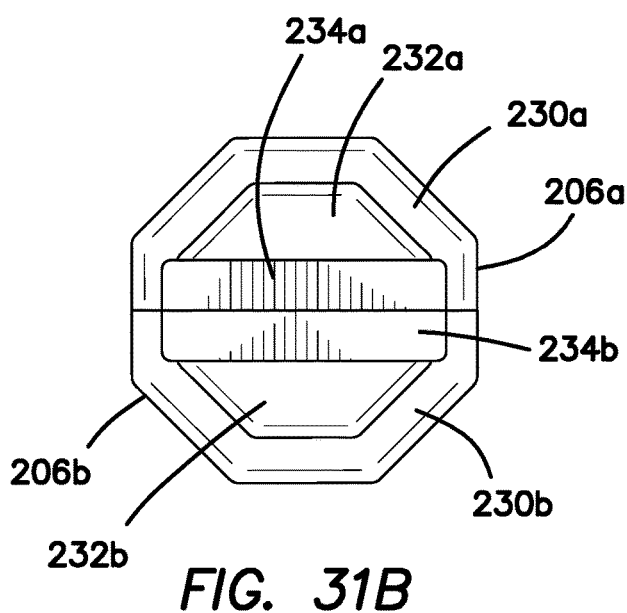
FIG. 31B illustrates a top view of two side-by-side half tabs of FIG. 31A according to the present invention.
Figure 31C:
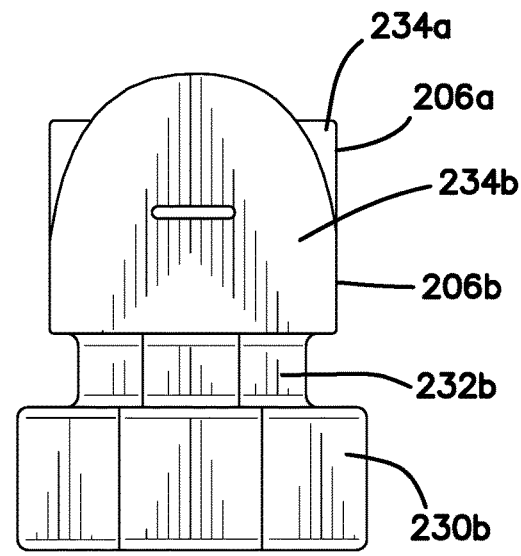
FIG. 31C illustrates a front elevational view of two side-by-side half tabs of FIG. 31A according to the present invention.
Figure 32A:
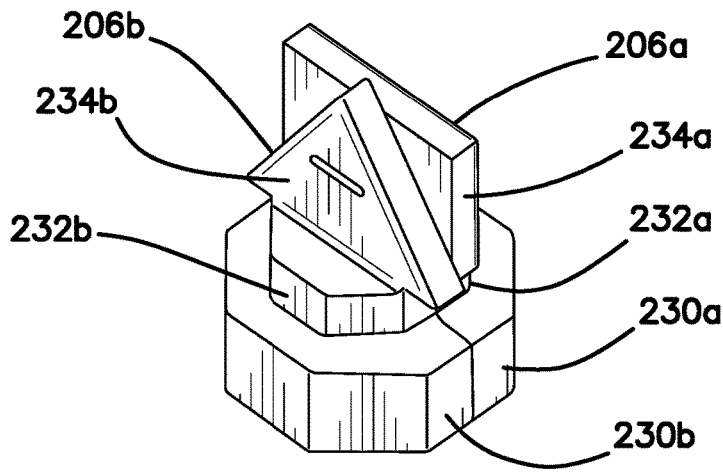
FIG. 32A illustrates a top perspective view of a two side-by-side half tabs according to the present invention.
Figure 32B:
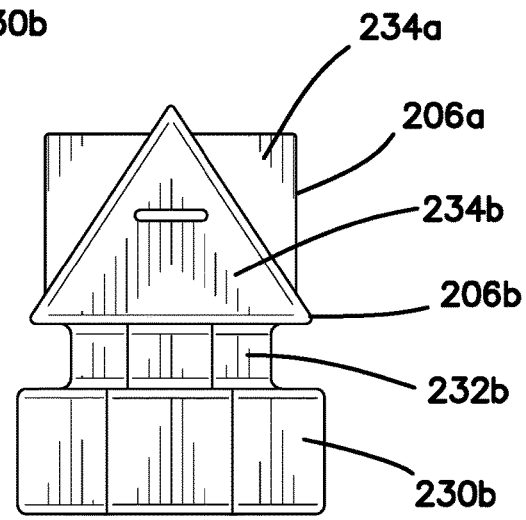
FIG. 32B illustrates a front elevational view of two side-by-side half tabs of FIG. 32A according to the present invention.
Figure 32C:
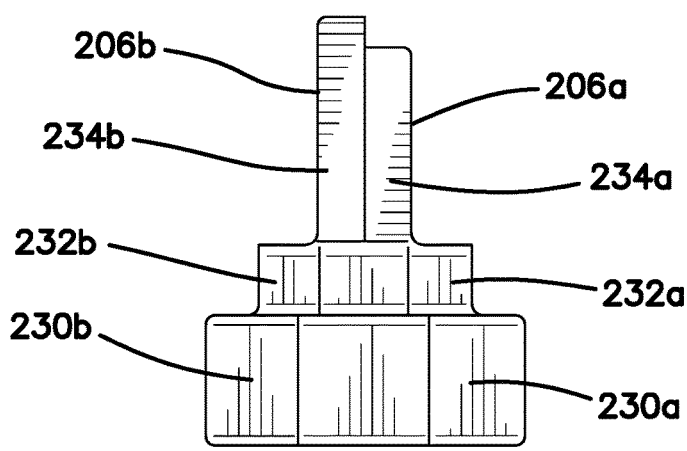
FIG. 32C illustrates a side elevational view of two side-by-side half tabs of FIG. 32A according to the present invention.
Figure 33A:
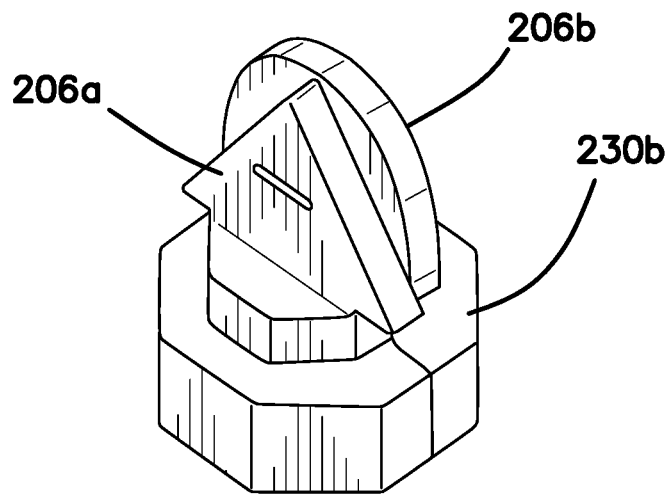
FIG. 33A illustrates a top perspective view of two side-by-side half tabs according to the present invention.
Figure 33B:
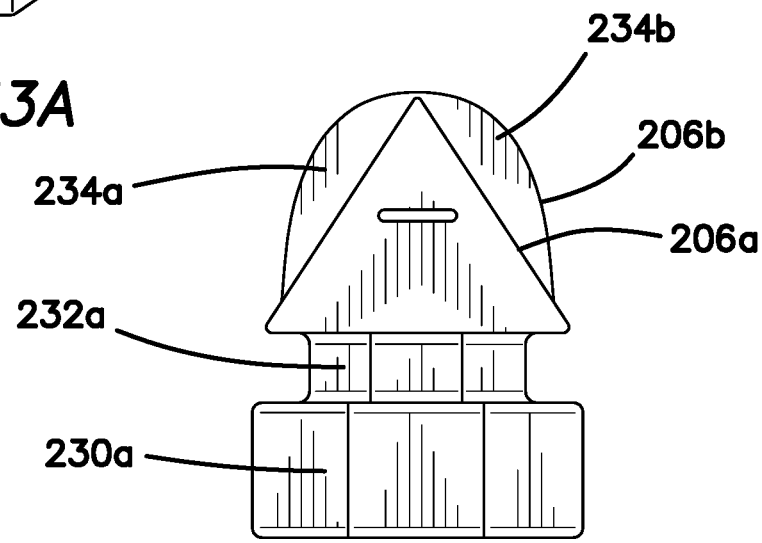
FIG. 33B illustrates a front elevational view of two side-by-side half tabs of FIG. 33A according to the present invention.
Figure 33C:
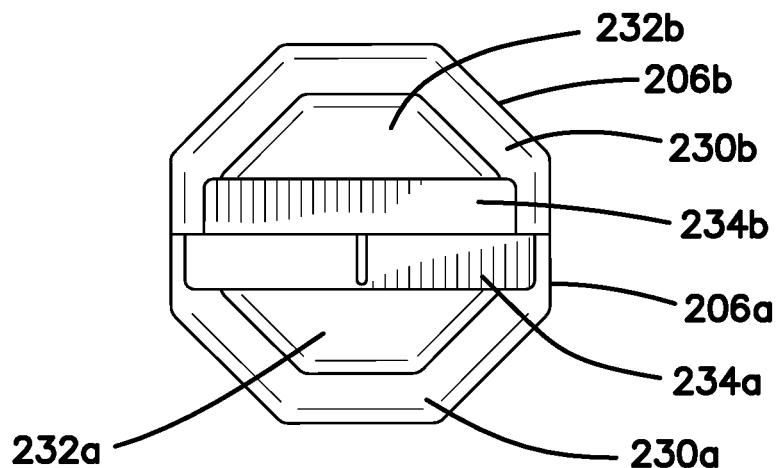
FIG. 33C illustrates a top view of two side-by-side half tabs of FIG. 33A according to the present invention.

With continued reference to FIGS. 28-33, in the variation in which the tab 206 comprises a first half tab 206 and a second half tab 206b, the first half tab 206a has a tab base 230a and tab neck 232a having a first shape and the second half tab 206b has a tab base 230b and a tab neck 232b having a second shape. Both the first shape and the second shape complement each other at the adjoining surface and complete the full peripheral shape of the base aperture 220. Since two half tabs 206a, 206b are inserted into a single aperture 220, the skill level is advantageously increased or the practice made more difficult by arrangement of different tabs 206 side-by-side. For example, one half tab 206a may have no tab openings 236 thereby concealing a tab opening 236 in an adjacent half tab 206b. In another example, the half-tabs 206a, 206b may be of different color so that a practice exercise instruction would be to suture through the tabs of the same color requiring the user to grasp the tab 206 of the correct color. Furthermore, grasping half-tabs 206a, 206b that are located side-by-side in a base aperture 220 is more difficult than grasping a single tab 206 inside a base aperture 220. Also, two half tabs 206a, 206b side-by-side inside a single base aperture 220 may have tab faces 234a, 234b that are the same as shown in FIGS. 28, 29 and 30 in which the tab faces 234a, 234b are polygonal, curved, and triangular, respectively. In another variation, two half tabs 206a, 206b side-by-side inside a single base aperture 220 may have tab faces 234a, 234b that different from each other. For example, in FIGS. 31, 32, and 33, tab face 234a is polygonal and tab face 234b is curved, tab face 234a is polygonal and tab face 234b is triangular, and tab face 234a is triangular and tab face 234b is curved, respectively. If the tab faces 234a, 234b are the same, the skill level in differentiating the two tab faces from each other is increased as well as the difficulty in grasping one of them as opposed to a variation in which only one tab face 234 is provided within a single base aperture 220. Grasping the surfaces of tab face 234a or 234b is discernible as the overlapping portions of the differently shaped adjacent tab face as can be seen in FIGS. 31C, 32B and 33B. Of course, in another variation, a single tab 206 may be provided with two upstanding tab faces 234 having different tab opening 236 configurations and/or shapes of tab faces 234 while sharing a common tab base 230 and tab neck 232.

While certain embodiments have been particularly shown and described with reference to exemplary embodiments thereof, it will be understood by those of ordinary skill in the art that various changes in form and details may be made therein without departing from the spirit and scope thereof as defined by the following claims.

We claim:

1. A method for practicing suture passing comprising the steps of:
providing a suture training model comprising a base configured to hold a plurality of suture tabs; each of the plurality of suture tabs having a first side interconnected with a second side to form a top portion and a bottom portion; the first and second sides being substantially vertical and interconnected by the top and bottom portions such that a ledge is defined at an intersection between the top portion and the bottom portion or a tab neck interconnects the top portion with the bottom portion; the base includes a plurality of openings perforating the base for receiving the plurality of suture tabs; the plurality of suture tabs being configured to have a resting configuration and an elongated configuration along a longitudinal axis so that when a suture tab located inside one of the plurality of openings is pulled into the elongated configuration, the bottom portion of the suture tab is retained with respect to the base while a length of the suture tab along the longitudinal axis is increased relative to the resting configuration;
providing a suture and a suture needle;
pulling one of the plurality of suture tabs located inside one of the plurality of the openings relative to the base from the resting configuration to the elongated configuration; and
passing the suture and suture needle through the top portion of the pulled suture tab while in the elongated configuration.

2. The method of claim 1 wherein the step of providing a suture training model comprises providing a suture training model with some top portions of the plurality of suture tabs having at least one pre-formed aperture and the step of passing the suture and suture needle comprises passing the suture through the at least one pre-formed aperture.

3. The method of claim 2 wherein the at least one pre-formed aperture extends laterally between the first side and the second side through said some top portions; the at least one pre-formed aperture comprising an elongate slit having a long axis and a short axis.

4. The method of claim 3 wherein the long axis of the slit is substantially perpendicular to the longitudinal axis, elongated at an angle relative to the longitudinal axis, or substantially parallel to the longitudinal axis of the suture tab.

5. The method of claim 2 further comprising the step of stretching the one suture tab to enlarge the at least one pre-formed aperture.

6. The method of claim 1 wherein the step of providing a suture training model comprises providing a suture training model with some top portions of the plurality of suture tabs defining a penetrable region with no pre-formed aperture and the step of passing the suture and suture needle comprises piercing the penetrable region by the suture needle to create an aperture and passing the suture through the aperture being pierced.

7. The method of claim 6 further comprising the step of stretching the one suture tab to enlarge the aperture being pierced.

8. The method of claim 1 further comprising the step of creating a predetermined suture pathway for practicing an intended surgical procedure or different skill levels.

9. The method of claim 8 wherein the step of creating a predetermined suture pathway further comprises the steps of:
inserting some of the plurality of suture tabs into the plurality of openings in a random or predetermined fashion; and
aligning each suture tab of said some of the plurality of suture tabs with one opening of the plurality of openings, wherein the aligning step is performed prior to insertion of each suture tab.

10. The method of claim 9 wherein the step of inserting some of the plurality of suture tabs comprises approaching a bottom surface of the base while aligning one of said some of the plurality of suture tabs with one opening from the plurality of openings and inserting the suture tab into the one opening such that the top portion of the suture tab as aligned leads the insertion into the one opening.

11. The method of claim 10 wherein when the suture tab is sufficiently inserted into the one opening, the ledge formed between the top portion and the bottom portion of the suture tab abuts the bottom surface of the base to retain the suture tab inside the one opening and at least part of the top portion of the suture tab resides above a top surface of the base.

12. The method of claim 10 wherein when the suture tab is sufficiently inserted into the one opening, the tab neck of the suture tab resides inside the one opening between the top and bottom surfaces of the base.

13. The method of claim 12 wherein at least part of the top portion of the suture tab resides above a top surface of the base while the bottom portion resides outside the opening and adjacent to the bottom surface of the base.

14. The method of claim 9 wherein the aligning step further comprises the step of selecting an orientation of the suture tab, if the one opening permits multiple orientations of the suture tab.

15. The method of claim 1 wherein the bottom portion of each of the plurality of suture tabs has a projection in a plane perpendicular to the longitudinal axis that is larger than a projection of the top portion in the same plane.

16. The method of claim 1 wherein the bottom portion of each of the plurality suture tabs is wider than its top portion so as to prevent the bottom portion from being pulled proximally through any one of the plurality of openings.

17. The method of claim 1 wherein the step of providing a suture training model comprises providing a suture training model with the base having a top surface interconnected with a bottom surface; the top surface being parallel to the bottom surface so as to define a substantially planar structure having a thickness; the plurality of openings being formed in the base extending between the top surface and the bottom surface.

18. The method of claim 1 wherein the step of providing a suture training model further comprises providing a suture training model having a stand with mating features to hold the base at various orientations relative to the stand.

19. The method of claim 1 wherein the step of providing a suture training model further comprises providing a suture training model with the base having at least one angle to form at least two planes with openings holding the plurality of suture tabs.

20. The method of claim 19 further comprising the step of molding integrally the at least two planes or interconnecting the at least two planes using a hinge.

* * * * *